US011198881B2

(12) United States Patent
Argyros et al.

(10) Patent No.: US 11,198,881 B2
(45) Date of Patent: Dec. 14, 2021

(54) YEAST EXPRESSING HETEROLOGOUS GLUCOAMYLASE

(71) Applicants: Lallemand Hungary Liquidity Management LLC, Budapest (HU); BASF SE, Ludwigshafen (DE)

(72) Inventors: Aaron Argyros, Lebanon, NH (US); Alexandra Panaitiu, Enfield, NH (US); Charles Rice, Plainfield, NH (US); Kenneth Barrett, San Diego, CA (US)

(73) Assignees: Lallemand Hungary Liquidity Management LLC, Budapest (HU); BASF SE, Ludwigshafen (DE)

( * ) Notice: Subject to any disclaimer, the term of this patent is extended or adjusted under 35 U.S.C. 154(b) by 0 days.

(21) Appl. No.: 17/105,045

(22) Filed: Nov. 25, 2020

(65) Prior Publication Data

US 2021/0163967 A1    Jun. 3, 2021

Related U.S. Application Data

(60) Provisional application No. 62/941,967, filed on Nov. 29, 2019, provisional application No. 63/078,135, filed on Sep. 14, 2020.

(51) Int. Cl.
| | |
|---|---|
| *C12N 1/20* | (2006.01) |
| *C12N 15/75* | (2006.01) |
| *C12N 15/81* | (2006.01) |
| *C12N 9/26* | (2006.01) |
| *C12N 9/34* | (2006.01) |
| *C12P 7/06* | (2006.01) |

(52) U.S. Cl.
CPC ........... *C12N 15/81* (2013.01); *C12N 9/2414* (2013.01); *C12N 9/2428* (2013.01); *C12P 7/06* (2013.01); *C12Y 302/01001* (2013.01); *C12Y 302/01003* (2013.01)

(58) Field of Classification Search
CPC ......... C12N 9/2428; C12N 1/20; C12N 15/75
See application file for complete search history.

(56) References Cited

U.S. PATENT DOCUMENTS

| | | | |
|---|---|---|---|
| 6,255,084 B1 | 7/2001 | Nielsen et al. | |
| 6,620,924 B2 | 9/2003 | Nielsen et al. | |
| 7,060,468 B2 | 6/2006 | Nielsen et al. | |
| 7,129,069 B2 | 10/2006 | Borchert et al. | |
| 7,312,055 B2 | 12/2007 | Borchert et al. | |
| 7,749,744 B2 | 7/2010 | Borchert et al. | |
| 8,216,817 B2 | 7/2012 | Gill et al. | |
| 8,956,851 B2 | 2/2015 | Argyros et al. | |
| 9,206,444 B2 | 12/2015 | Brevnova et al. | |
| 9,605,269 B2 | 3/2017 | Sillers et al. | |
| 9,650,620 B2 | 5/2017 | Sun et al. | |
| 9,719,098 B2 | 8/2017 | Argyros et al. | |
| 10,253,337 B2 | 4/2019 | Cripwell et al. | |
| 10,294,484 B2 | 5/2019 | Brevnova et al. | |
| 10,344,288 B2 | 7/2019 | Miller et al. | |
| 10,364,421 B2 | 7/2019 | Miller et al. | |
| 10,385,345 B2 | 8/2019 | Brevnova et al. | |
| 10,570,421 B2 | 2/2020 | Rice et al. | |
| 2015/0037858 A1* | 2/2015 | Noda | C12P 7/10 435/165 |
| 2016/0194669 A1 | 7/2016 | Argyros et al. | |
| 2017/0356000 A1 | 12/2017 | Argyros et al. | |
| 2018/0265853 A1 | 9/2018 | Rice et al. | |
| 2019/0338319 A1* | 11/2019 | Yazdi | C12N 9/2428 |
| 2019/0345471 A1 | 11/2019 | Miller et al. | |
| 2020/0063221 A1 | 2/2020 | Jauert et al. | |
| 2020/0095592 A1 | 3/2020 | Brevnova et al. | |
| 2020/0231991 A1 | 7/2020 | Rice et al. | |

FOREIGN PATENT DOCUMENTS

| | | | |
|---|---|---|---|
| CA | 2 517 920 A1 | | 9/2004 |
| CA | 2 629 821 A1 | | 5/2007 |
| CA | 2 730 243 A1 | | 1/2010 |
| WO | 2011/053545 A1 | | 5/2011 |
| WO | 2014/202624 A2 | | 12/2014 |
| WO | 2018/027131 A1 | | 2/2018 |
| WO | WO 2018/027131 | * | 2/2018 |
| WO | 2018/167670 A1 | | 9/2018 |
| WO | 2019/168962 A1 | | 9/2019 |
| WO | 2019/175809 A1 | | 9/2019 |
| WO | 2019/191263 A1 | | 10/2019 |

(Continued)

OTHER PUBLICATIONS

Jansen, "Same Corn, More Value: Industrially Proven Yeast Technology," *Fuel Ethanol Workshop*, Indianapolis, Indiana, USA, Jun. 12, 2019, 18 pages.

Nielson, "Production of biopharmaceutical proteins by yeast: Advances through metabolic engineering," *Bioengineered* 4(4):207-211, 2013.

Richards, "Advanced Yeasts: Continuing Innovation in Response to Producer Requirements," *35th International Fuel Ethanol Workshop & Expo*, Jun. 12, 2019, 28 pages.

Richards, "Biotech Yeast: A Decade of Innovation to Assist Producers," *34th International Fuel Ethanol Workshop & Expo*, Jun. 13, 2018, 27 pages.

Richards, "Measurement of Ethanol Yield in Grain Ethanol Plant Trials," *Fuel Ethanol Workshop*, Jun. 3, 2015, 17 pages.

(Continued)

*Primary Examiner* — Tekchand Saidha
(74) *Attorney, Agent, or Firm* — Seed IP Law Group LLC

(57) ABSTRACT

The present disclosure concerns recombinant yeast host cell for saccharification of a biomass. The recombinant yeast host cell has a genetic modification for expressing a heterologous polypeptide having glucoamylase activity (*Rasamsonia emersonii* glucoamylase). In some embodiments, the heterologous polypeptide comprises the signal sequence associated with the alpha-mating 1 factor. The present disclosure also concerns a process for saccharification of a biomass using the recombinant yeast host cell as well as a process for fermenting the saccharified biomass into a fermentation product.

29 Claims, 5 Drawing Sheets
Specification includes a Sequence Listing.

(56) References Cited

FOREIGN PATENT DOCUMENTS

WO 2020/100069 A1 5/2020

OTHER PUBLICATIONS

Richards, "Pushing the Limits on Yield: Advanced Yeasts Providing Further Efficiencies in Fuel Ethanol Production," *33$^{rd}$ International Fuel Ethanol Workshop & Expo*, Jun. 21, 2017, 23 pages.
Richards, "The Next Generation of Yeast-Expressed Enzymes to Enhance Production," *36$^{th}$ International Fuel Ethanol Workshop & Expo*, Sep. 16, 2020, 20 pages.
Richards, "TransFerm® & TransFerm®: Yield +: Maximizing Profitability within Ethanol Facilities," *Sponsor Seminar, Fuel Ethanol Workshop*, Jun. 10, 2014, 16 pages.
Cripwell et al., "Construction of industrial *Saccharomyces cerevisiae* strains for the efficient consolidated bioprocessing of raw starch," *Biotechnol Biofuels 12*:201, 2019 (16 pages).

\* cited by examiner

YEAST EXPRESSING HETEROLOGOUS GLUCOAMYLASE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 580127_426_SEQUENCE_LISTING.txt. The text file is 151 KB, was created on Nov. 25, 2020, and is being submitted electronically via EFS-Web.

TECHNOLOGICAL FIELD

The present disclosure relates to a recombinant yeast host cell expressing enzymes and acting as a source of enzyme activity for saccharification and fermentation.

BACKGROUND

*Saccharomyces cerevisiae* is the primary biocatalyst used in the commercial production of fuel ethanol. This organism is proficient in fermenting glucose to ethanol, often to concentrations greater than 20% v/v. However, *S. cerevisiae* lacks the ability to hydrolyze polysaccharides. Consequently, in addition to yeast, industrial ethanol production requires the exogenous addition of expensive enzymes to convert complex sugars to glucose. For example, in the United States, the primary source of fuel ethanol is corn starch. Regardless of the mashing process, corn starch fermentation by yeast benefits from the exogenous addition of both α-amylase and glucoamylase.

The fermentation processes employed in the corn ethanol industry can be broadly classified based on utilized substrate into liquefied corn mash and raw corn flour fermentations. In the mashing process, corn is both thermally and enzymatically liquefied prior to fermentation using α-amylase, which breaks down long chain starch polymers into smaller dextrins. The mash is then cooled and inoculated with *S. cerevisiae*. Concomitantly, the exogenous purified glucoamylase is added. Glucoamylases (GAs) break down the branched dextrin into glucose molecules that are utilizable by yeast. GAs primarily hydrolyze α-1,4-glycosidic linkages from non-reducing ends in starch chain (they are, hence, exo-acting enzymes), while α-amylases can also hydrolyze α-1,6-glicosidic linkages from the inner starch chains (and are, therefore, endo-acting enzymes). The availability of a robust, ethanol-tolerant yeast strain is required to ferment the hydrolyzed starch into the desired final product, ethanol.

It would be highly desirable to be provided with improved and/or more efficient yeast strains which reduces or precludes the need for highly expensive enzyme purification and formulation, thus significantly reducing overall production costs. Since fermentation involves a number of stressors, improved and/or more efficient yeast trains are also needed with greater robustness.

BRIEF SUMMARY

The present disclosure provides recombinant yeast host cells which expresses starch digesting glucoamylases that can be used in saccharification and fermentation of a biomass. The present disclosure concerns recombinant yeast host cells expressing a heterologous starch digesting glucoamylase by introducing a heterologous nucleic acid molecule encoding for the glucoamylase enzyme as well as a signal sequence allowing the secretion of the glucoamylase.

According to a first aspect, the present disclosure provides a recombinant yeast host cell for saccharification and fermentation of a biomass, the recombinant yeast host cell having a heterologous nucleic acid molecule encoding a heterologous polypeptide having glucoamylase activity. The heterologous nucleic acid molecule comprises a first polynucleotide encoding a heterologous signal sequence wherein the heterologous signal sequence has the amino acid sequence of SEQ ID NO: 5, is a variant of the amino acid sequence of SEQ ID NO: 5 having signal sequence activity, or is a fragment of the amino acid sequence of SEQ ID NO: 5 having signal sequence activity. The heterologous nucleic acid also comprises a second polynucleotide encoding the heterologous polypeptide having glucoamylase activity, wherein the polypeptide having glucoamylase activity has the amino acid sequence of SEQ ID NO: 3 or 13, is a variant of the amino acid sequence of SEQ ID NO: 3 or 13 having glucoamylase activity, or is a fragment of the amino acid sequence of SEQ ID NO: 3 or 13 having glucoamylase activity. In the recombinant yeast host cell of the present disclosure, the first polynucleotide molecule is operatively associated with the second polynucleotide molecule. In an embodiment, the heterologous nucleic acid molecules encodes the heterologous polypeptide having the amino acid sequence of SEQ ID NO: 1 or 11, a variant of the amino acid sequence of SEQ ID NO: 1 or 11 having glucoamylase activity, or a fragment of the amino acid sequence of SEQ ID NO: 1 or 11 having glucoamylase activity. In yet another embodiment, the heterologous nucleic acid molecule further comprises a third polynucleotide comprising a heterologous promoter operatively associated with the first polynucleotide and the second polynucleotide allowing the expression of the heterologous polypeptide having glucoamylase activity. In an embodiment, the heterologous promoter is capable of allowing the expression of the heterologous polypeptide having glucoamylase activity during propagation. In an embodiment, the heterologous polypeptide having glucoamylase activity is a secreted polypeptide. In another embodiment, the heterologous polypeptide having glucoamylase activity is a membrane-associated polypeptide, such as, for example, a tethered polypeptide. In an embodiment, the recombinant yeast host cell comprising a further heterologous nucleic acid molecule encoding a heterologous alpha-amylase or a heterologous glucoamylase. In another embodiment, the heterologous alpha-amylase has the amino acid sequence of any one of SEQ ID NO: 17 to 26, is a variant of the amino acid sequence of any one of SEQ ID NO: 17 to 27 having alpha-amylase activity or is a fragment of the amino acid sequence of any one of SEQ ID NO: 17 to 26 having alpha-amylase activity. In yet another embodiment, the heterologous glucoamylase has the amino acid sequence of any one of SEQ ID NO: 27 to 36, is a variant of the amino acid sequence of any one of SEQ ID NO: 26 to 36 having glucoamylase activity or is a fragment of the amino acid sequence of any one of SEQ ID NO: 27 to 36 having glucoamylase activity. In an embodiment, the recombinant yeast host cell is from the genus *Saccharomyces*, such as, for example, from the species *Saccharomyces cerevisiae*.

According to a second aspect, the present disclosure provides a composition comprising the recombinant yeast host cell described herein and starch.

According to a third aspect, the present disclosure provides a process for saccharification and fermentation of a biomass into a fermentation product, the process comprises contacting the biomass with the recombinant yeast host cell defined herein or the composition defined herein, under a condition that allows the conversion of at least a part of the biomass into the fermentation product (in some embodiments during a fermentation). In an embodiment, the biomass is derived from or comprises corn, potato, cassava, rice, wheat, cellulosic material, milo (grain sorghum) or buckwheat. In another embodiment, the biomass is derived from or comprises corn. In still another embodiment, the biomass comprises or is corn mash. In an embodiment, the fermentation product is ethanol. In another embodiment, the conversion/fermentation is conducted in the presence of a stressor. In yet a further embodiment, the stressor is low pH (such as, for example, a pH of 5.0 or lower or a pH of 4.0 or lower). In still a further embodiment, the stressor is an elevated temperature. In yet another embodiment, the process comprises including an exogenous enzyme in the biomass. For example, the exogenous enzyme can be an alpha-amylase (which may, in some further embodiments, have the amino acid sequence of any one of SEQ ID NO: 17 to 26, be a variant of the amino acid sequence of any one of SEQ ID NO: 17 to 27 having alpha-amylase activity or be a fragment of the amino acid sequence of any one of SEQ ID NO: 17 to 26 having alpha-amylase activity. In another example, the exogenous enzyme can be a glucoamylase (which may, in some further embodiments, have the amino acid sequence of any one of SEQ ID NO: 27 to 36, be a variant of the amino acid sequence of any one of SEQ ID NO: 27 to 36 having glucoamylase activity or be a fragment of the amino acid sequence of any one of SEQ ID NO: 27 to 36 having glucoamylase activity. In some embodiments, the process avoids including an exogenous enzyme (e.g., achieve 100% enzyme displacement). In some embodiments, the exogenous enzyme is a glucoamylase.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION

Figure 1:
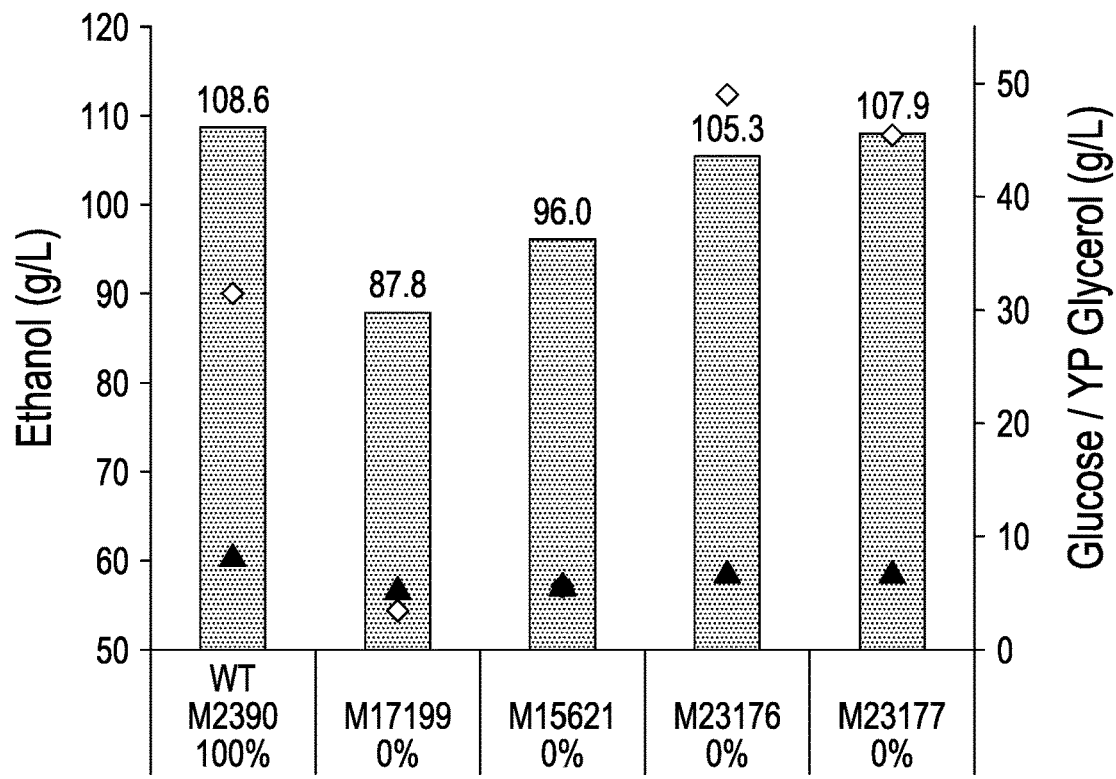
FIG. 1 illustrates the data associated with a corn mash fermentation (analyzed 23 hours into the fermentation). Bars represent midpoint ethanol titers in fermentation (plotted on the left y axis, in g/L). Lozenges (♦) denote glucose titers and triangles (▲) represent yeast-produced (YP) glycerol titers (right y axis, all in g/L). Results are shown for strains M2390, M17199, M15621, M23176 and M23177 (see Table 1 for a description of the strains). The amount (% of control dose) of exogenous glucoamylase used is listed under each bar.

The present disclosure provides recombinant yeast host cells that can be used under conditions of saccharification and fermentation of a biomass. Glucoamylase are usually secreted by the cell expressing a gene encoding same. Most glucoamylase sequences include a signal sequence which enables or facilitates the secretion of the enzyme. In the present disclosure, it has been recognized that using a signal sequence from the *Saccharomyces cerevisiae* alpha-mating factor 1 (e.g., having the amino acid sequence of SEQ ID NO: 5, a variant thereof or a fragment thereof) allows the displacement, at least in part, of exogenous (purified) glucoamylase during the fermentation process. In some additional embodiments, using a signal sequence from the *Saccharomyces cerevisiae* alpha-mating factor 1 (e.g., having the amino acid sequence of SEQ ID NO: 5, a variant thereof or a fragment thereof) increased the robustness of the recombinant yeast host cell expressing same.

Recombinant Yeast Host Cell

The heterologous polypeptides having glucoamylase activity are expressed in a recombinant yeast host cell. As such, the recombinant yeast host cell of the present disclosure includes at least one genetic modification. In the context of the present disclosure, when recombinant yeast cell is qualified has "having a genetic modification" or as being "genetically engineered", it is understood to mean that it has been manipulated to either add at least one or more heterologous or exogenous nucleic acid residue and/or remove at least one endogenous (or native) nucleic acid residue. The genetic manipulation(s) did not occur in nature and is the results of in vitro manipulations of the recombinant host cell. When the genetic modification is the addition of a heterologous nucleic acid molecule, such addition can be made once or multiple times at the same or different integration sites. When the genetic modification is the modification of an endogenous nucleic acid molecule, it can be made in one or both copies of the targeted gene/non-coding region. In a specific embodiment, the recombinant yeast host cell having the genetic modification has a heterologous nucleic acid molecule encoding a heterologous polypeptide having glucoamylase activity.

When expressed in a recombinant yeast host cell, the heterologous polypeptide (having glucoamylase activity, e.g. a glucoamylase) described herein are encoded on one or more heterologous nucleic acid molecule. In some embodiments, heterologous polypeptide described herein can be encoded on one heterologous nucleic acid molecule, two heterologous nucleic acid molecules or copies, three heterologous nucleic acid molecules or copies, four heterologous nucleic acid molecules or copies, five heterologous nucleic acid molecules or copies, six heterologous nucleic acid molecules or copies, seven heterologous nucleic acid molecules or copies, or eight or more heterologous nucleic acid molecules or copies. The term "heterologous" when used in reference to a nucleic acid molecule (such as a promoter or a coding sequence) refers to a nucleic acid molecule that is not natively found in the recombinant yeast host cell. "Heterologous" also includes a native coding region, or portion thereof, that was removed from the organism (which can, in some embodiments, be a source organism) and subsequently reintroduced into the organism in a form that is different from the corresponding native gene, e.g., not in its natural location in the organism's genome. The heterologous nucleic acid molecule is purposively introduced into the recombinant yeast host cell. The term "heterologous" as used herein also refers to an element (nucleic acid or polypeptide) that is derived from a source other than the endogenous source. Thus, for example, a heterologous element could be derived from a different strain of host cell, or from an organism of a different taxonomic group (e.g., different kingdom, phylum, class, order, family genus, or species, or any subgroup within one of these classifications).

When a heterologous nucleic acid molecule is present in the recombinant yeast host cell, it can be integrated in the host cell's chromosome. The term "integrated" as used herein refers to genetic elements that are placed, through molecular biology techniques, into the chromosome(s) of the recombinant yeast host cell. For example, genetic elements can be placed into the chromosome(s) of the host cell as opposed to in a vector such as a plasmid carried by the host cell. Methods for integrating genetic elements into the chromosome(s) of a host cell are well known in the art and include homologous recombination. The heterologous nucleic acid molecule can be present in one or more copies in the yeast host cell's chromosome(s). Alternatively, the heterologous nucleic acid molecule can be independently replicating from the yeast's chromosome. In such embodiment, the nucleic acid molecule can be stable and self-replicating.

In the context of the present disclosure, the yeast host cell can be a recombinant yeast host cell. Suitable yeast host cells can be, for example, from the genus *Saccharomyces*, *Kluyveromyces*, *Arxula*, *Debaryomyces*, *Candida*, *Pichia*, *Phaffia*, *Schizosaccharomyces*, *Hansenula*, *Kloeckera*, *Schwanniomyces* or *Yarrowia*. Suitable yeast species can include, for example, *Saccharomyces cerevisiae*, *Saccharomyces bulderi*, *Saccharomyces barnetti*, *Saccharomyces exiguus*, *Saccharomyces uvarum*, *Saccharomyces diastaticus*, *Kluyveromyces lactis*, *Kluyveromyces marxianus* or *Kluyveromyces fragilis*. In some embodiments, the yeast is selected from the group consisting of *Saccharomyces cerevisiae*, *Schizzosaccharomyces pombe*, *Candida albicans*, *Pichia pastoris*, *Pichia stipitis* (*Komagatella phaffi*), *Yarrowia lipolytica*, *Hansenula polymorpha*, *Phaffia rhodozyma*, *Candida utilis*, *Arxula adeninivorans*, *Debaryomyces hansenfi*, *Debaryomyces polymorphus*, *Schizosaccharomyces pombe* and *Schwanniomyces occidentalis*. In one particular embodiment, the yeast is *Saccharomyces cerevisiae*. In some embodiments, the host cell can be an oleaginous yeast cell. For example, the oleaginous yeast host cell can be from the genus *Blakeslea*, *Candida*, *Cryptococcus*, *Cunninghamella*, *Lipomyces*, *Mortierella*, *Mucor*, *Phycomyces*, *Pythium*, *Rhodosporidum*, *Rhodotorula*, *Trichosporon* or *Yarrowia*. In some alternative embodiments, the host cell can be an oleaginous microalgae host cell (e.g., for example, from the genus *Thraustochytrium* or *Schizochytrium*). In an embodiment, the recombinant yeast host cell is from the genus *Saccharomyces* and, in some additional embodiments, from the species *Saccharomyces cerevisiae*.

In some embodiments, the nucleic acid molecules encoding the heterologous polypeptides, fragments or variants that can be introduced into the recombinant yeast host cells are codon-optimized with respect to the intended recipient recombinant yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized heterologous nucleic acid molecule described herein corresponds to between about 0.8 and 1.0, between about 0.8 and 0.9, or about 1.0.

The heterologous nucleic acid molecules of the present disclosure can comprise a coding region for the heterologous polypeptide. A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

The nucleic acid molecules described herein can comprise transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

The heterologous nucleic acid molecule can be introduced in the host cell using a vector. A "vector," e.g., a "plasmid", "cosmid" or "artificial chromosome" (such as, for example, a yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Heterologous Polypeptide Having Glucoamylase Activity

The heterologous nucleic acid molecule includes a heterologous polynucleotide encoding a signal sequence. As it is known in the art, a signal sequence corresponds to a short stretch of amino acid residues (usually no longer than 50 contiguous amino acids and usually located at the amino terminus of the polypeptide) which are capable of guiding the remainder of the polypeptide for secretion. The signal sequence is usually cleaved upon the secretion of the polypeptide and thus is not necessarily involved with the enzymatic activity of the secreted polypeptide (e.g., glucoamylase activity in the present disclosure). In embodiments, the signal sequence encoded by the heterologous nucleic acid molecule (which can be associated with the heterologous polypeptide having glucoamylase activity) can have the amino acid sequence of the section spanning residues 1 to 21 of SEQ ID NO: 17, 1 to 21 of SEQ ID NO: 18, 1 to 23 of SEQ ID NO: 19, 1 to 19 of SEQ ID NO: 20, 1 to 25 of SEQ ID NO: 21, 1 to 22 of SEQ ID NO: 22, 1 to 29 of SEQ ID NO: 23, 1 to 16 of SEQ ID NO: 24, 1 to 23 of SEQ ID NO: 25, 1 to 21 of SEQ ID NO: 26, 1 to 17 of SEQ ID NO: 27, 1 to 20 of SEQ ID NO: 28, 1 to 22 of SEQ ID NO: 29, 1 to 18 of SEQ ID NO: 30, 1 to 25 of SEQ ID NO: 31, 1 to 19 of SEQ ID NO: 32, 1 to 18 of SEQ ID NO: 33, 1 to 19 of SEQ ID NO: 34, 1 to 18 of SEQ ID NO: 35, 1 to 18 of SEQ ID NO: 36 as well as variants and fragments thereof. In embodiments in which the heterologous polypeptide having glucoamylase activity has the amino acid sequence of SEQ ID NO: 3 or 13, the signal sequence encoded by the heterologous nucleic acid molecule (which can be associated with the heterologous polypeptide having glucoamylase activity) can have the amino acid sequence of SEQ ID NO: 5, a variant thereof or a fragment thereof.

The first polynucleotide can encode a signal sequence, a variant of a signal sequence having signal sequence activity or a fragment of a signal sequence having signal sequence activity. A variant signal sequence comprises at least one amino acid difference when compared to the amino acid sequence of the native or wild-type signal sequence and exhibits a biological activity substantially similar to the native (wild-type) signal sequence (e.g., the ability to guide the heterologous polypeptide having glucoamylase activity for secretion). The signal sequence "variants" have at least 50%, 55%, 60%, 65%, 70%, 75%, 80%, 85%, 90%, 95%, 96%, 97%, 98% or 99% of the biological activity when compared to the wild-type signal sequence described herein. The signal sequence "variants" have at least 50%, 55%, 60%, 65%, 70%, 75%, 80%, 85%, 90%, 95%, 96%, 97%, 98% or 99% identity to the wild-type signal sequence described herein. The level of identity can be determined conventionally using known computer programs. Identity can be readily calculated by known methods, including but not limited to those described in: Computational Molecular Biology (Lesk, A. M., ed.) Oxford University Press, N Y (1988); Biocomputing: Informatics and Genome Projects (Smith, D. W., ed.) Academic Press, N Y (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant signal sequence described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group. A "variant" of the wild-type signal sequence can be a conservative variant or an allelic variant. As used herein, a conservative variant refers to alterations in the amino acid sequence that do not adversely affect the biological functions of the signal sequence. A substitution, insertion or deletion is said to adversely affect the signal sequence when the altered sequence prevents or disrupts a biological function associated with the signal sequence. For example, the overall charge, structure or hydrophobic-hydrophilic properties of the signal sequence can be altered without adversely affecting a biological activity. Accordingly, the amino acid sequence can be altered, for example to render the signal sequence more hydrophobic or hydrophilic, without adversely affecting the biological activities of the signal sequence.

The signal sequence can be a fragment of the signal sequence or a fragment of a variant signal sequence. A signal sequence fragment comprises at least one less amino acid residue when compared to the amino acid sequence of the full length signal sequence or variant possesses and still possess a biological activity substantially similar to the native full-length signal sequence or variant. The signal sequence "fragments" have at least 50%, 55%, 60%, 65%, 70%, 75%, 80%, 85%, 90%, 95%, 96%, 97%, 98% or 99% of the biological activity when compared to the full-length signal sequence or variants described herein. Signal sequence "fragments" have at least at least 2, 3, 4, 5, 6, 7, 8, 9, 10 or more consecutive amino acids of the full-length signal sequence or variants described herein. The signal sequence "fragments" can have at least 50%, 55%, 60%, 65%, 70%, 75%, 80%, 85%, 90%, 95%, 96%, 97%, 98% or 99% identity to the full-length signal sequence or variants described herein.

The heterologous nucleic acid molecule of the present disclosure also includes a second polynucleotide encoding the heterologous polypeptide having glucoamylase activity. In the context of the present disclosure, the first and second polynucleotides are in frame and operatively associated so as to encode a single polypeptide (which is intended to be cleaved so as to release the polypeptide having glucoamylase activity upon the secretion of the single polypeptide). In the heterologous nucleic acid molecule, the first polynucleotide is located upstream (5') with respect to the second polynucleotide. Otherwise stated, the second polynucleotide is located downstream (3') with respect to the first polynucleotide in the heterologous nucleic acid sequence.

As indicated above, the recombinant yeast host cell can bear a genetic modification for expressing at least one heterologous polypeptide having glucoamylase activity. In some embodiments, the recombinant yeast host cell is obtained by introducing one or more heterologous nucleic acid molecule encoding one or more of the heterologous polypeptide in the recombinant yeast host cell. In some embodiments, the genetic modification(s) in the recombinant yeast host cell of the present disclosure comprise or consist essentially of or consist of expressing a heterologous polypeptide having glucoamylase activity. In the context of the present disclosure, the expression "the genetic modification in the recombinant yeast host consist essentially of a genetic modification for expressing a heterologous polypeptide having starch digesting glucoamylase activity" refers to the fact that the recombinant yeast host cell only includes this genetic modification to modulate the expression of a polypeptide having starch digesting glucoamylase activity levels but can nevertheless include other genetic modifications which are unrelated to the expression of a glucoamylase (native or heterologous).

As indicated above, the heterologous polypeptide is a polypeptide having starch digesting glucoamylase activity. As used herein, a polypeptide having glucoamylase activity refers to polypeptides having the ability to hydrolyze starch (which can have been heat-treated) directly to glucose. For example, a polypeptide having glucoamylase activity may comprise a catalytic domain and a starch binding domain. The catalytic domain and the starch binding domain may be connected by a connecting loop or linker. In some alternative embodiments, the polypeptides having glucoamylase activity can be derived from a fungus, for example, from the genus *Rasamsonia* (sometimes known or referred to as *Talaromyces*) and, in some instances, from the species *Rasamsonia emersonii* (sometimes known or referred to as *Talaromyces emersonii*). In some specific embodiments, the heterologous polypeptide having starch digesting glucoamylase activity can have the amino acid sequence of SEQ ID NO: 3 (which refers to Uniprot Q9C1V4), be a variant of the amino acid sequence of SEQ ID NO: 3 (having glucoamylase activity) or be a fragment of the amino acid sequence of SEQ ID NO: 3 (having glucoamylase activity). In yet another specific embodiment, the heterologous nucleic acid molecule can comprise the nucleic acid sequence of SEQ ID NO: 4, be a variant of the nucleic acid sequence of SEQ ID NO: 4 (encoding a glucoamylase) or be a fragment of the nucleic acid sequence of SEQ ID NO: 4 (encoding a glucoamylase). In another specific embodiment, the heterologous polypeptide having glucoamylase activity can have the amino acid sequence of SEQ ID NO: 1, be a variant of the amino acid sequence of SEQ ID NO: 1 (having glucoamylase activity) or be a fragment of the amino acid sequence of SEQ ID NO: 1 (having glucoamylase activity). In yet another specific embodiment, the heterologous nucleic acid molecule can comprise the nucleic acid sequence of SEQ ID NO: 2, be a variant of the nucleic acid sequence of SEQ ID NO: 2 (encoding a glucoamylase) or be a fragment of the nucleic acid sequence of SEQ ID NO: 2 (encoding a glucoamylase). In some specific embodiments, the heterologous polypeptide having starch digesting glucoamylase activity can have the amino acid sequence of SEQ ID NO: 13 (which refers to Uniprot A0A0F4YWQ6), be a variant of the amino acid sequence of SEQ ID NO: 13 (having glucoamylase activity) or be a fragment of the amino acid sequence of SEQ ID NO: 13 (having glucoamylase activity). In yet another specific embodiment, the heterologous nucleic acid molecule can comprise the nucleic acid sequence of SEQ ID NO: 14, be a variant of the nucleic acid sequence of SEQ ID NO: 14 (encoding a glucoamylase) or be a fragment of the nucleic acid sequence of SEQ ID NO: 14 (encoding a glucoamylase). In another specific embodiment, the heterologous polypeptide having glucoamylase activity can have the amino acid sequence of SEQ ID NO: 11, be a variant of the amino acid sequence of SEQ ID NO: 11 (having glucoamylase activity) or be a fragment of the amino acid sequence of SEQ ID NO: 11 (having glucoamylase activity). In yet another specific embodiment, the heterologous nucleic acid molecule can comprise the nucleic acid sequence of SEQ ID NO: 12, be a variant of the nucleic acid sequence of SEQ ID NO: 12 (encoding a glucoamylase) or be a fragment of the nucleic acid sequence of SEQ ID NO: 12 (encoding a glucoamylase).

In some further embodiments, the recombinant yeast host cell can include a further genetic modification (which can be the introduction of a further heterologous nucleic acid molecule) for expressing a further heterologous glucoamylase (e.g., different from the *R. emersonii* glucoamylase described above). For example, the further heterologous glucoamylase can be from a *Gloeophyllum* sp., such as, for example, from *Gloeophyllum trabeum*. In an embodiment, the further heterologous glucoamylase corresponds to Uniprot S7Q4V9 or GenBank Accession Number_007866834. In another embodiment, the further heterologous glucoamylase can have the amino acid sequence of SEQ ID NO: 27, be a variant of the amino acid sequence of SEQ ID NO: 27 having glucoamylase activity or be a fragment of the amino acid sequence of SEQ ID NO: 27 having glucoamylase activity (which can, in an embodiment, correspond to a fragment of the amino acid sequence of SEQ ID NO: 27 lacking its signal sequence, e.g., for example between residues 18 to 576 of SEQ ID NO: 27). For example, the further heterologous glucoamylase can be from a *Trichoderma* sp., such as, for example, from *Trichoderma reesii*. In an embodiment, the further heterologous glucoamylase corresponds to Uniprot G0R866 or GenBank Accession Number_XP_006960925. In another embodiment, the further heterologous glucoamylase can have the amino acid sequence of SEQ ID NO: 28, be a variant of the amino acid sequence of SEQ ID NO: 28 having glucoamylase activity or be a fragment of the amino acid sequence of SEQ ID NO: 28 having glucoamylase activity (which can, in an embodiment, correspond to a fragment of the amino acid sequence of SEQ ID NO: 28 lacking its signal sequence, e.g., for example between residues 21 to 632 of SEQ ID NO: 28). For example, the further heterologous glucoamylase can be from a *Trametes* sp., such as, for example, from *Trametes cingulata*. In another embodiment, the further heterologous glucoamylase can have the amino acid sequence of SEQ ID NO: 29, be a variant of the amino acid sequence of SEQ ID NO: 29 having glucoamylase activity or be a fragment of the amino acid sequence of SEQ ID NO: 29 having glucoamylase activity (which can, in an embodiment, correspond to a fragment of the amino acid sequence of SEQ ID NO: 29 lacking its signal sequence, e.g., for example between residues 23 to 574 of SEQ ID NO: 29). For example, the further heterologous glucoamylase can be from a *Athelia* sp., such as, for example, from *Athelia rolfsil*. In an embodiment, the further heterologous glucoamylase corresponds to Uniprot Q12596 or GenBank Accession Number_ BAA08436. In another embodiment, the further heterologous glucoamylase can have the amino acid sequence of SEQ ID NO: 30, be a variant of the amino acid sequence of SEQ ID NO: 30 having glucoamylase activity or be a fragment of the amino acid sequence of SEQ ID NO: 30 having glucoamylase activity (which can, in an embodiment, correspond to a fragment of the amino acid sequence of SEQ ID NO: 30 lacking its signal sequence, e.g., for example between residues 19 to 579 of SEQ ID NO: 30). For example, the further heterologous glucoamylase can be from a *Rhizopus* sp., such as, for example, from *Rhizopus oryzae*. In an embodiment, the further heterologous glucoamylase corresponds to Uniprot P07683 or GenBank Accession Number P07683. In another embodiment, the further heterologous glucoamylase can have the amino acid sequence of SEQ ID NO: 31, be a variant of the amino acid sequence of SEQ ID NO: 31 having glucoamylase activity or be a fragment of the amino acid sequence of SEQ ID NO: 31 having glucoamylase activity (which can, in an embodiment, correspond to a fragment of the amino acid sequence of SEQ ID NO: 31 lacking its signal sequence, e.g., for example, between residues 26 and 604 of SEQ ID NO: 31). For example, the further heterologous glucoamylase can be from a *Aspergillus* sp., such as, for example, from *Aspergillus oryzae*. In an embodiment, the further heterologous glucoamylase corresponds to Uniprot P36914 or GenBank Accession Number BAA00841. In another embodiment, the further heterologous glucoamylase can have the amino acid sequence of SEQ ID NO: 32, be a variant of the amino acid sequence of SEQ ID NO: 32 having glucoamylase activity or be a fragment of the amino acid sequence of SEQ ID NO: 32 having glucoamylase activity (which can, in an embodiment, correspond to a fragment of the amino acid sequence of SEQ ID NO: 32 lacking its signal sequence, e.g., for example between residues 20 to 612 of SEQ ID NO: 32). In yet another example, the further heterologous glucoamylase can be from *Aspergillus awamori*. In an embodiment, the further heterologous glucoamylase corresponds to Uniprot Q76L97 or GenBank Accession Number BAD06004. In another embodiment, the further heterologous glucoamylase can have the amino acid sequence of SEQ ID NO: 35, be a variant of the amino acid sequence of SEQ ID NO: 35 having glucoamylase activity or be a fragment of the amino acid sequence of SEQ ID NO: 35 having glucoamylase activity (which can, in an embodiment, correspond to a fragment of the amino acid sequence of SEQ ID NO: 35 lacking its signal sequence, e.g., for example between residues 19 to 639 of SEQ ID NO: 35). In yet another example, the further heterologous glucoamylase can be from *Aspergillus niger*. In an embodiment, the further heterologous glucoamylase corresponds to Uniprot Q870G8 or GenBank Accession Number AAP04499. In another embodiment, the further heterologous glucoamylase can have the amino acid sequence of SEQ ID NO: 36, be a variant of the amino acid sequence of SEQ ID NO: 36 having glucoamylase activity or be a fragment of the amino acid sequence of SEQ ID NO: 36 having glucoamylase activity (which can, in an embodiment, correspond to a fragment of the amino acid sequence of SEQ ID NO: 36 lacking its signal sequence, e.g., for example between residues 19 to 639 of SEQ ID NO: 36). For example, the further heterologous glucoamylase can be from a *Ophiostoma* sp., such as, for example, from *Ophiostoma floccosum*. In an embodiment, the further heterologous glucoamylase corresponds to Uniprot Q06SN2 or GenBank Accession Number ABF72529. In another embodiment, the further heterologous glucoamylase can have the amino acid sequence of SEQ ID NO: 33, be a variant of the amino acid sequence of SEQ ID NO: 33 having glucoamylase activity or be a fragment of the amino acid sequence of SEQ ID NO: 33 having glucoamylase activity (which can, in an embodiment, correspond to a fragment of the amino acid sequence of SEQ ID NO: 33 lacking its signal sequence, e.g., for example between residues 19 to 630 of SEQ ID NO: 33). For example, the further heterologous glucoamylase can be from a *Trichocladium* sp., such as, for example, from *Trichocladium griseum*. In an embodiment, the further heterologous glucoamylase corresponds to Uniprot Q12623 or GenBank Accession Number AAA33386. In another embodiment, the further heterologous glucoamylase can have the amino acid sequence of SEQ ID NO: 34, be a variant of the amino acid sequence of SEQ ID NO: 34 having glucoamylase activity or be a fragment of the amino acid sequence of SEQ ID NO: 34 having glucoamylase activity (which can, in an embodiment, correspond to a fragment of the amino acid sequence of SEQ ID NO: 34 lacking its signal sequence, e.g., for example between residues 20 and 620 of SEQ ID NO: 34).

A variant glucoamylase comprises at least one amino acid difference (substitution or addition) when compared to the amino acid sequence of the glucoamylase polypeptide of SEQ ID NO: 1, 3, 11, 13 or 27 to 36 and still exhibits glucoamylase activity. In an embodiment, the variant glucoamylase exhibits at least 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% of the activity of the native or wild-type glucoamylase having the amino acid sequence of SEQ ID NO: 1, 3, 11, 13 or 27 to 36. The glucoamylase variants also have at least 70%, 80%, 81%, 82%, 83%, 84%, 85%, 86%, 87%, 88%, 89%, 90%, 91%, 92%, 93%, 94%, 95%, 96%, 97%, 98% or 99% identity when compared to the wild-type or native glucoamylase having the amino acid sequence of SEQ ID NO: 1, 3, 11, 13 or 27 to 36 over its entire length. The term "percent identity", as known in the art, is a relationship between two or more polypeptide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, N Y (1988); Biocomputing: Informatics and Genome Projects (Smith, D. W., ed.) Academic Press, N Y (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant glucoamylases described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions are known in the art and are included herein. Non-conservative substitutions, such as replacing a basic amino acid with a hydrophobic one, are also well-known in the art.

A variant glucoamylase can also be a conservative variant or an allelic variant. As used herein, a conservative variant refers to alterations in the amino acid sequence that do not adversely affect the biological functions of the starch digesting glucoamylase. A substitution, insertion or deletion is said to adversely affect the polypeptide when the altered sequence prevents or disrupts a biological function associated with the starch digesting glucoamylase (e.g., the hydrolysis of starch into glucose). For example, the overall charge, structure or hydrophobic-hydrophilic properties of the polypeptide can be altered without adversely affecting a biological activity. Accordingly, the amino acid sequence can be altered, for example to render the peptide more hydrophobic or hydrophilic, without adversely affecting the biological activities of the starch digesting glucoamylase.

The present disclosure also provide fragments of the glucoamylase and glucoamylase variants described herein. A fragment comprises at least one less amino acid residue when compared to the amino acid sequence of the catalytic domain or the glucoamylase polypeptide or variant and still possess the enzymatic activity of the full-length glucoamylase. In an embodiment, the glucoamylase fragment exhibits at least 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% activity when compared to the full-length glucoamylase having the amino acid of SEQ ID NO: 1, 3, 11, 13 or 27 to 36 or variants thereof. The glucoamylase fragments can also have at least 70%, 80%, 81%, 82%, 83%, 84%, 85%, 86%, 87%, 88%, 89%, 90%, 91%, 92%, 93%, 94%, 95%, 96%, 97%, 98% or 99% identity when compared to the glucoamylase having the amino acid sequence of SEQ ID NO: 1, 3, 11, 13 or 27 to 36 or variants thereof. The fragment can be, for example, a truncation of one or more amino acid residues at the amino-terminus, the carboxy terminus or both termini of the starch digesting glucoamylase polypeptide or variant. In a specific embodiment, the fragment corresponds to a polypeptide of any one of SEQ ID NO: 27 to 36 to which the signal sequence has been removed. Alternatively or in combination, the fragment can be generated from removing one or more internal amino acid residues. In an embodiment, the glucoamylase fragment has at least 100, 150, 200, 250, 300, 350, 400, 450, 500, 550, 600 or more consecutive amino acids of the glucoamylase having the amino acid sequence of SEQ ID NO: 1, 3, 11, 13 or 27 to 36 or variants thereof.

The heterologous polypeptides having glucoamylase activity described herein are secreted polypeptides. In some embodiments, secreted heterologous polypeptides having glucoamylase activity are released in the culture/fermentation medium and do not remain physically attached to the recombinant yeast host cell. In alternative embodiments, the heterologous glucoamylases of the present disclosure can be secreted, but they remain physically associated with the recombinant yeast host cell. In an embodiment, at least one portion (usually at least one terminus) of the heterologous glucoamylase is bound, covalently, non-covalently and/or electrostatically for example, to the cell wall (and in some embodiments to the cytoplasmic membrane) of the recombinant yeast host cell. For example, the heterologous glucoamylase can be modified to bear one or more transmembrane domains, to have one or more lipid modifications (myristoylation, palmitoylation, farnesylation and/or prenylation), to interact with one or more membrane-associated polypeptide and/or to interactions with the cellular lipid rafts. While the heterologous glucoamylases may not be directly bound to the cell membrane or cell wall (e.g., such as when binding occurs via a tethering moiety), the polypeptide is nonetheless considered a "cell-associated" heterologous polypeptide according to the present disclosure.

In some embodiments, the heterologous glucoamylase can be expressed to be located at and associated to the cell wall of the recombinant yeast host cell. In some embodiments, the heterologous glucoamylase is expressed to be located at and associated to the external surface of the cell wall of the host cell. Recombinant yeast host cells all have a cell wall (which includes a cytoplasmic membrane) defining the intracellular (e.g., internally-facing the nucleus) and extracellular (e.g., externally-facing) environments. The heterologous glucoamylase can be located at (and in some embodiments, physically associated to) the external face of the recombinant yeast host's cell wall and, in further embodiments, to the external face of the recombinant yeast host's cytoplasmic membrane. In the context of the present disclosure, the expression "associated to the external face of the cell wall/cytoplasmic membrane of the recombinant yeast host cell" refers to the ability of the heterologous glucoamylase to physically integrate (in a covalent or non-covalent fashion), at least in part, in the cell wall (and in some embodiments in the cytoplasmic membrane) of the recombinant yeast host cell. The physical integration can be attributed to the presence of, for example, a transmembrane domain on the heterologous polypeptide, a domain capable of interacting with a cytoplasmic membrane polypeptide on the heterologous polypeptide, a post-translational modification made to the heterologous polypeptide (e.g., lipidation), etc.

In some circumstances, it may be warranted to increase or provide cell association to some heterologous glucoamylases because they exhibit insufficient intrinsic cell association or simply lack intrinsic cell association. In such embodiment, it is possible to provide the heterologous glucoamylase as a chimeric construct by combining it with a tethering amino acid moiety which will provide or increase attachment to the cell wall of the recombinant yeast host cell. In such embodiment, the chimeric heterologous polypeptide will be considered "tethered". It is preferred that the amino acid tethering moiety of the chimeric polypeptide be neutral with respect to the biological activity of the heterologous glucoamylase, e.g., does not interfere with the biological activity (such as, for example, the enzymatic activity) of the heterologous glucoamylase. In some embodiments, the association of the amino acid tethering moiety with the heterologous glucoamylase can increase the biological activity of the heterologous polypeptide (when compared to the non-tethered, "free" form).

In an embodiment, a tethering moiety can be used to be expressed with the heterologous glucoamylase to locate the heterologous polypeptide to the wall of the recombinant yeast host cell. Various tethering amino acid moieties are known in art and can be used in the chimeric polypeptides of the present disclosure. The tethering moiety can be a transmembrane domain found on another polypeptide and allow the chimeric polypeptide to have a transmembrane domain. In such embodiment, the tethering moiety can be derived from the FLO1 polypeptide. In still another example, the amino acid tethering moiety can be modified post-translation to include a glycosylphosphatidylinositol (GPI) anchor and allow the chimeric polypeptide to have a GPI anchor. GPI anchors are glycolipids attached to the terminus of a polypeptide (and in some embodiments, to the carboxyl terminus of a polypeptide) which allows the anchoring of the polypeptide to the cytoplasmic membrane of the cell membrane. Tethering amino acid moieties capable of providing a GPI anchor include, but are not limited to those associated with/derived from a SED1 polypeptide, a TIR1 polypeptide, a CWP2 polypeptide, a CCW12 polypeptide, a SPI1 polypeptide, a PST1 polypeptide or a combination of a AGA1 and a AGA2 polypeptide. In an embodiment, the tethering moiety provides a GPI anchor and, in still a further embodiment, the tethering moiety is derived from the SPI1 polypeptide or the CCW12 polypeptide.

The tethering amino acid moiety can be a variant of a known/native tethering amino acid moiety. The tethering amino acid moiety can be a fragment of a known/native tethering amino acid moiety or fragment of a variant of a known/native tethering amino acid moiety.

In embodiments in which an amino acid tethering moiety and/or signal sequence may be desirable, the heterologous polypeptide can be provided as a chimeric polypeptide expressed by the recombinant yeast host cell and having one of the following formulae:

(NH₂)SS-HP-L-TT(COOH)  (I) or

(NH₂)SS-TT-L-HP(COOH)  (II)

In both of these formulae, the residue "HP" refers to a heterologous polypeptide moiety, the residue "SS" refers to the signal sequence (which cannot have the amino acid sequence of SEQ ID NO: 5), the residue "L" refers to the presence of an optional linker, and the residue "TT" refers to an optional amino acid tethering moiety. In the chimeric polypeptides of formula (I), the amino (NH₂ or N) terminus of the amino acid tether is located (directly or indirectly) at the carboxyl (COOH or C) terminus of the heterologous glucoamylase moiety. In the chimeric polypeptides of formula (I), the amino (NH₂ or N) terminus of the heterologous glucoamylase moiety is located (directly or indirectly) at the carboxyl (COOH or C) terminus of the signal sequence. In the chimeric polypeptides of formula (II), the carboxy (COOH or C) terminus of the amino acid tether is located (directly or indirectly) at the amino (NH₂ or N) terminus of the heterologous glucoamylase moiety. In the chimeric polypeptides of formula (II), the carboxy (COOH or C) terminus of signal sequence is located (directly or indirectly) at the amino (NH₂ or N) terminus of the amino acid tether. Embodiments of chimeric tethered heterologous polypeptides have been disclosed in WO2018/167670 and are included herein in their entirety.

The heterologous nucleic acid molecule can include a third polynucleotide including a promoter capable of controlling the expression of the first and second polynucleotide. In such embodiment, the promoter and the polynucleotide coding for the signal sequence and the heterologous polypeptide are operatively linked to one another. In the context of the present disclosure, the expressions "operatively linked" or "operatively associated" refers to fact that the promoter is physically associated to the first and second polynucleotide in a manner that allows, under certain conditions, for expression of the heterologous polypeptide from the heterologous nucleic acid molecule. In an embodiment, the promoter can be located upstream (5') of the nucleic acid sequence coding for the heterologous polypeptide. In still another embodiment, the promoter can be located downstream (3') of the nucleic acid sequence coding for the heterologous polypeptide. In the context of the present disclosure, one or more than one promoter can be included in the nucleic acid molecule. When more than one promoter is included in the nucleic acid molecule, each of the promoters is operatively linked to the nucleic acid sequence coding for the polypeptide. The promoters can be located, in view of the nucleic acid molecule coding for the polypeptide, upstream, downstream as well as both upstream and downstream.

"Promoter" refers to a DNA fragment capable of controlling the expression of a coding sequence or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as polypeptide binding domains (consensus sequences) responsible for the binding of the polymerase.

The promoter can be heterologous to the nucleic acid molecule encoding the heterologous polypeptide. The promoter can be heterologous or derived from a strain being from the same genus or species as the recombinant host cell. In an embodiment, the promoter is derived from the same genus or species of the yeast host cell and the polypeptide is derived from different genera that the host cell. One or more promoters can be used to allow the expression of the polypeptides in the recombinant yeast host cell.

In some embodiments, the recombinant yeast host cell is a facultative anaerobe, such as *Saccharomyces cerevisiae*. For facultative anaerobes, cells tend to propagate or ferment depending on the availability of oxygen. In a fermentation process, yeast cells are generally allowed to propagate before fermentation is conducted. In some embodiments, the promoter preferentially initiates transcription during a propagation phase such that the heterologous polypeptides (variants or fragments) are expressed during the propagation phase. As used in the context of the present disclosure, the expression "propagation phase" refers to an expansion phase of a commercial process in which the yeasts are propagated under aerobic conditions. In some instances, the propagated biomass can be used in a following fermenting step (e.g. under anaerobic conditions) to maximize the production of one or more desired metabolites or fermentation products.

The heterologous nucleic acid molecule can include a promoter (or a combination of promoters) capable of allowing the expression of the heterologous polypeptide during propagation (and optionally during fermentation). This embodiment will allow the accumulation of the polypeptide associated with the recombinant yeast host cell prior to any subsequent use, for example in liquefaction or fermentation. In some embodiments, the promoter substantially limits the expression of the polypeptide during the propagation phase.

The expression of the polypeptides during the propagation phase may provide sufficient expression such that the polypeptide or the recombinant yeast cells may be added during the liquefaction of starch, thereby providing yeast cells with sufficient nutrients to undergo metabolic processing. The promoters can be native or heterologous to the heterologous gene encoding the heterologous polypeptide. The promoters that can be included in the heterologous nucleic acid molecule can be constitutive or inducible promoters. Constitutive promoters include, but are not limited to, tef2p (e.g., the promoter of the tef2 gene, a variant thereof or a fragment thereof), cwp2p (e.g., the promoter of the cwp2 gene, a variant thereof or a fragment thereof), ssa1p (e.g., the promoter of the ssa1 gene, a variant thereof), eno1p (e.g., the promoter of the eno1 gene, variant thereof or a fragment thereof), hxk1 (e.g., the promoter of the hxk1 gene, a variant thereof or a fragment thereof) and/or pgk1p (e.g., the promoter of the pgk1 gene, a variant thereof or a fragment thereof). Inducible promoters include, but are not limited to glucose-regulated promoters (e.g., the promoter of the hxt7 gene (referred to as hxt7p), a functional variant or a functional fragment thereof; the promoter of the ctt1 gene (referred to as ctt1p), a functional variant or a functional fragment thereof; the promoter of the glo1 gene (referred to as glo1p), a functional variant or a functional fragment thereof; the promoter of the ygp1 gene (referred to as ygp1p), a functional variant or a functional fragment thereof; the promoter of the gsy2 gene (referred to as gsy2p), a functional variant or a functional fragment thereof), molasses-regulated promoters (e.g., the promoter of the mol1 gene (referred to as mol1p), a functional variant or a functional fragment thereof), heat shock-regulated promoters (e.g., the promoter of the glo1 gene (referred to as glo1p), a functional variant or a functional fragment thereof; the promoter of the sti1 gene (referred to as sti1p), a functional variant or a functional fragment thereof; the promoter of the ygp1 gene (referred to as ygp1p), a functional variant or a functional fragment thereof; the promoter of the gsy2 gene (referred to as gsy2p), a functional variant or a functional fragment thereof), oxidative stress response promoters (e.g., the promoter of the cup1 gene (referred to as cup1p), a functional variant or a functional fragment thereof; the promoter of the ctt1 gene (referred to as ctt1p), a functional variant or a functional fragment thereof; the promoter of the trx2 gene (referred to as trx2p), a functional variant or a functional fragment thereof; the promoter of the gpd1 gene (referred to as gpd1p), a functional variant or a functional fragment thereof; the promoter of the hsp12 gene (referred to as hsp12p), a functional variant or a functional fragment thereof), osmotic stress response promoters (e.g., the promoter of the ctt1 gene (referred to as ctt1p), a functional variant or a functional fragment thereof; the promoter of the glo1 gene (referred to as glo1p), a functional variant or a functional fragment thereof; the promoter of the gpd1 gene (referred to as gpd1p), a functional variant or a functional fragment thereof; the promoter of the ygp1 gene (referred to as ygp1p), a functional variant or a functional fragment thereof), nitrogen-regulated promoters (e.g., the promoter of the ygp1 gene (referred to as ygp1p), a functional variant or a functional fragment thereof) and the promoter of the adh1 gene (referred to as adh1p), a functional variant or a functional fragment thereof) and/or a molasses-regulated promoter (e.g., the promoter of the tir1 gene (referred to as tir1p), a functional variant or a functional fragment thereof).

Promoters that can be included in the heterologous nucleic acid molecule of the present disclosure include, without limitation, the promoter of the tdh1 gene (referred to as tdh1p, a functional variant or a functional fragment thereof), of the hor7 gene (referred to as hor7p, a functional variant or a functional fragment thereof), of the hsp150 gene (referred to as hsp150p, a functional variant or a functional fragment thereof), of the hxt7 gene (referred to as hxt7p, a functional variant or a functional fragment thereof), of the gpm1 gene (referred to as gpm1p, a functional variant or a functional fragment thereof), of the pgk1 gene (referred to as pgk1p, a functional variant or a functional fragment thereof), of the stl1 gene (referred to as stl1p, a functional variant or a functional fragment thereof) and/or of the tef2 gen (referred to as tef2p, a functional variant or a functional fragment thereof). In an embodiment, the promoter is or comprises the tef2p. In still another embodiment, the promoter comprises or consists essentially of the tdh1p and the hor7p. In a further embodiment, the promoter is the thd1p. In another embodiment, the promoter is the adh1p.

In the context of the present disclosure, the expression "functional fragment of a promoter" when used in combination to a promoter refers to a shorter nucleic acid sequence than the native promoter which retain the ability to control the expression of the nucleic acid sequence encoding the polypeptides during the propagation phase of the recombinant yeast host cells. Usually, functional fragments are either 5' and/or 3' truncation of one or more nucleic acid residue from the native promoter nucleic acid sequence.

In some embodiments, the heterologous nucleic acid molecules include one or a combination of terminator sequence(s) to end the translation of the heterologous polypeptide (or of the chimeric polypeptide comprising same).

The terminator can be native or heterologous to the nucleic acid sequence encoding the heterologous polypeptide or its corresponding chimera. In some embodiments, one or more terminators can be used. In some embodiments, the terminator comprises the terminator derived from is from the dit1 gene (dit1t, a functional variant or a functional fragment thereof), from the idp1 gene (idp1t, a functional variant or a functional fragment thereof), from the gpm1 gene (gpm1t, a functional variant or a functional fragment thereof), from the pma1 gene (pam1t, a functional variant or a functional fragment thereof), from the tdh3 gene (tdh3t, a functional variant or a functional fragment thereof), from the hxt2 gene (a functional variant or a functional fragment thereof), from the adh3 gene (adh3t, a functional variant or a functional fragment thereof), and/or from the ira2 gene (ira2t, a functional variant or a functional fragment thereof). In an embodiment, the terminator comprises or is derived from the dit1 gene (dit1t, a functional variant or a functional fragment thereof). In another embodiment, the terminator comprises or is derived adh3t and/or idp1t. In the context of the present disclosure, the expression "functional variant of a terminator" refers to a nucleic acid sequence that has been substituted in at least one nucleic acid position when compared to the native terminator which retain the ability to end the expression of the nucleic acid sequence coding for the heterologous polypeptide or its corresponding chimera. In the context of the present disclosure, the expression "functional fragment of a terminator" refers to a shorter nucleic acid sequence than the native terminator which retain the ability to end the expression of the nucleic acid sequence coding for the heterologous polypeptide or its corresponding chimera.

In some embodiments, the recombinant host cell comprises a genetic modification (e.g., one or more heterologous nucleic acid molecule) allowing the recombinant expression of the polypeptide having starch digesting glucoamylase activity. In such embodiment, a heterologous nucleic acid molecule encoding the polypeptide having starch digesting glucoamylase activity can be introduced in the recombinant host to express the polypeptide having starch digesting glucoamylase activity. The expression of the polypeptide having starch digesting glucoamylase activity can be constitutive or induced.

In some embodiments, the recombinant host cell comprises a further genetic modification (e.g., the introduction of one or more heterologous nucleic acid molecule) allowing the recombinant expression of the polypeptide having starch digesting alpha-amylase activity. In such embodiment, a heterologous nucleic acid molecule encoding the polypeptide having starch digesting alpha-amylase activity can be introduced in the recombinant host to express the polypeptide having starch digesting alpha-amylase activity activity. The expression of the polypeptide having starch digesting alpha-amylase activity can be constitutive or induced. For example, the heterologous alpha-amylase can be from a *Rhizomucor* sp., such as, for example, from *Rhizomucor pusillus*. In an embodiment, the heterologous alpha-amylase corresponds to Uniprot M9T189. In another embodiment, the heterologous alpha-amylase can have the amino acid sequence of SEQ ID NO: 17, be a variant of the amino acid sequence of SEQ ID NO: 17 having alpha-amylase activity or be a fragment of the amino acid sequence of SEQ ID NO: 17 having alpha-amylase activity (which can, in an embodiment, correspond to a fragment of the amino acid sequence of SEQ ID NO: 17 lacking its signal sequence, e.g., for example, between residues 22 and 471 of SEQ ID NO: 17). For example, the heterologous alpha-amylase can be from a *Aspergillus* sp., such as, for example, from *Aspergillus luchuensis*. In an embodiment, the heterologous alpha-amylase corresponds to Uniprot A0A146F6W4 or to GenBank Accession Number GAT21778. In another embodiment, the heterologous alpha-amylase can have the amino acid sequence of SEQ ID NO: 18, be a variant of the amino acid sequence of SEQ ID NO: 18 having alpha-amylase activity or be a fragment of the amino acid sequence of SEQ ID NO: 18 having alpha-amylase activity (which can, in an embodiment, correspond to a fragment of the amino acid sequence of SEQ ID NO: 18 lacking its signal sequence, e.g., for example, between residues 22 to 615 of SEQ ID NO: 18). In an embodiment, the heterologous alpha-amylase corresponds to Uniprot O13296 or to GenBank Accession Number BAA22993. In another embodiment, the heterologous alpha-amylase can have the amino acid sequence of SEQ ID NO: 26, be a variant of the amino acid sequence of SEQ ID NO: 26 having alpha-amylase activity or be a fragment of the amino acid sequence of SEQ ID NO: 26 having alpha-amylase activity (which can, in an embodiment, correspond to a fragment of the amino acid sequence of SEQ ID NO: 26 lacking its signal sequence, e.g., for example between residues 22 to 640 of SEQ ID NO: 26). For example, the heterologous alpha-amylase can be from *Aspergillus oryzae*. In an embodiment, the heterologous alpha-amylase corresponds to Uniprot Q2UIS5 or to GenBank Accession Number XP_001820542. In another embodiment, the heterologous alpha-amylase can have the amino acid sequence of SEQ ID NO: 19, be a variant of the amino acid sequence of SEQ ID NO: 19 having alpha-amylase activity or be a fragment of the amino acid sequence of SEQ ID NO: 19 having alpha-amylase activity (which can, in an embodiment, correspond to a fragment of the amino acid sequence of SEQ ID NO: 19 lacking its signal sequence, e.g., for example between residues 24 to 549 of SEQ ID NO: 19). For example, the heterologous alpha-amylase can be from *Aspergillus niger*. In an embodiment, the heterologous alpha-amylase corresponds to Uniprot A2QTS4 or to GenBank Accession Number XP_001393626. In another embodiment, the heterologous alpha-amylase can have the amino acid sequence of SEQ ID NO: 21, be a variant of the amino acid sequence of SEQ ID NO: 21 having alpha-amylase activity or be a fragment of the amino acid sequence of SEQ ID NO: 21 having alpha-amylase activity (which can, in an embodiment, correspond to a fragment of the amino acid sequence of SEQ ID NO: 21 lacking its signal sequence, e.g., for example between residues 26 to 555 of SEQ ID NO: 21). In an embodiment, the heterologous alpha-amylase corresponds to Uniprot A2R6F9 or to GenBank Accession Number XP_001397301. In another embodiment, the heterologous alpha-amylase can have the amino acid sequence of SEQ ID NO: 22, be a variant of the amino acid sequence of SEQ ID NO: 22 having alpha-amylase activity or be a fragment of the amino acid sequence of SEQ ID NO: 22 having alpha-amylase activity (which can, in an embodiment, correspond to a fragment of the amino acid sequence of SEQ ID NO: 22 lacking its signal sequence, e.g., for example between residues 23 and 567 of SEQ ID NO: 22). In an embodiment, the heterologous alpha-amylase corresponds to GenBank Accession Number XP_001395328. In another embodiment, the heterologous alpha-amylase can have the amino acid sequence of SEQ ID NO: 23, be a variant of the amino acid sequence of SEQ ID NO: 23 having alpha-amylase activity or be a fragment of the amino acid sequence of SEQ ID NO: 23 having alpha-amylase activity (which can, in an embodiment, correspond to a fragment of the amino acid sequence of SEQ ID NO: 23 lacking its signal sequence, e.g., for example between residues 30 and 550 of SEQ ID NO: 23). In an embodiment, the heterologous alpha-amylase corresponds to Uniprot A0A370BQ30 or to GenBank Accession Number RDH15462. In another embodiment, the heterologous alpha-amylase can have the amino acid sequence of SEQ ID NO: 24, be a variant of the amino acid sequence of SEQ ID NO: 24 having alpha-amylase activity or be a fragment of the amino acid sequence of SEQ ID NO: 24 having alpha-amylase activity (which can, in an embodiment, correspond to a fragment of the amino acid sequence of SEQ ID NO: 24 lacking its signal sequence, e.g., for example between residues 17 and 524 of SEQ ID NO: 24). For example, the heterologous alpha-amylase can be from *Aspergillus fischeri*. In an embodiment, the heterologous alpha-amylase corresponds to Uniprot A1CYB1 or to GenBank Accession Number XP_001265628. In another embodiment, the heterologous alpha-amylase can have the amino acid sequence of SEQ ID NO: 25, be a variant of the amino acid sequence of SEQ ID NO: 25 having alpha-amylase activity or be a fragment of the amino acid sequence of SEQ ID NO: 25 having alpha-amylase activity (which can, in an embodiment, correspond to a fragment of the amino acid sequence of SEQ ID NO: 25 lacking its signal sequence, e.g., for example between residues 24 to 632 of SEQ ID NO: 25). For example, the heterologous alpha-amylase can be from a *Homo* sp., such as, for example, from *Homo sapiens*. In an embodiment, the heterologous alpha-amylase corresponds to GenBank Accession Number 1B2Y_A. In another embodiment, the heterologous alpha-amylase can have the amino acid sequence of SEQ ID NO: 20, be a variant of the amino acid sequence of SEQ ID NO: 20 having alpha-amylase activity or be a fragment of the amino acid sequence of SEQ ID NO: 20 having alpha-amylase activity (which can, in an embodiment, correspond to a fragment of the amino acid sequence of SEQ ID NO: 20 lacking its signal sequence, e.g., for example between residues 20 to 515 of SEQ ID NO: 20).

A variant alpha-amylase comprises at least one amino acid difference (substitution or addition) when compared to the amino acid sequence of the alpha-amylase polypeptide of SEQ ID NO: 17 to 26 and still exhibits alpha-amylase activity. In an embodiment, the variant alpha-amylase exhibits at least 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% of the activity of the native or wild-type alpha-amylase having the amino acid sequence of SEQ ID NO: 17 to 26. The alpha-amylase variants also have at least 70%, 80%, 81%, 82%, 83%, 84%, 85%, 86%, 87%, 88%, 89%, 90%, 91%, 92%, 93%, 94%, 95%, 96%, 97%, 98% or 99% identity when compared to the wild-type or native alpha-amylase having the amino acid sequence of SEQ ID NO: 17 to 26 over its entire length. The term "percent identity", as known in the art, is a relationship between two or more polypeptide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, N Y (1988); Biocomputing: Informatics and Genome Projects (Smith, D. W., ed.) Academic Press, N Y (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant alpha-amylases described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions are known in the art and are included herein. Non-conservative substitutions, such as replacing a basic amino acid with a hydrophobic one, are also well-known in the art.

A variant alpha-amylase can also be a conservative variant or an allelic variant. As used herein, a conservative variant refers to alterations in the amino acid sequence that do not adversely affect the biological functions of the starch digesting alpha-amylase. A substitution, insertion or deletion is said to adversely affect the polypeptide when the altered sequence prevents or disrupts a biological function associated with the starch digesting alpha-amylase (e.g., the hydrolysis of starch into glucose). For example, the overall charge, structure or hydrophobic-hydrophilic properties of the polypeptide can be altered without adversely affecting a biological activity. Accordingly, the amino acid sequence can be altered, for example to render the peptide more hydrophobic or hydrophilic, without adversely affecting the biological activities of the starch digesting alpha-amylase.

The present disclosure also provide fragments of the alpha-amylases and alpha-amylases variants described herein. A fragment comprises at least one less amino acid residue when compared to the amino acid sequence of the catalytic domain or the alpha-amylase polypeptide or variant and still possess the enzymatic activity of the full-length alpha-amylase. In an embodiment, the alpha-amylase fragment exhibits at least 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% activity when compared to the full-length alpha-amylase having the amino acid of SEQ ID NO: 17 to 26 or variants thereof. The alpha-amylase fragments can also have at least 70%, 80%, 81%, 82%, 83%, 84%, 85%, 86%, 87%, 88%, 89%, 90%, 91%, 92%, 93%, 94%, 95%, 96%, 97%, 98% or 99% identity when compared to the alpha-amylase having the amino acid sequence of SEQ ID NO: 17 to 26 or variants thereof. The fragment can be, for example, a truncation of one or more amino acid residues at the amino-terminus, the carboxy terminus or both termini of the starch digesting alpha-amylase or variant. In a specific embodiment, the fragment corresponds to a polypeptide of any one of SEQ ID NO: 17 to 26 to which the signal sequence has been removed. Alternatively or in combination, the fragment can be generated from removing one or more internal amino acid residues. In an embodiment, the alpha-amylase fragment has at least 100, 150, 200, 250, 300, 350, 400, 450, 500, 550, 600 or more consecutive amino acids of the alpha-amylase having the amino acid sequence of SEQ ID NO: 17 to 26 or variants thereof.

The alpha-amylase can be expressed using its native signal sequence or can be expressed using a heterologous signal sequence. In embodiments the heterologous signal sequence associated with the alpha-amylase can have the amino acid sequence of SEQ ID NO: 5 or the section spanning residues 1 to 21 of SEQ ID NO: 17, 1 to 21 of SEQ ID NO: 18, 1 to 23 of SEQ ID NO: 19, 1 to 19 of SEQ ID NO: 20, 1 to 25 of SEQ ID NO: 21, 1 to 22 of SEQ ID NO: 22, 1 to 29 of SEQ ID NO: 23, 1 to 16 of SEQ ID NO: 24, 1 to 23 of SEQ ID NO: 25, 1 to 21 of SEQ ID NO: 26, 1 to 17 of SEQ ID NO: 27, 1 to 20 of SEQ ID NO: 28, 1 to 22 of SEQ ID NO: 29, 1 to 18 of SEQ ID NO: 30, 1 to 25 of SEQ ID NO: 31, 1 to 19 of SEQ ID NO: 32, 1 to 18 of SEQ ID NO: 33, 1 to 19 of SEQ ID NO: 34, 1 to 18 of SEQ ID NO: 35, 1 to 18 of SEQ ID NO: 36 as well as variants and fragments thereof.

Process for Saccharification and Fermentation of a Biomass

The recombinant yeast host cells described herein can be used in saccharification for improving the hydrolysis of a biomass and, in some embodiments, the production of a fermentation product from the biomass. In some embodiments, the recombinant yeast host cells of the present disclosure maintain their robustness during saccharification and fermentation in the presence of a stressor such as, for example, lactic acid, formic acid and/or a bacterial contamination (that can be associated, in some embodiments, with an increase in lactic acid during fermentation), a decrease in pH, a reduction in aeration, elevated temperatures or a combination of these conditions.

The fermented product intended to be obtained during the fermentation can be an alcohol, such as, for example, ethanol, isopropanol, n-propanol, 1-butanol, methanol, acetone, 1,3-propanediol and/or 1,2-propanediol. In an embodiment, the fermented product is ethanol.

In the process, the biomass that can be hydrolyzed (and optionally fermented) with the recombinant yeast host cells. Such biomass includes any type of biomass known in the art and described herein. For example, the biomass can include, but is not limited to, starch, sugar and lignocellulosic materials. Starch materials can include, but are not limited to, mashes such as corn, wheat, rye, barley, rice, or milo. Sugar materials can include, but are not limited to, sugar beets, artichoke tubers, sweet sorghum, molasses or cane. The terms "lignocellulosic material", "lignocellulosic substrate" and "cellulosic biomass" mean any type of substrate comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, waste-water-treatment sludge, municipal solid waste, corn fiber from wet and dry mill corn ethanol plants and sugar-processing residues. The terms "hemicellulosics", "hemicellulosic portions" and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan and galactoglucomannan), pectins (e.g., homogalacturonans, rhamnogalacturonan I and II, and xylogalacturonan) and proteoglycans (e.g., arabinogalactan-polypeptide, extensin, and pro line-rich polypeptides).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASO), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, molasses, sugarcane, leaves, agricultural and forestry residues, grasses such as switchgrass, ruminant digestion products, municipal wastes, paper mill effluent, newspaper, cardboard or combinations thereof.

Paper sludge is also a viable feedstock for lactate or acetate production. Paper sludge is solid residue arising from pulping and paper-making, and is typically removed from process wastewater in a primary clarifier. The cost of disposing of wet sludge is a significant incentive to convert the material for other uses, such as conversion to ethanol. Processes provided by the present invention are widely applicable. Moreover, the hydrolyzed biomass may be used to produce ethanol or higher value added chemicals, such as organic acids, aromatics, esters, acetone and polymer intermediates.

The process of the present disclosure comprise contacting the recombinant host cells comprising the heterologous polypeptide having glucoamylase activity described herein with a biomass so as to allow the hydrolysis of at least a part of the biomass and the conversion of the biomass (at least in part) into a fermentation product (e.g., an alcohol such as ethanol). In some embodiments, the biomass to be hydrolyzed/fermented is a lignocellulosic biomass and, in some embodiments, it comprises starch (in a gelatinized or raw form). In an embodiment, the biomass to be hydrolyzed/fermented is raw starch. In other embodiments, the biomass to be hydrolyzed/fermented is derived from corn, potato, cassava, rice, or buckwheat. In preferred embodiments, the biomass is derived from corn, such as in the form of corn mash. The process can include, in some embodiments, heating the lignocellulosic biomass prior to fermentation to provide starch in a gelatinized form. In another embodiment, the biomass comprises or is derived from sugar cane.

The fermentation process can be performed at temperatures of at least about 20° C., about 21° C., about 22° C., about 23° C., about 24° C., about 25° C., about 26° C., about 27° C., about 28° C., about 29° C., about 30° C., about 31° C., about 32° C., about 33°, about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments, the production of ethanol from cellulose can be performed, for example, at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C. In some embodiments, the recombinant microbial host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the liquefaction of starch occurs in the presence of recombinant yeast host cells described herein. In some embodiments, the liquefaction of starch is maintained at a temperature of between about 70° C.-105° C. to allow for proper gelatinization and hydrolysis of the starch. In an embodiment, the liquefaction occurs at a temperature of at least about 70° C., 75° C., 80° C., 85° C., 90° C., 95° C., 100° C. or 105° C. Alternatively or in combination, the liquefaction occurs at a temperate of no more than about 105° C., 100° C., 95° C., 90° C., 85° C., 80° C., 75° C. or 70° C. In yet another embodiment, the liquefaction occurs at a temperature between about 80° C. and 85° C. (which can include a thermal treatment spike at 105° C.).

In some embodiments, the process can be used to produce ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, at least about 500 mg per hour per liter, at least about 600 mg per hour per liter, at least about 700 mg per hour per liter, at least about 800 mg per hour per liter, at least about 900 mg per hour per liter, at least about 1 g per hour per liter, at least about 1.5 g per hour per liter, at least about 2 g per hour per liter, at least about 2.5 g per hour per liter, at least about 3 g per hour per liter, at least about 3.5 g per hour per liter, at least about 4 g per hour per liter, at least about 4.5 g per hour per liter, at least about 5 g per hour per liter, at least about 5.5 g per hour per liter, at least about 6 g per hour per liter, at least about 6.5 g per hour per liter, at least about 7 g per hour per liter, at least about 7.5 g per hour per liter, at least about 8 g per hour per liter, at least about 8.5 g per hour per liter, at least about 9 g per hour per liter, at least about 9.5 g per hour per liter, at least about 10 g per hour per liter, at least about 10.5 g per hour per liter, at least about 11 g per hour per liter, at least about 11.5 g per hour per liter, at least about 12 g per hour per liter, at least about 12.5 g per hour per liter, at least about 13 g per hour per liter, at least about 13.5 g per hour per liter, at least about 14 g per hour per liter, at least about 14.5 g per hour per liter or at least about 15 g per hour per liter.

Ethanol production can be measured using any method known in the art. For example, the quantity of ethanol in fermentation samples can be assessed using HPLC analysis. Many ethanol assay kits are commercially available that use, for example, alcohol oxidase enzyme based assays.

In some embodiments, the process can be used in the presence of a stressor such as low pH. For example, the stressor is a pH of 7.0 or lower, 6.5 or lower, 6.0 or lower, 5.5 or lower, 5.0 or lower, 4.8 or lower, 4.6 or lower, 4.4 or lower, 4.2 or lower, 4.0 or lower, 3.8 or lower, 3.6 or lower, 3.4 or lower, 3.2 or lower, or 3.0 or lower.

As shown in the Examples, recombinant yeast host cells expressing the heterologous glucoamylase exhibits enhanced robustness compared to yeast host cells expressing other known glucoamylases. In specific embodiments of a recombinant yeast host cell expressing a heterologous glucoamylase, fermentation with the recombinant yeast cell yielded higher ethanol titers than recombinant yeast host cells expressing other heterologous glucoamylases. In some embodiments, the recombinant yeast host cell expressing heterologous glucoamylase yielded greater than 10 mg/L increase, greater than 25 mg/L increase, greater than 50 mg/L increase, greater than 100 mg/L increase, greater than 200 mg/L increase, greater than 300 mg/L increase, greater than 400 mg/L increase, greater than 500 mg/L increase, greater than 600 mg/L increase, greater than 700 mg/L increase, greater than 800 mg/L increase, greater than 900 mg/L increase, or greater than 1 g/L increase) in ethanol production at low pH values and in corn fermentation when compared to recombinant yeast host cells expressing other heterologous glucoamylases.

In the process described herein, it is possible to add an exogenous source (e.g., to dose) of an enzyme to facilitate saccharification or improve fermentation yield. As such, the process can comprise including one or more dose(s) of one or more enzyme(s) during the saccharification and/or the fermentation step. The exogenous enzyme that can be used during the saccharification/fermentation process can include, without limitation, an alpha-amylase, a glucoamylase, a protease, a phytase, a pullulanase, a cellulase, a hemi-cellulase such as a xylanase, a trehalase, or any combination thereof. The exogenous enzyme can be provided, in some embodiments, in a purified form and/or provided as part of a cocktail.

The process of the present disclosure can include a step of adding a dose (or multiple doses) of an exogenous enzyme (which may be purified) to increase the fermentation yield or allow the yeast to complete the fermentation. In such embodiment, the requirement to add one or more dose(s) can be determined prior to or during fermentation.

For example, the exogenous glucoamylase can be from a *Gloeophyllum* sp., such as, for example, from *Gloeophyllum trabeum*. In an embodiment, the exogenous glucoamylase corresponds to Uniprot S7Q4V9 or GenBank Accession Number_007866834. In another embodiment, the exogenous glucoamylase can have the amino acid sequence of SEQ ID NO: 27, be a variant of the amino acid sequence of SEQ ID NO: 27 having glucoamylase activity or be a fragment of the amino acid sequence of SEQ ID NO: 27 having glucoamylase activity (which can, in an embodiment, correspond to a fragment of the amino acid sequence of SEQ ID NO: 27 lacking its signal sequence, e.g., for example between residues 18 to 576 of SEQ ID NO: 27). For example, the exogenous glucoamylase can be from a *Trichoderma* sp., such as, for example, from *Trichoderma reesii*. In an embodiment, the exogenous glucoamylase corresponds to Uniprot G0R866 or GenBank Accession Number_ XP_006960925. In another embodiment, the exogenous glucoamylase can have the amino acid sequence of SEQ ID NO: 28, be a variant of the amino acid sequence of SEQ ID NO: 28 having glucoamylase activity or be a fragment of the amino acid sequence of SEQ ID NO: 28 having glucoamylase activity (which can, in an embodiment, correspond to a fragment of the amino acid sequence of SEQ ID NO: 28 lacking its signal sequence, e.g., for example between residues 21 to 632 of SEQ ID NO: 28). For example, the exogenous glucoamylase can be from a *Trametes* sp., such as, for example, from *Trametes cingulata*. In another embodiment, the exogenous glucoamylase can have the amino acid sequence of SEQ ID NO: 29, be a variant of the amino acid sequence of SEQ ID NO: 29 having glucoamylase activity or be a fragment of the amino acid sequence of SEQ ID NO: 29 having glucoamylase activity (which can, in an embodiment, correspond to a fragment of the amino acid sequence of SEQ ID NO: 29 lacking its signal sequence, e.g., for example between residues 23 to 574 of SEQ ID NO: 29). For example, the exogenous glucoamylase can be from a *Athelia* sp., such as, for example, from *Athelia rolfsil*. In an embodiment, the exogenous glucoamylase corresponds to Uniprot Q12596 or GenBank Accession Number_ BAA08436. In another embodiment, the exogenous glucoamylase can have the amino acid sequence of SEQ ID NO: 30, be a variant of the amino acid sequence of SEQ ID NO: 30 having glucoamylase activity or be a fragment of the amino acid sequence of SEQ ID NO: 30 having glucoamylase activity (which can, in an embodiment, correspond to a fragment of the amino acid sequence of SEQ ID NO: 30 lacking its signal sequence, e.g., for example between residues 19 to 579 of SEQ ID NO: 30). For example, the exogenous glucoamylase can be from a *Rhizopus* sp., such as, for example, from *Rhizopus oryzae*. In an embodiment, the exogenous glucoamylase corresponds to Uniprot P07683 or GenBank Accession Number P07683. In another embodiment, the exogenous glucoamylase can have the amino acid sequence of SEQ ID NO: 31, be a variant of the amino acid sequence of SEQ ID NO: 31 having glucoamylase activity or be a fragment of the amino acid sequence of SEQ ID NO: 31 having glucoamylase activity (which can, in an embodiment, correspond to a fragment of the amino acid sequence of SEQ ID NO: 31 lacking its signal sequence, e.g., for example, between residues 26 and 604 of SEQ ID NO: 31). For example, the exogenous glucoamylase can be from a *Aspergillus* sp., such as, for example, from *Aspergillus oryzae*. In an embodiment, the exogenous glucoamylase corresponds to Uniprot P36914 or GenBank Accession Number BAA00841. In another embodiment, the exogenous glucoamylase can have the amino acid sequence of SEQ ID NO: 32, be a variant of the amino acid sequence of SEQ ID NO: 32 having glucoamylase activity or be a fragment of the amino acid sequence of SEQ ID NO: 32 having glucoamylase activity (which can, in an embodiment, correspond to a fragment of the amino acid sequence of SEQ ID NO: 32 lacking its signal sequence, e.g., for example between residues 20 to 612 of SEQ ID NO: 32). In yet another example, the exogenous glucoamylase can be from *Aspergillus awamori*. In an embodiment, the exogenous glucoamylase corresponds to Uniprot Q76L97 or GenBank Accession Number BAD06004. In another embodiment, the exogenous glucoamylase can have the amino acid sequence of SEQ ID NO: 35, be a variant of the amino acid sequence of SEQ ID NO: 35 having glucoamylase activity or be a fragment of the amino acid sequence of SEQ ID NO: 35 having glucoamylase activity (which can, in an embodiment, correspond to a fragment of the amino acid sequence of SEQ ID NO: 35 lacking its signal sequence, e.g., for example between residues 19 to 639 of SEQ ID NO: 35). In yet another example, the exogenous glucoamylase can be from *Aspergillus niger*. In an embodiment, the exogenous glucoamylase corresponds to Uniprot Q870G8 or GenBank Accession Number AAP04499. In another embodiment, the exogenous glucoamylase can have the amino acid sequence of SEQ ID NO: 36, be a variant of the amino acid sequence of SEQ ID NO: 36 having glucoamylase activity or be a fragment of the amino acid sequence of SEQ ID NO: 36 having glucoamylase activity (which can, in an embodiment, correspond to a fragment of the amino acid sequence of SEQ ID NO: 36 lacking its signal sequence, e.g., for example between residues 19 to 639 of SEQ ID NO: 36). For example, the exogenous glucoamylase can be from a *Ophiostoma* sp., such as, for example, from *Ophiostoma floccosum*. In an embodiment, the exogenous glucoamylase corresponds to Uniprot Q06SN2 or GenBank Accession Number ABF72529. In another embodiment, the exogenous glucoamylase can have the amino acid sequence of SEQ ID NO: 33, be a variant of the amino acid sequence of SEQ ID NO: 33 having glucoamylase activity or be a fragment of the amino acid sequence of SEQ ID NO: 33 having glucoamylase activity (which can, in an embodiment, correspond to a fragment of the amino acid sequence of SEQ ID NO: 33 lacking its signal sequence, e.g., for example between residues 19 to 630 of SEQ ID NO: 33). For example, the exogenous glucoamylase can be from a *Trichocladium* sp., such as, for example, from *Trichocladium griseum*. In an embodiment, the exogenous glucoamylase corresponds to Uniprot Q12623 or GenBank Accession Number AAA33386. In another embodiment, the exogenous glucoamylase can have the amino acid sequence of SEQ ID NO: 34, be a variant of the amino acid sequence of SEQ ID NO: 34 having glucoamylase activity or be a fragment of the amino acid sequence of SEQ ID NO: 34 having glucoamylase activity (which can, in an embodiment, correspond to a fragment of the amino acid sequence of SEQ ID NO: 34 lacking its signal sequence, e.g., for example between residues 20 and 620 of SEQ ID NO: 34).

For example, the exogenous alpha-amylase can be from a *Rhizomucor* sp., such as, for example, from *Rhizomucor pusillus*. In an embodiment, the exogenous alpha-amylase corresponds to Uniprot M9T189. In another embodiment, the exogenous alpha-amylase can have the amino acid sequence of SEQ ID NO: 17, be a variant of the amino acid sequence of SEQ ID NO: 17 having alpha-amylase activity or be a fragment of the amino acid sequence of SEQ ID NO: 17 having alpha-amylase activity (which can, in an embodiment, correspond to a fragment of the amino acid sequence of SEQ ID NO: 17 lacking its signal sequence, e.g., for example, between residues 22 and 471 of SEQ ID NO: 17). For example, the exogenous alpha-amylase can be from a *Aspergillus* sp., such as, for example, from *Aspergillus luchuensis*. In an embodiment, the exogenous alpha-amylase corresponds to Uniprot A0A146F6W4 or to GenBank Accession Number GAT21778. In another embodiment, the exogenous alpha-amylase can have the amino acid sequence of SEQ ID NO: 18, be a variant of the amino acid sequence of SEQ ID NO: 18 having alpha-amylase activity or be a fragment of the amino acid sequence of SEQ ID NO: 18 having alpha-amylase activity (which can, in an embodiment, correspond to a fragment of the amino acid sequence of SEQ ID NO: 18 lacking its signal sequence, e.g., for example, between residues 22 to 615 of SEQ ID NO: 18). In an embodiment, the exogenous alpha-amylase corresponds to Uniprot O13296 or to GenBank Accession Number BAA22993. In another embodiment, the exogenous alpha-amylase can have the amino acid sequence of SEQ ID NO: 26, be a variant of the amino acid sequence of SEQ ID NO: 26 having alpha-amylase activity or be a fragment of the amino acid sequence of SEQ ID NO: 26 having alpha-amylase activity (which can, in an embodiment, correspond to a fragment of the amino acid sequence of SEQ ID NO: 26 lacking its signal sequence, e.g., for example between residues 22 to 640 of SEQ ID NO: 26). For example, the exogenous alpha-amylase can be from *Aspergillus oryzae*. In an embodiment, the exogenous alpha-amylase corresponds to Uniprot Q2UIS5 or to GenBank Accession Number XP_001820542. In another embodiment, the exogenous alpha-amylase can have the amino acid sequence of SEQ ID NO: 19, be a variant of the amino acid sequence of SEQ ID NO: 19 having alpha-amylase activity or be a fragment of the amino acid sequence of SEQ ID NO: 19 having alpha-amylase activity (which can, in an embodiment, correspond to a fragment of the amino acid sequence of SEQ ID NO: 19 lacking its signal sequence, e.g., for example between residues 24 to 549 of SEQ ID NO: 19). For example, the exogenous alpha-amylase can be from *Aspergillus niger*. In an embodiment, the exogenous alpha-amylase corresponds to Uniprot A2QTS4 or to GenBank Accession Number XP_001393626. In another embodiment, the exogenous alpha-amylase can have the amino acid sequence of SEQ ID NO: 21, be a variant of the amino acid sequence of SEQ ID NO: 21 having alpha-amylase activity or be a fragment of the amino acid sequence of SEQ ID NO: 21 having alpha-amylase activity (which can, in an embodiment, correspond to a fragment of the amino acid sequence of SEQ ID NO: 21 lacking its signal sequence, e.g., for example between residues 26 to 555 of SEQ ID NO: 21). In an embodiment, the exogenous alpha-amylase corresponds to Uniprot A2R6F9 or to GenBank Accession Number XP_001397301. In another embodiment, the exogenous alpha-amylase can have the amino acid sequence of SEQ ID NO: 22, be a variant of the amino acid sequence of SEQ ID NO: 22 having alpha-amylase activity or be a fragment of the amino acid sequence of SEQ ID NO: 22 having alpha-amylase activity (which can, in an embodiment, correspond to a fragment of the amino acid sequence of SEQ ID NO: 22 lacking its signal sequence, e.g., for example between residues 23 and 567 of SEQ ID NO: 22). In an embodiment, the exogenous alpha-amylase corresponds to GenBank Accession Number XP_001395328. In another embodiment, the exogenous alpha-amylase can have the amino acid sequence of SEQ ID NO: 23, be a variant of the amino acid sequence of SEQ ID NO: 23 having alpha-amylase activity or be a fragment of the amino acid sequence of SEQ ID NO: 23 having alpha-amylase activity (which can, in an embodiment, correspond to a fragment of the amino acid sequence of SEQ ID NO: 23 lacking its signal sequence, e.g., for example between residues 30 and 550 of SEQ ID NO: 23). In an embodiment, the exogenous alpha-amylase corresponds to Uniprot A0A370BQ30 or to GenBank Accession Number RDH15462. In another embodiment, the exogenous alpha-amylase can have the amino acid sequence of SEQ ID NO: 24, be a variant of the amino acid sequence of SEQ ID NO: 24 having alpha-amylase activity or be a fragment of the amino acid sequence of SEQ ID NO: 24 having alpha-amylase activity (which can, in an embodiment, correspond to a fragment of the amino acid sequence of SEQ ID NO: 24 lacking its signal sequence, e.g., for example between residues 17 and 524 of SEQ ID NO: 24). For example, the exogenous alpha-amylase can be from *Aspergillus fischeri*. In an embodiment, the exogenous alpha-amylase corresponds to Uniprot A1CYB1 or to GenBank Accession Number XP_001265628. In another embodiment, the exogenous alpha-amylase can have the amino acid sequence of SEQ ID NO: 25, be a variant of the amino acid sequence of SEQ ID NO: 25 having alpha-amylase activity or be a fragment of the amino acid sequence of SEQ ID NO: 25 having alpha-amylase activity (which can, in an embodiment, correspond to a fragment of the amino acid sequence of SEQ ID NO: 25 lacking its signal sequence, e.g., for example between residues 24 to 632 of SEQ ID NO: 25). For example, the exogenous alpha-amylase can be from a *Homo* sp., such as, for example, from *Homo sapiens*. In an embodiment, the exogenous alpha-amylase corresponds to GenBank Accession Number 1B2Y_A. In another embodiment, the exogenous alpha-amylase can have the amino acid sequence of SEQ ID NO: 20, be a variant of the amino acid sequence of SEQ ID NO: 20 having alpha-amylase activity or be a fragment of the amino acid sequence of SEQ ID NO: 20 having alpha-amylase activity (which can, in an embodiment, correspond to a fragment of the amino acid sequence of SEQ ID NO: 20 lacking its signal sequence, e.g., for example between residues 20 to 515 of SEQ ID NO: 20).

In some embodiments, the recombinant yeast host cells described herein reduce the need for exogenous enzyme dosing in saccharification/fermentation. In some embodiments, the recombinant yeast host cells described herein reduce the need for exogenous enzyme dosing in simultaneous saccharification and fermentation (SSF). In some embodiments, the recombinant yeast host cells described herein alleviate the need for exogenous enzyme dosing in SSF. In some embodiments, the recombinant yeast host cells described herein is less susceptible to temperature and pH stress in SSF processes. As such, in some embodiments of the process, the recombinant yeast host cell of the present disclosure allow for a complete displacement of the exogenous purified enzyme (which can be in some embodiments a glucoamylase) while achieving the same fermentation yield than a corresponding yeast strain in the presence of a full dose of the exogenous enzyme (which can be in some embodiments a glucoamylase). The process can, in some embodiments, alleviate the need to supplement the hydrolyzed biomass with a purified exogenous enzyme (which can be in some embodiments a glucoamylase) during the fermentation step.

Yeast Products and Compositions

The recombinant yeast host cells of the present disclosure can be used in the preparation of a yeast composition (e.g., a composition comprising the recombinant yeast host cell) comprising the heterologous polypeptide having glucoamylase activity. The yeast compositions and products can be provided in a liquid, semi-liquid or dry form.

A yeast composition refers to a composition comprising the recombinant yeast host cell of the present disclosure (which may be, in some embodiments, a viable recombinant yeast host cell) as well as the heterologous polypeptide having glucoamylase activity. The process for providing a yeast composition comprises providing a propagated the recombinant yeast host cell and removing, at least one component of the mixture obtained after propagation to provide the yeast composition. This component can be, without limitation, water, amino acids, peptides and proteins, nucleic acid residues and nucleic acid molecules, cellular debris, fermentation products, etc. In an embodiment, the process comprises substantially isolating the propagated recombinant yeast host cells from the components of the propagation medium. As used in the context of the present disclosure, the expression "substantially isolating" refers to the removal of the majority of the components of the propagation medium from the propagated recombinant yeast host cells. In some embodiments, "substantially isolating" refers to concentrating the propagated recombinant yeast host cell to at least 5, 10, 15, 20, 25, 30, 35, 45% or more when compared to the concentration of the recombinant yeast host cell prior to the isolation. In order to provide the yeast composition, the propagated recombinant yeast host cells can be centrifuged (and the resulting cellular pellet comprising the propagated recombinant yeast host cells can optionally be washed), filtered and/or dried (optionally using a vacuum-drying technique). The isolated recombinant yeast host cells can then be formulated in a yeast composition. The yeast composition can be provided in an active or a semi-active form. The yeast composition can be provided in a liquid, semi-solid or dry form. In an embodiment, the yeast composition can be provided in the form of a cream yeast. In some embodiments, the process also include propagating the recombinant yeast host cell prior to the removal step. The yeast composition can be optionally stored prior to the fermentation phase. In such embodiment, the yeast composition can include, for example, one or more stabilizers or preservatives and, in some embodiment, an unfermentable carbon source (such as trehalose for example).

In some embodiments, the recombinant yeast host cell or the yeast composition obtained therefrom can be provided in a composition in combination with starch. Such composition can include additional exogenous enzyme(s) which may be used during the saccharification and/or fermentation steps.

The present invention will be more readily understood by referring to the following examples which are given to illustrate the invention rather than to limit its scope.

Example I—Heterologous Starch Digesting Glucoamylase in Recombinant Yeast Cells

TABLE 1

Genotypes of the strains used in the examples. All the recombinant strains were derived from M2390 and expressed the recombinant enzyme under transcriptional control of the constitutive tef2p promoter and idp1t terminator.

| Strain name | Expressed enzyme | Enzyme description |
| --- | --- | --- |
| M2390 | None - wild-type | *Saccharomyces cerevisiae* strain |
| M17199 | MP1152 (SEQ ID NO: 9) | Glucoamylase from *Saccharomycopsis fibuligera* associated with the signal sequence of *Saccharomyces cerevisiae* alpha-mating factor 1 |
| M15621 | SEQ ID NO: 6 | Glucoamylase from *Rasamsonia emersonii* associated with its native signal sequence |

TABLE 1-continued

Genotypes of the strains used in the examples. All the recombinant strains were derived from M2390 and expressed the recombinant enzyme under transcriptional control of the constitutive tef2p promoter and idp1t terminator.

| Strain name | Expressed enzyme | Enzyme description |
| --- | --- | --- |
| M23176 and M23177* | MP1262 (SEQ ID NO: 1) | Glucoamylase from *Rasamsonia emersonii* associated with the signal sequence of *Saccharomyces cerevisiae* alpha-mating factor 1 |

*M23176 and M23177 are two different isolates from the same transformation

Permissive corn mash fermentation data. Permissive fermentation conditions were conducted as follows: 32.4% total solids, 300 ppm urea, 33° C. (1-48 hours), exogenous glucoamylase GA enzyme inclusion as listed under each bar of the figures. FIG. 1 illustrates the surprising result of MP1262 secreting strains (M23176 and M23177) showing performance parity at 0% exogenous glucoamylase inclusion to M2390 dosed with a full 100% dose of exogenous enzyme. Without wishing to be bound to theory, the fact that the ethanol titers show parity for isolates M23176/M23177 with M2390 suggests that the expression of the heterologous MP1262 does not seem to reduce strain fermentative performance.

Figure 2:
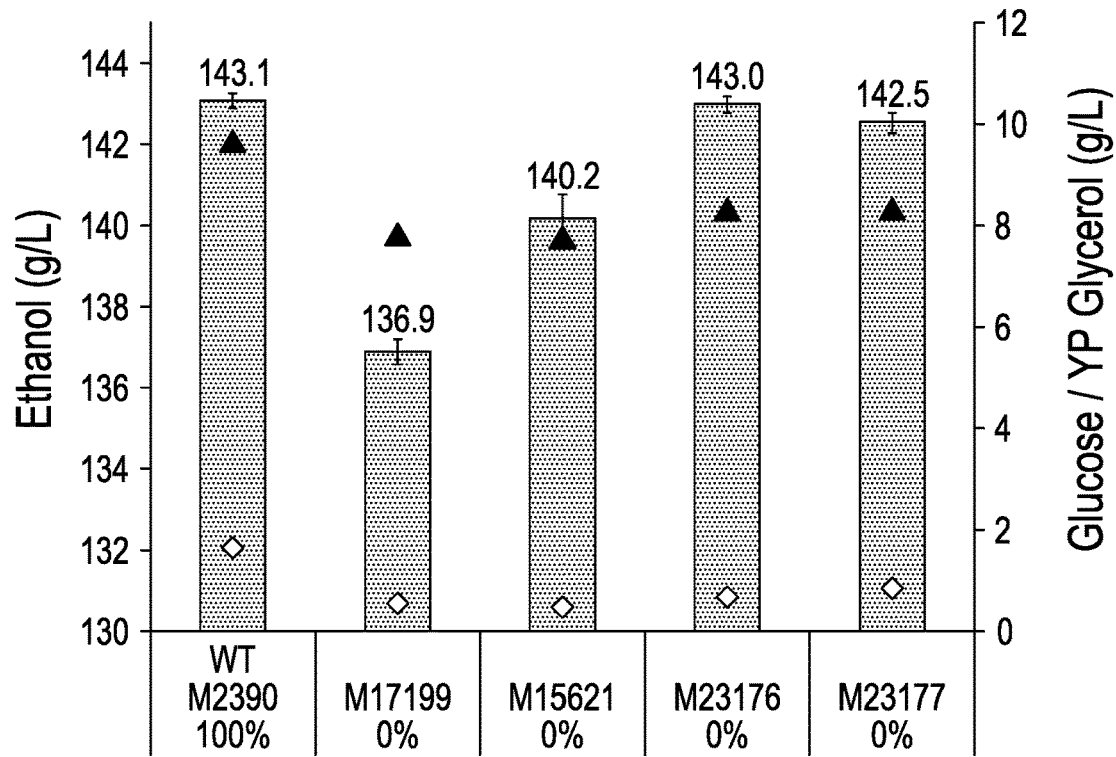
FIG. 2 illustrates the data associated with a corn mash fermentation (analyzed 48 hours into the fermentation). Bars represent endpoint ethanol titers (plotted on the left y axis, in g/L). Lozenges (♦) denote glucose titers and triangles (▲) represent yeast-produced (YP) glycerol titers (right y axis, all in g/L). Results are shown for strains M2390, M17199, M15621, M23176 and M23177 (see Table 1 for a description of the strains). The amount (% of control dose) of exogenous glucoamylase used is listed under each bar.

FIG. 2 further illustrates that the signal peptide optimized MP1262 secreting strains can successfully finish fermentation with 100% exogenous enzyme displacement, achieving the same titers as M2390 dosed with a full 100% GA dose.

Figure 3:
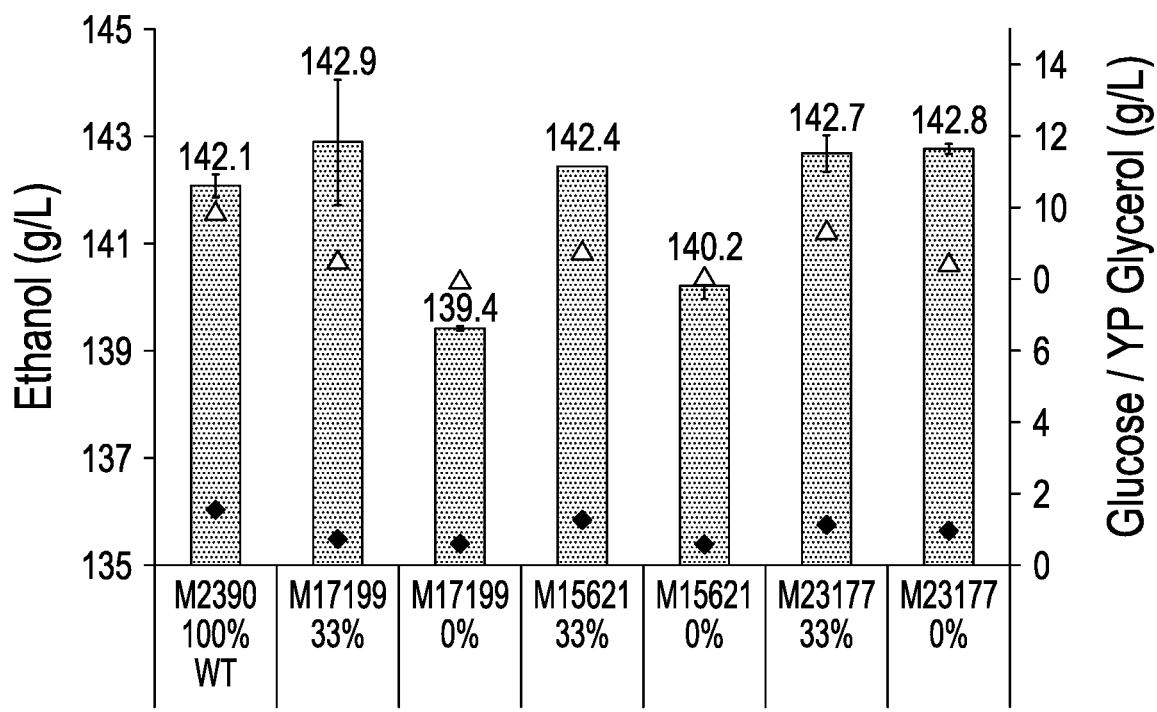
FIG. 3 illustrates the data associated with a permissive corn mash fermentation in the presence or absence of exogenous glucoamylase (analyzed 48 hours into the fermentation). Bars represent endpoint ethanol titers (plotted on the left y axis, in g/L). Lozenges (♦) denote glucose titers and triangles (▲) represent yeast-produced (YP) glycerol titers (right y axis, all in g/L). Results are shown for strains M2390, M17199, M15621 and M23177. The amount (% of control dose) of exogenous glucoamylase used is listed under each bar.

In FIG. 3, four strains were compared side by side at either 33% or 0% exogenous enzyme inclusion. The reduction in fermentation performance going from 33% to 0% enzyme inclusion for M17199 and M15621 can be attributed to insufficient heterologous GA secretion in the conditions tested. Strain M23177 did not exhibit a reduction in in fermentation performance in the absence of the exogenous enzyme.

Non-permissive corn mash fermentation data. The fermentations were conducted according to the following conditions: 32.4% total solids, no urea, 34° C. (1-48 hours) or 36° C. (1-48 hours, for heat-treatment challenge only), 0.38% w/v lactic acid added 20 hours into the fermentation (for lactic acid challenge only), exogenous glucoamylase (GA) enzyme inclusion as listed under each bar of the figures.

Figure 4:
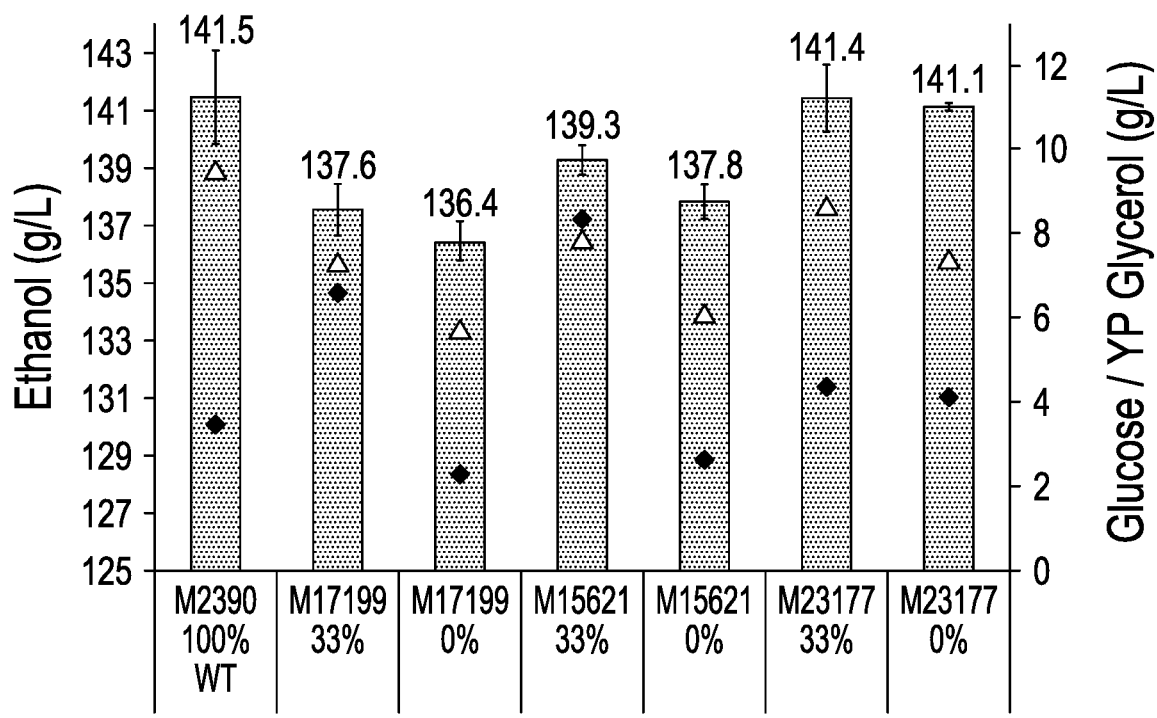
FIG. 4 illustrates the data associated with a non-permissive (lactic acid treatment) corn mash fermentation (analyzed 48 hours into the fermentation). Bars represent endpoint ethanol titers (plotted on the left y axis, in g/L). Lozenges (♦) denote glucose titers and triangles (▲) represent yeast-produced (YP) glycerol titers (right y axis, all in g/L). Results are shown for strains M2390, M17199, M15621 and M23177 in the presence or absence of exogenous glucoamylase. The amount (% of control dose) of exogenous glucoamylase used is listed under each bar.
Figure 5:
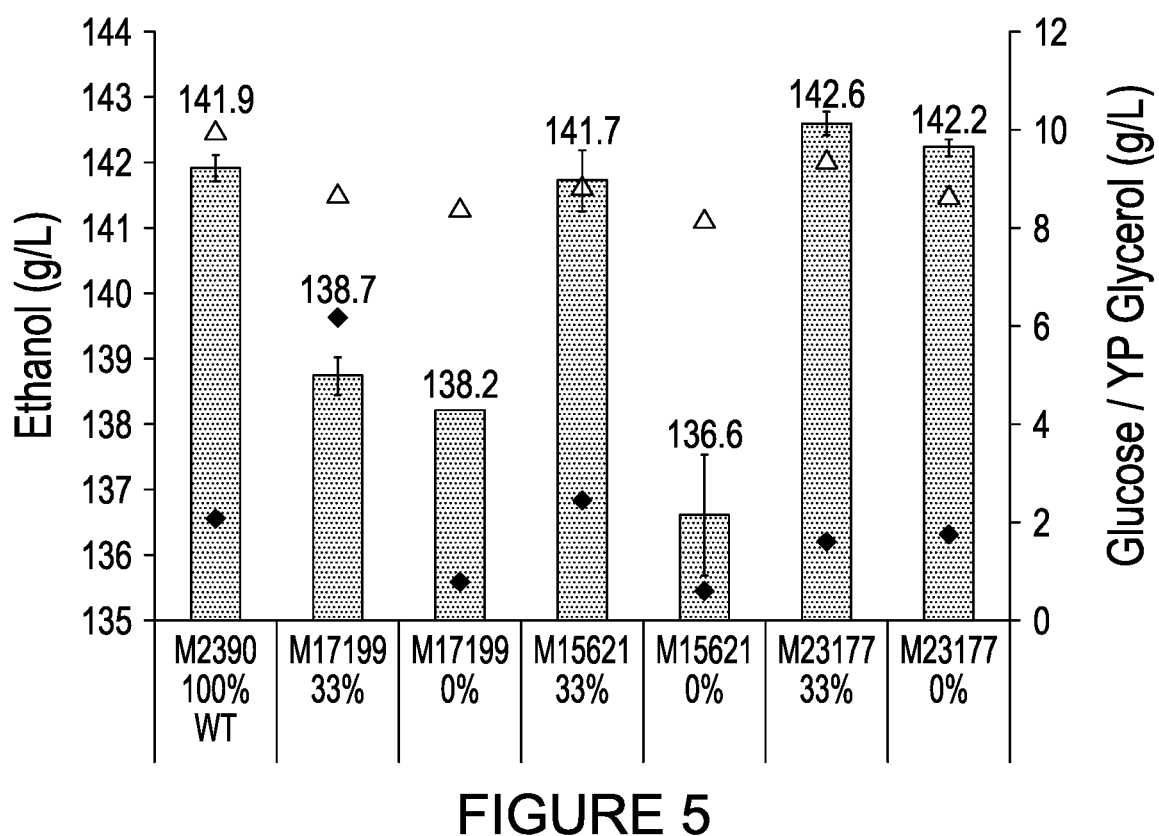
FIG. 5 illustrates the data associated with a non-permissive (heat treatment) corn mash fermentation (analyzed 48 hours into the fermentation). Bars represent endpoint ethanol titers (plotted on the left y axis, in g/L). Lozenges (♦) denote glucose titers and triangles (▲) represent yeast-produced (YP) glycerol titers (right y axis, all in g/L). Results are shown for strains M2390, M17199, M15621 and M23177. The amount (% of control dose) of exogenous glucoamylase used is listed under each bar.

As shown in FIGS. 4 and 5, strain M23177 did not exhibit a reduction in in fermentation performance in the absence of the exogenous enzyme during non-permissive fermentation (FIG. 4 shows the results associated with a lactic acid challenge and FIG. 5 shows the results associated with a heat treatment).

Example II—Corn Fermentation Using Dry Yeast Samples

Permissive corn mash fermentation. Permissive fermentation conditions were conducted as follows: 31.55% total solids, 612 ppm urea, 32° C. (0-52 hours), exogenous glucoamylase GA enzyme inclusion as listed under each bar of the figures. The "100%" enzyme dose is equivalent to 0.6

AGU/gTS. Yeast dosing was carried out through direct pitch (0.05 g dry cell weight/L inoculum) from dry yeast samples rehydrated in sterile water at ambient temperature for 30 minutes. The fermentations were carried out using 10 mL scintillation vials with a total sample size of 3 grams.

Figure 6:
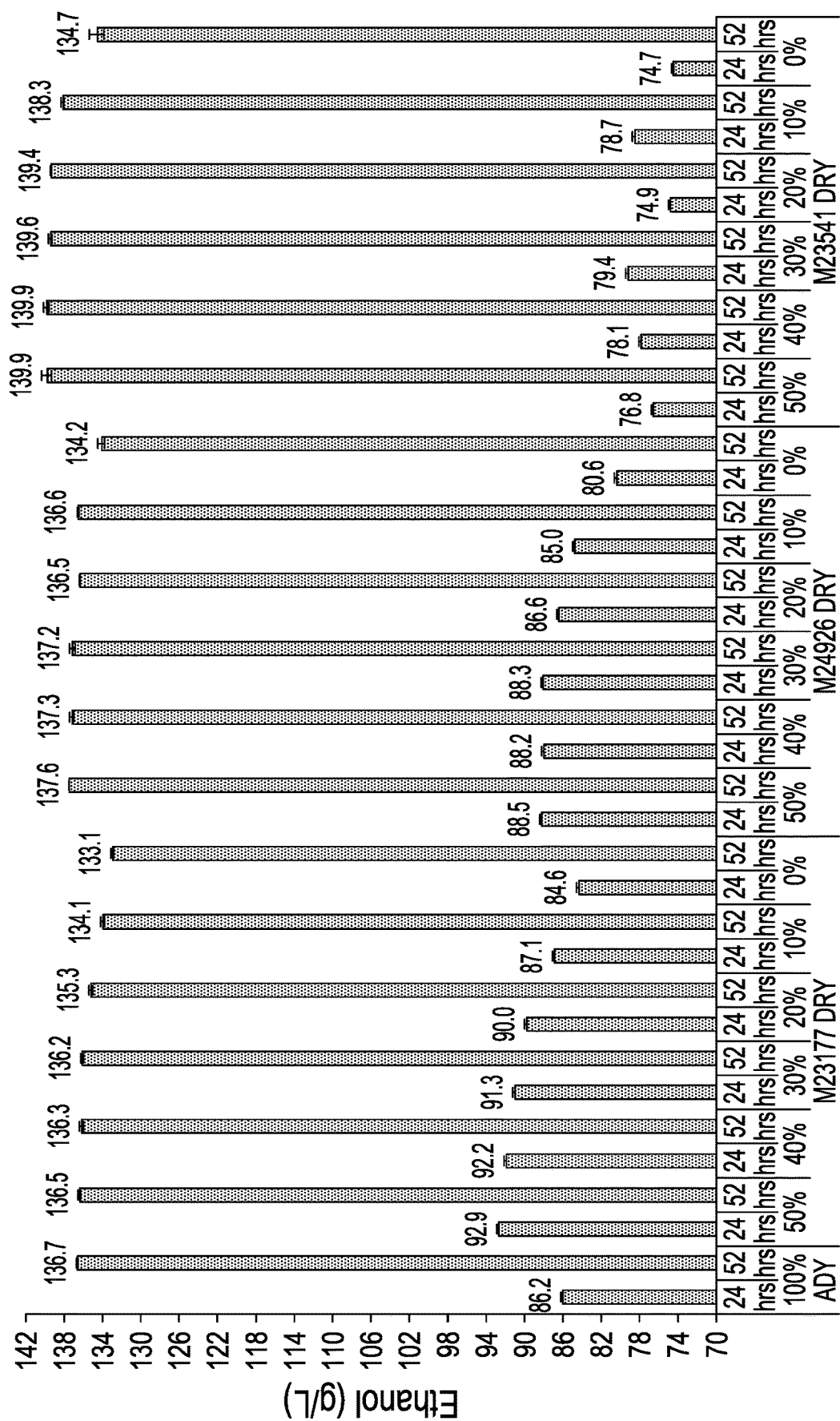
FIG. 6 illustrates the data associated with permissive fermentations analyzed 24 hours and 52 hours into the fermentation. Bars represent endpoint ethanol titers (plotted on the left y axis, in g/L). Results are shown for strains Ethanol Red (e.g., active dry yeast or ADY), M23177, M24926 and M23541 in function of the amount (% of dose) of exogenous glucoamylase used (both listed under each bar).
Figure 7:
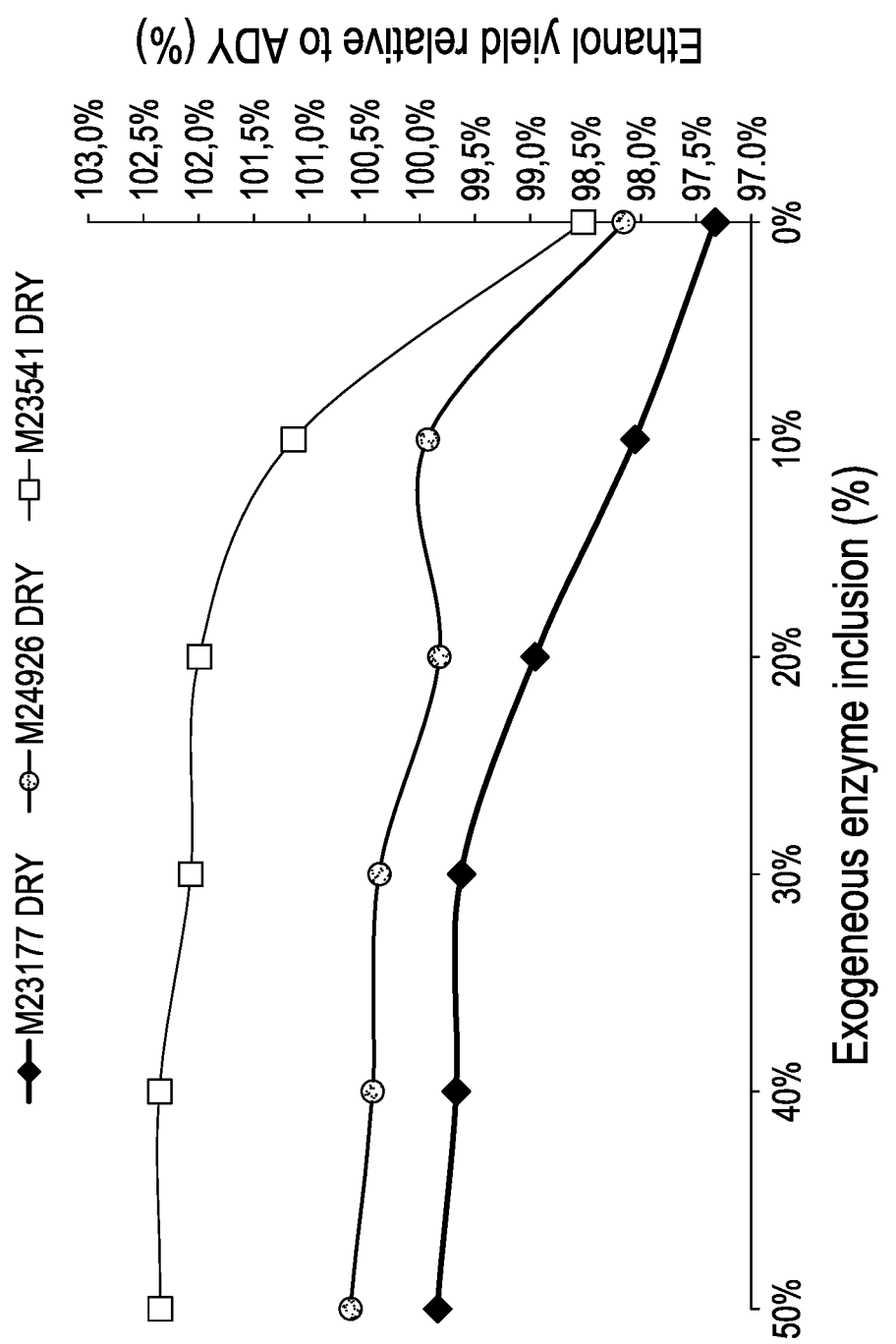
FIG. 7 illustrates the ethanol titer data of FIG. 6 obtained at 52 hours, but plotted as relative ethanol yield compared to Ethanol Red (ADY). For each strain (M23177 ♦, M24926 ● and M23541 □) and each enzyme inclusion, the drop ethanol titer is plotted as a ratio to the drop ethanol titer of Ethanol Red (ADY) with 100% enzyme inclusion (y axis). The exogenous enzyme inclusion (% of dose) for each condition is reported as a percentage from the dose used with ADY and is indicated on the x axis.

The fermentation performance of three distinct yeast strains has been determined. Once reconstituted, the dry yeasts samples comprising strains M23177 (described in Example I), M24926 (expressing the *R. emersonii* glucoamylase with the alpha-mating factor signal sequence like strain M23177 and bearing an additional "trehalose reduction" genetic modification described in U.S. Pat. No. 10,570,421 and incorporated herewith in their entirety) and M23541 (expressing the *R. emersonii* glucoamylase with the alpha-mating factor signal sequence like strain M23177 and bearing additional "glycerol reduction background modifications" refers the genetic modifications described in WO2011140386, WO2012138942 and WO2020100069 allowing the reduction of production of glycerol, all incorporated herewith in their entirety) were shown to produce ethanol even when a lower dose of exogenous glucoamylase was used (FIG. 6). In FIG. 7, the results obtained in FIG. 6 (at 52 hours) were plotted as relative ethanol yield compared to the result obtained with the conventional strain Ethanol Red (provided in an active dried form or ADY).

While the invention has been described in connection with specific embodiments thereof, it will be understood that the scope of the claims should not be limited by the preferred embodiments set forth in the examples, but should be given the broadest interpretation consistent with the description as a whole.

What is claimed is:

1. A recombinant yeast host cell for saccharification and fermentation of a biomass, the recombinant yeast host cell having a heterologous nucleic acid molecule encoding a heterologous polypeptide having glucoamylase activity, wherein the heterologous nucleic acid molecule comprises:
a first polynucleotide encoding a heterologous signal sequence wherein the heterologous signal sequence has the amino acid sequence of SEQ ID NO: 5; and
a second polynucleotide encoding the heterologous polypeptide having glucoamylase activity, wherein the polypeptide having glucoamylase activity has the amino acid sequence of SEQ ID NO: 3 or 13, is a variant having at least 90% identity with the amino acid sequence of SEQ ID NO: 3 or 13 and having glucoamylase activity, or is a fragment having at least 90% identity with the amino acid sequence of SEQ ID NO: 3 or 13 and having glucoamylase activity;
wherein the first polynucleotide molecule is operatively associated with the second polynucleotide molecule.

2. The recombinant yeast host cell of claim 1, wherein the heterologous nucleic acid molecule encodes the heterologous polypeptide having the amino acid sequence of SEQ ID NO: 1 or 11, a variant having at least 90% identity with the amino acid sequence of SEQ ID NO: 1 or 11 and having glucoamylase activity, or a fragment having at least 90% identity with the amino acid sequence of SEQ ID NO: 1 or 11 and having glucoamylase activity.

3. The recombinant yeast host cell of claim 1, wherein the heterologous nucleic acid molecule further comprises a third polynucleotide comprising a heterologous promoter operatively associated with the first polynucleotide and the second polynucleotide allowing the expression of the heterologous polypeptide having glucoamylase activity.

4. The recombinant yeast host cell of claim 3, wherein the heterologous promoter is capable of allowing the expression of the heterologous polypeptide having glucoamylase activity during propagation.

5. The recombinant yeast host cell of claim 1, wherein the heterologous polypeptide having glucoamylase activity is a secreted polypeptide.

6. The recombinant yeast host cell of claim 1, wherein the heterologous polypeptide having glucoamylase activity is a membrane-associated polypeptide.

7. The recombinant yeast host cell of claim 6, wherein the membrane-associated polypeptide is a tethered polypeptide.

8. The recombinant yeast host cell of claim 1 comprising a further heterologous nucleic acid molecule encoding a heterologous alpha-amylase and/or a heterologous glucoamylase.

9. The recombinant yeast host cell of claim 8, wherein the heterologous alpha-amylase has the amino acid sequence of any one of SEQ ID NO: 17 to 26, is a variant having at least 90% identity with the amino acid sequence of any one of SEQ ID NO: 17 to 26 and having alpha-amylase activity or is a fragment having at least 90% identity with the amino acid sequence of any one of SEQ ID NO: 17 to 26 and having alpha-amylase activity.

10. The recombinant yeast host cell of claim 8, wherein the heterologous glucoamylase has the amino acid sequence of any one of SEQ ID NO: 27 to 36, a variant having at least 90% identity with the amino acid sequence of any one of SEQ ID NO: 27 to 36 and having glucoamylase activity or a fragment having at least 90% identity with the amino acid sequence of any one of SEQ ID NO: 27 to 36 and having glucoamylase activity.

11. The recombinant yeast host cell of claim 1, wherein the recombinant yeast host cell is from the genus *Saccharomyces*.

12. The recombinant yeast host cell of claim 11, wherein the recombinant yeast host cell is from the species *Saccharomyces cerevisiae*.

13. A composition comprising the recombinant yeast host cell of claim 1 and starch.

14. A process for saccharification and fermentation of a biomass into a fermentation product, the process comprises contacting the biomass with the recombinant yeast host cell defined in claim 1, under a condition that allows the conversion of at least a part of the biomass into the fermentation product.

15. The process of claim 14, wherein the biomass is derived from or comprises corn, potato, cassava, rice, wheat, lignocellulosic material, milo or buckwheat.

16. The process of claim 15, wherein the biomass is derived from or comprises corn.

17. The process of claim 16, wherein the biomass comprises or is corn mash.

18. The process of claim 14, wherein the fermentation product is ethanol.

19. The process of claim 14, wherein the fermentation is conducted in the presence of a stressor.

20. The process of claim 19, wherein the stressor is low pH.

21. The process of claim 20, wherein the stressor is pH of 5.0 or lower.

22. The process of claim 20, wherein the stressor is pH of 4.0 or lower.

23. The process of claim 19, wherein the stressor is an elevated temperature.

24. The process of claim 14 comprising including an exogenous enzyme in the biomass.

25. The process of claim 24, wherein the exogenous enzyme is an alpha-amylase and/or a glucoamylase.

26. The process of claim 25, wherein the alpha-amylase has the amino acid sequence of any one of SEQ ID NO: 17 to 26, is a variant having at least 90% identity with the amino acid sequence of any one of SEQ ID NO: 17 to 26 and having alpha-amylase activity or is a fragment having at least 90% identity with the amino acid sequence of any one of SEQ ID NO: 17 to 26 and having alpha-amylase activity.

27. The process of claim 25, wherein the glucoamylase has the amino acid sequence of any one of SEQ ID NO: 27 to 36, is a variant having at least 90% identity with the amino acid sequence of any one of SEQ ID NO: 27 to 36 having glucoamylase activity or is a fragment of the amino acid sequence of any one of SEQ ID NO: 27 to 36 and having glucoamylase activity.

28. The process of claim 14 avoiding including an exogenous enzyme in the biomass.

29. The process of claim 28, wherein the exogenous enzyme is a glucoamylase.

* * * * *

SEQUENCE LISTING

```
<160> NUMBER OF SEQ ID NOS: 36

<210> SEQ ID NO 1
<211> LENGTH: 617
<212> TYPE: PRT
<213> ORGANISM: Artificial Sequence
<220> FEATURE:
<223> OTHER INFORMATION: Glucoamylase from Rasamsonia emersonii (Uniprot
      Q9C1V4) associated with the signal sequence of Saccharomyces
      cerevisiae alpha-mating factor 1
<220> FEATURE:
<221> NAME/KEY: SIGNAL
<222> LOCATION: (1)..(19)

<400> SEQUENCE: 1

Met Arg Phe Pro Ser Ile Phe Thr Ala Val Leu Phe Ala Ala Ser Ser
1               5                   10                  15

Ala Leu Ala Arg Ala Pro Val Ala Ala Arg Ala Thr Gly Ser Leu Asp
            20                  25                  30

Ser Phe Leu Ala Thr Glu Thr Pro Ile Ala Leu Gln Gly Val Leu Asn
        35                  40                  45

Asn Ile Gly Pro Asn Gly Ala Asp Val Ala Gly Ala Ser Ala Gly Ile
    50                  55                  60

Val Val Ala Ser Pro Ser Arg Ser Asp Pro Asn Tyr Phe Tyr Ser Trp
65                  70                  75                  80

Thr Arg Asp Ala Ala Leu Thr Ala Lys Tyr Leu Val Asp Ala Phe Ile
                85                  90                  95

Ala Gly Asn Lys Asp Leu Glu Gln Thr Ile Gln Gln Tyr Ile Ser Ala
            100                 105                 110

Gln Ala Lys Val Gln Thr Ile Ser Asn Pro Ser Gly Asp Leu Ser Thr
        115                 120                 125

Gly Gly Leu Gly Glu Pro Lys Phe Asn Val Asn Glu Thr Ala Phe Thr
    130                 135                 140

Gly Pro Trp Gly Arg Pro Gln Arg Asp Gly Pro Ala Leu Arg Ala Thr
145                 150                 155                 160

Ala Leu Ile Ala Tyr Ala Asn Tyr Leu Ile Asp Asn Gly Glu Ala Ser
                165                 170                 175

Thr Ala Asp Glu Ile Ile Trp Pro Ile Val Gln Asn Asp Leu Ser Tyr
            180                 185                 190

Ile Thr Gln Tyr Trp Asn Ser Ser Thr Phe Asp Leu Trp Glu Glu Val
        195                 200                 205

Glu Gly Ser Ser Phe Phe Thr Thr Ala Val Gln His Arg Ala Leu Val
    210                 215                 220
```

```
Glu Gly Asn Ala Leu Ala Thr Arg Leu Asn His Thr Cys Ser Asn Cys
225                 230                 235                 240

Val Ser Gln Ala Pro Gln Val Leu Cys Phe Leu Gln Ser Tyr Trp Thr
            245                 250                 255

Gly Ser Tyr Val Leu Ala Asn Phe Gly Gly Ser Gly Arg Ser Gly Lys
                260                 265                 270

Asp Val Asn Ser Ile Leu Gly Ser Ile His Thr Phe Asp Pro Ala Gly
            275                 280                 285

Gly Cys Asp Asp Ser Thr Phe Gln Pro Cys Ser Ala Arg Ala Leu Ala
            290                 295                 300

Asn His Lys Val Val Thr Asp Ser Phe Arg Ser Ile Tyr Ala Ile Asn
305                 310                 315                 320

Ser Gly Ile Ala Glu Gly Ser Ala Val Ala Val Gly Arg Tyr Pro Glu
                325                 330                 335

Asp Val Tyr Gln Gly Gly Asn Pro Trp Tyr Leu Ala Thr Ala Ala Ala
                340                 345                 350

Ala Glu Gln Leu Tyr Asp Ala Ile Tyr Gln Trp Lys Lys Ile Gly Ser
            355                 360                 365

Ile Ser Ile Thr Asp Val Ser Leu Pro Phe Phe Gln Asp Ile Tyr Pro
370                 375                 380

Ser Ala Ala Val Gly Thr Tyr Asn Ser Gly Ser Thr Thr Phe Asn Asp
385                 390                 395                 400

Ile Ile Ser Ala Val Gln Thr Tyr Gly Asp Gly Tyr Leu Ser Ile Val
                405                 410                 415

Glu Lys Tyr Thr Pro Ser Asp Gly Ser Leu Thr Glu Gln Phe Ser Arg
                420                 425                 430

Thr Asp Gly Thr Pro Leu Ser Ala Ser Ala Leu Thr Trp Ser Tyr Ala
            435                 440                 445

Ser Leu Leu Thr Ala Ser Ala Arg Arg Gln Ser Val Val Pro Ala Ser
450                 455                 460

Trp Gly Glu Ser Ser Ala Ser Ser Val Pro Ala Val Cys Ser Ala Thr
465                 470                 475                 480

Ser Ala Thr Gly Pro Tyr Ser Thr Ala Thr Asn Thr Val Trp Pro Ser
                485                 490                 495

Ser Gly Ser Gly Ser Ser Thr Thr Ser Ser Ala Pro Cys Thr Thr
                500                 505                 510

Pro Thr Ser Val Ala Val Thr Phe Asp Glu Ile Val Ser Thr Ser Tyr
            515                 520                 525

Gly Glu Thr Ile Tyr Leu Ala Gly Ser Ile Pro Glu Leu Gly Asn Trp
            530                 535                 540

Ser Thr Ala Ser Ala Ile Pro Leu Arg Ala Asp Ala Tyr Thr Asn Ser
545                 550                 555                 560

Asn Pro Leu Trp Tyr Val Thr Val Asn Leu Pro Pro Gly Thr Ser Phe
                565                 570                 575

Glu Tyr Lys Phe Phe Lys Asn Gln Thr Asp Gly Thr Ile Val Trp Glu
            580                 585                 590

Asp Asp Pro Asn Arg Ser Tyr Thr Val Pro Ala Tyr Cys Gly Gln Thr
            595                 600                 605

Thr Ala Ile Leu Asp Asp Ser Trp Gln
610                 615

<210> SEQ ID NO 2
<211> LENGTH: 1854
```

```
<212> TYPE: DNA
<213> ORGANISM: Artificial Sequence
<220> FEATURE:
<223> OTHER INFORMATION: Encoding SEQ ID NO: 1

<400> SEQUENCE: 2
atgaggttcc catctatttt caccgctgtt ttgtttgctg cttcttctgc tttggctaga      60
gcaccagttg ctgctagagc tacaggttct ttggattctt ttttggctac tgaaactcca     120
atcgcattgc aaggtgtttt gaacaatatt ggtccaaacg tgctgatgt tgccggtgct      180
tctgctggta tagttgttgc ttctccatct agatctgatc ccaattactt ttactcttgg     240
actagagatg ctgctttgac tgctaaatac ttggttgatg ctttcattgc cggtaacaag     300
gatttggaac aaaccattca acagtacatt ccgctcaag ctaaggttca aactatctct      360
aatccatccg tgatttgtc tactggtggt ttgggtgaac taagttcaa tgttaacgaa       420
actgcttta ctggtccatg gggtagacca caaagagatg gtccagcttt gagagctact      480
gctttaattg cttacgccaa ctacttgatc gataacggtg aagcttctac tgctgatgag     540
attatttggc caatcgttca aaacgacttg tcctacatta ctcagtactg gaactcttct     600
actttcgact gtgggaaga gttgaaggt tcttcttttt tcactaccgc cgttcaacat       660
agagctttgg ttgaaggtaa tgctttggct accagattga accatacttg ttctaactgt    720
gtttcccaag ctccacaagt tttgtgtttc ttgcaatctt attggaccgg ttcttacgtt    780
ttggctaatt ttggtggttc tggtagatct ggtaaggatg ttaattctat cttgggttcc    840
atccatactt ttgatcctgc tggtggttgt gatgattcta cttttcaacc atgttctgca    900
agagcattgg ctaaccataa ggttgttact gactctttca gatccatcta cgctattaac    960
tctggtattg ctgaaggttc agctgttgct gttggtagat atcctgaaga tgtttaccaa   1020
ggtggtaatc catggtattt ggctacagct gctgctgcag aacaattata tgatgctatc   1080
taccagtgga gaagatcgg ttctatttcc attaccgatg tgtctttgcc attcttccaa    1140
gacatatatc catctgctgc agttggtact acaactctg gttctactac tttcaacgat    1200
atcatctctg ctgttcaaac ttacggtgat ggttacttgt ctatcgtcga aaagtatact   1260
ccatccgatg gttctttgac cgaacaattt tctagaactg atggtactcc attgtctgct   1320
tcagctttga cttggtctta tgcttctttg ttgacagctt ctgctagaag gcaatctgtt   1380
gttccagctt cttggggtga tcttctgct tcttcagttc cagctgtttg ttctgctaca    1440
tctgctactg gtccttattc tacagctact aatactgttt ggccatcttc tggttcaggt   1500
tcttcaacta ctacttcttc tgctccttgt actactccaa cttcagttgc tgttactttc   1560
gatgagatcg tttctaccctc ttatggtgaa actatctact ggctggttc cattccagaa   1620
ttaggtaatt ggtctactgc ttccgctatt ccattgagag ctgatgctta cactaattct   1680
aacccattgt ggtacgttac cgttaatttg ccaccaggta catcttttga gtacaagttt   1740
ttcaagaacc agaccgatgg tactatcgtt tgggaagatg atccaaacag atcttatact   1800
gttccagcat actgtggtca aactaccgct attttggatg attcttggca gtga          1854

<210> SEQ ID NO 3
<211> LENGTH: 598
<212> TYPE: PRT
<213> ORGANISM: Rasamsonia emersonii

<400> SEQUENCE: 3

Arg Ala Pro Val Ala Ala Arg Ala Thr Gly Ser Leu Asp Ser Phe Leu
1               5                   10                  15
```

```
Ala Thr Glu Thr Pro Ile Ala Leu Gln Gly Val Leu Asn Asn Ile Gly
            20                  25                  30

Pro Asn Gly Ala Asp Val Ala Gly Ala Ser Ala Gly Ile Val Val Ala
        35                  40                  45

Ser Pro Ser Arg Ser Asp Pro Asn Tyr Phe Tyr Ser Trp Thr Arg Asp
50                  55                  60

Ala Ala Leu Thr Ala Lys Tyr Leu Val Asp Ala Phe Ile Ala Gly Asn
65                  70                  75                  80

Lys Asp Leu Glu Gln Thr Ile Gln Gln Tyr Ile Ser Ala Gln Ala Lys
                85                  90                  95

Val Gln Thr Ile Ser Asn Pro Ser Gly Asp Leu Ser Thr Gly Gly Leu
            100                 105                 110

Gly Glu Pro Lys Phe Asn Val Asn Glu Thr Ala Phe Thr Gly Pro Trp
        115                 120                 125

Gly Arg Pro Gln Arg Asp Gly Pro Ala Leu Arg Ala Thr Ala Leu Ile
130                 135                 140

Ala Tyr Ala Asn Tyr Leu Ile Asp Asn Gly Glu Ala Ser Thr Ala Asp
145                 150                 155                 160

Glu Ile Ile Trp Pro Ile Val Gln Asn Asp Leu Ser Tyr Ile Thr Gln
                165                 170                 175

Tyr Trp Asn Ser Ser Thr Phe Asp Leu Trp Glu Glu Val Glu Gly Ser
            180                 185                 190

Ser Phe Phe Thr Thr Ala Val Gln His Arg Ala Leu Val Glu Gly Asn
        195                 200                 205

Ala Leu Ala Thr Arg Leu Asn His Thr Cys Ser Asn Cys Val Ser Gln
210                 215                 220

Ala Pro Gln Val Leu Cys Phe Leu Gln Ser Tyr Trp Thr Gly Ser Tyr
225                 230                 235                 240

Val Leu Ala Asn Phe Gly Gly Ser Gly Arg Ser Gly Lys Asp Val Asn
                245                 250                 255

Ser Ile Leu Gly Ser Ile His Thr Phe Asp Pro Ala Gly Gly Cys Asp
            260                 265                 270

Asp Ser Thr Phe Gln Pro Cys Ser Ala Arg Ala Leu Ala Asn His Lys
        275                 280                 285

Val Val Thr Asp Ser Phe Arg Ser Ile Tyr Ala Ile Asn Ser Gly Ile
290                 295                 300

Ala Glu Gly Ser Ala Val Ala Val Gly Arg Tyr Pro Glu Asp Val Tyr
305                 310                 315                 320

Gln Gly Gly Asn Pro Trp Tyr Leu Ala Thr Ala Ala Ala Ala Glu Gln
                325                 330                 335

Leu Tyr Asp Ala Ile Tyr Gln Trp Lys Lys Ile Gly Ser Ile Ser Ile
            340                 345                 350

Thr Asp Val Ser Leu Pro Phe Phe Gln Asp Ile Tyr Pro Ser Ala Ala
        355                 360                 365

Val Gly Thr Tyr Asn Ser Gly Ser Thr Thr Phe Asn Asp Ile Ile Ser
370                 375                 380

Ala Val Gln Thr Tyr Gly Asp Gly Tyr Leu Ser Ile Val Glu Lys Tyr
385                 390                 395                 400

Thr Pro Ser Asp Gly Ser Leu Thr Glu Gln Phe Ser Arg Thr Asp Gly
                405                 410                 415

Thr Pro Leu Ser Ala Ser Ala Leu Thr Trp Ser Tyr Ala Ser Leu Leu
            420                 425                 430
```

```
Thr Ala Ser Ala Arg Arg Gln Ser Val Val Pro Ala Ser Trp Gly Glu
            435                 440                 445

Ser Ser Ala Ser Ser Val Pro Ala Val Cys Ser Ala Thr Ser Ala Thr
    450                 455                 460

Gly Pro Tyr Ser Thr Ala Thr Asn Thr Val Trp Pro Ser Ser Gly Ser
465                 470                 475                 480

Gly Ser Ser Thr Thr Thr Ser Ser Ala Pro Cys Thr Thr Pro Thr Ser
                485                 490                 495

Val Ala Val Thr Phe Asp Glu Ile Val Ser Thr Ser Tyr Gly Glu Thr
            500                 505                 510

Ile Tyr Leu Ala Gly Ser Ile Pro Glu Leu Gly Asn Trp Ser Thr Ala
        515                 520                 525

Ser Ala Ile Pro Leu Arg Ala Asp Ala Tyr Thr Asn Ser Asn Pro Leu
    530                 535                 540

Trp Tyr Val Thr Val Asn Leu Pro Pro Gly Thr Ser Phe Glu Tyr Lys
545                 550                 555                 560

Phe Phe Lys Asn Gln Thr Asp Gly Thr Ile Val Trp Glu Asp Pro
                565                 570                 575

Asn Arg Ser Tyr Thr Val Pro Ala Tyr Cys Gly Gln Thr Thr Ala Ile
            580                 585                 590

Leu Asp Asp Ser Trp Gln
            595
```

<210> SEQ ID NO 4
<211> LENGTH: 1797
<212> TYPE: DNA
<213> ORGANISM: Artificial Sequence
<220> FEATURE:
<223> OTHER INFORMATION: Encoding SEQ ID NO: 3

<400> SEQUENCE: 4

```
agagcaccag ttgctgctag agctacaggt tctttggatt cttttttggc tactgaaact      60
ccaatcgcat tgcaaggtgt tttgaacaat attggtccaa acggtgctga tgttgccggt     120
gcttctgctg gtatagttgt tgcttctcca tctagatctg atcccaatta ctttttactct    180
tggactagag atgctgcttt gactgctaaa tacttggttg atgctttcat tgccggtaac     240
aaggatttgg aacaaaccat tcaacagtac atttccgctc aagctaaggt tcaaactatc     300
tctaatccat ccggtgattt gtctactggt ggtttgggtg aacctaagtt caatgttaac     360
gaaactgctt ttactggtcc atggggtaga ccacaaagag atggtccagc tttgagagct     420
actgctttaa ttgcttacgc caactacttg atcgataacg gtgaagcttc tactgctgat     480
gagattattt ggccaatcgt tcaaaacgac ttgtcctaca ttactcagta ctggaactct     540
tctactttcg acttgtggga agaagttgaa ggttcttctt ttttcactac cgccgttcaa     600
catagagctt tggttgaagg taatgctttg gctaccagat gaaccatac ttgttctaac      660
tgtgtttccc aagctccaca agtttttgtgt tccttgcaat cttattggac cggttcttac    720
gttttggcta atttTggtgg ttctggtaga tctggtaagg atgttaattc tatcttgggt     780
tccatccata cttttgatcc tgctggtggt tgtgatgatt ctacttttca accatgttct     840
gcaagagcat ggctaaccaa taaggttgtt actgactctt tcagatccat ctacgctatt     900
aactctggta ttgctgaagg ttcagctgtt gctgttggta gatatcctga gatgtttac      960
caaggtggta atccatggta tttggctaca gctgctgctg cagaacaatt atatgatgct    1020
atctaccagt ggaagaagat cggttctatt tccattaccg atgtgtcttt gccattcttc    1080
```

-continued

```
caagacatat atccatctgc tgcagttggt acttacaact ctggttctac tactttcaac    1140
gatatcatct ctgctgttca aacttacggt gatggttact tgtctatcgt cgaaaagtat    1200
actccatccg atggttcttt gaccgaacaa ttttctagaa ctgatggtac tccattgtct    1260
gcttcagctt tgacttggtc ttatgcttct ttgttgacag cttctgctag aaggcaatct    1320
gttgttccag cttcttgggg tgaatcttct gcttcttcag ttccagctgt tgttctgct     1380 acatctgcta ctggtcctta ttctacagct actaatactg tttggccatc ttctggttca    1440
ggttcttcaa ctactacttc ttctgctcct tgtactactc caacttcagt tgctgttact    1500
ttcgatgaga tcgtttctac ctcttatggt gaaactatct acttggctgg ttccattcca    1560
gaattaggta attggtctac tgcttccgct attccattga gagctgatgc ttacactaat    1620
tctaacccat gtggtacgt taccgttaat ttgccaccag gtacatcttt tgagtacaag    1680
tttttcaaga accagaccga tggtactatc gtttgggaag atgatccaaa cagatcttat    1740
actgttccag catactgtgg tcaaactacc gctattttgg atgattcttg gcagtga       1797
```

```
<210> SEQ ID NO 5
<211> LENGTH: 19
<212> TYPE: PRT
<213> ORGANISM: Artificial Sequence
<220> FEATURE:
<223> OTHER INFORMATION: Signal sequence of Saccharomyces cerevisiae
      alpha-mating factor 1

<400> SEQUENCE: 5

Met Arg Phe Pro Ser Ile Phe Thr Ala Val Leu Phe Ala Ala Ser Ser
1               5                   10                  15

Ala Leu Ala

<210> SEQ ID NO 6
<211> LENGTH: 618
<212> TYPE: PRT
<213> ORGANISM: Rasamsonia emersonii
<220> FEATURE:
<221> NAME/KEY: SIGNAL
<222> LOCATION: (1)..(20)

<400> SEQUENCE: 6

Met Ala Ser Leu Val Ala Gly Ala Leu Cys Ile Leu Gly Leu Thr Pro
1               5                   10                  15

Ala Ala Phe Ala Arg Ala Pro Val Ala Arg Ala Thr Gly Ser Leu
                20                  25                  30

Asp Ser Phe Leu Ala Thr Glu Thr Pro Ile Ala Leu Gln Gly Val Leu
            35                  40                  45

Asn Asn Ile Gly Pro Asn Gly Ala Asp Val Ala Gly Ala Ser Ala Gly
        50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Gln Tyr Ile Ser
            100                 105                 110

Ala Gln Ala Lys Val Gln Thr Ile Ser Asn Pro Ser Gly Asp Leu Ser
        115                 120                 125

Thr Gly Gly Leu Gly Glu Pro Lys Phe Asn Val Asn Glu Thr Ala Phe
    130                 135                 140

Thr Gly Pro Trp Gly Arg Pro Gln Arg Asp Gly Pro Ala Leu Arg Ala
```

```
            145                 150                 155                 160
        Thr Ala Leu Ile Ala Tyr Ala Asn Tyr Leu Ile Asp Asn Gly Glu Ala
                        165                 170                 175
        Ser Thr Ala Asp Glu Ile Ile Trp Pro Ile Val Gln Asn Asp Leu Ser
                        180                 185                 190
        Tyr Ile Thr Gln Tyr Trp Asn Ser Thr Phe Asp Leu Trp Glu Glu
                        195                 200                 205
        Val Glu Gly Ser Ser Phe Phe Thr Thr Ala Val Gln His Arg Ala Leu
                        210                 215                 220
        Val Glu Gly Asn Ala Leu Ala Thr Arg Leu Asn His Thr Cys Ser Asn
        225                 230                 235                 240
        Cys Val Ser Gln Ala Pro Gln Val Leu Cys Phe Leu Gln Ser Tyr Trp
                        245                 250                 255
        Thr Gly Ser Tyr Val Leu Ala Asn Phe Gly Gly Ser Gly Arg Ser Gly
                        260                 265                 270
        Lys Asp Val Asn Ser Ile Leu Gly Ser Ile His Thr Phe Asp Pro Ala
                        275                 280                 285
        Gly Gly Cys Asp Asp Ser Thr Phe Gln Pro Cys Ser Ala Arg Ala Leu
                        290                 295                 300
        Ala Asn His Lys Val Val Thr Asp Ser Phe Arg Ser Ile Tyr Ala Ile
        305                 310                 315                 320
        Asn Ser Gly Ile Ala Glu Gly Ser Ala Val Ala Val Gly Arg Tyr Pro
                        325                 330                 335
        Glu Asp Val Tyr Gln Gly Gly Asn Pro Trp Tyr Leu Ala Thr Ala Ala
                        340                 345                 350
        Ala Ala Glu Gln Leu Tyr Asp Ala Ile Tyr Gln Trp Lys Lys Ile Gly
                        355                 360                 365
        Ser Ile Ser Ile Thr Asp Val Ser Leu Pro Phe Phe Gln Asp Ile Tyr
                        370                 375                 380
        Pro Ser Ala Ala Val Gly Thr Tyr Asn Ser Gly Ser Thr Thr Phe Asn
        385                 390                 395                 400
        Asp Ile Ile Ser Ala Val Gln Thr Tyr Gly Asp Gly Tyr Leu Ser Ile
                        405                 410                 415
        Val Glu Lys Tyr Thr Pro Ser Asp Gly Ser Leu Thr Glu Gln Phe Ser
                        420                 425                 430
        Arg Thr Asp Gly Thr Pro Leu Ser Ala Ser Ala Leu Thr Trp Ser Tyr
                        435                 440                 445
        Ala Ser Leu Leu Thr Ala Ser Ala Arg Arg Gln Ser Val Val Pro Ala
        450                 455                 460
        Ser Trp Gly Glu Ser Ser Ala Ser Ser Val Pro Ala Val Cys Ser Ala
        465                 470                 475                 480
        Thr Ser Ala Thr Gly Pro Tyr Ser Thr Ala Thr Asn Thr Val Trp Pro
                        485                 490                 495
        Ser Ser Gly Ser Gly Ser Ser Thr Thr Thr Ser Ser Ala Pro Cys Thr
                        500                 505                 510
        Thr Pro Thr Ser Val Ala Val Thr Phe Asp Glu Ile Val Ser Thr Ser
                        515                 520                 525
        Tyr Gly Glu Thr Ile Tyr Leu Ala Gly Ser Ile Pro Glu Leu Gly Asn
                        530                 535                 540
        Trp Ser Thr Ala Ser Ala Ile Pro Leu Arg Ala Asp Ala Tyr Thr Asn
        545                 550                 555                 560
        Ser Asn Pro Leu Trp Tyr Val Thr Val Asn Leu Pro Pro Gly Thr Ser
                        565                 570                 575
```

```
Phe Glu Tyr Lys Phe Lys Asn Gln Thr Asp Gly Thr Ile Val Trp
            580                 585                 590

Glu Asp Asp Pro Asn Arg Ser Tyr Thr Val Pro Ala Tyr Cys Gly Gln
        595                 600                 605

Thr Thr Ala Ile Leu Asp Asp Ser Trp Gln
        610                 615

<210> SEQ ID NO 7
<211> LENGTH: 1854
<212> TYPE: DNA
<213> ORGANISM: Artificial Sequence
<220> FEATURE:
<223> OTHER INFORMATION: Encoding SEQ ID NO: 6

<400> SEQUENCE: 7
atgaggttcc catctatttt caccgctgtt ttgtttgctg cttcttctgc tttggctaga      60
gcaccagttg ctgctagagc tacaggttct ttggattctt ttttggctac tgaaactcca     120
atcgcattgc aaggtgtttt gaacaatatt ggtccaaacg tgctgatgt tgccggtgct      180 tctgctggta tagttgttgc ttctccatct agatctgatc ccaattactt ttactcttgg     240
actagagatg ctgctttgac tgctaaatac ttggttgatg ctttcattgc cggtaacaag     300
gatttggaac aaaccattca acagtacatt ccgctcaag ctaaggttca aactatctct      360
aatccatccg tgatttgtc tactggtggt ttgggtgaac taagttcaa tgttaacgaa       420 actgctttta ctggtccatg gggtagacca caaagagatg gtccagcttt gagagctact     480
gctttaattg cttacgccaa ctacttgatc gataacggtg aagcttctac tgctgatgag     540
attatttggc caatcgttca aaacgacttg tcctacatta ctcagtactg aactcttct      600 actttcgact gtgggaaga agttgaaggt tcttcttttt tcactaccgc cgttcaacat      660
agagctttgg ttgaaggtaa tgctttggct accagattga accatacttg ttctaactgt    720
gtttcccaag ctccacaagt tttgtgtttc ttgcaatctt attggaccgg ttcttacgtt    780
ttggctaatt tggtggttc tggtagatct ggtaaggatg ttaattctat cttgggttcc     840
atccatactt tgatcctgc tggtggttgt gatgattcta ctttcaacc atgttctgca      900 agagcattgg ctaaccataa ggttgttact gactctttca gatccatcta cgctattaac   960
tctggtattg ctgaaggttc agctgttgct gttggtagat atcctgaaga tgtttaccaa  1020
ggtggtaatc catggtattt ggctacagct gctgctgcag aacaattata tgatgctatc  1080
taccagtgga agaagatcgg ttctatttcc attaccgatg tgtctttgcc attcttccaa  1140
gacatatatc catctgctgc agttggtact tacaactctg ttctactac tttcaacgat   1200 atcatctctg ctgttcaaac ttacggtgat ggttacttgt ctatcgtcga aaagtatact  1260
ccatccgatg gttctttgac cgaacaattt tctagaactg atggtactcc attgtctgct  1320
tcagctttga cttggtctta tgcttctttg ttgacagctt ctgctagaag gcaatctgtt  1380
gttccagctt cttgggtga tcttctgct tcttcagttc cagctgtttg ttctgctaca     1440
tctgctactg gtccttattc tacagctact aatactgttt ggccatcttc tggttcaggt   1500
tcttcaacta ctacttcttc tgctccttgt actactccaa cttcagttgc tgttactttc   1560
gatgagatcg tttctaccctc ttatggtgaa actatctact ggctggttc cattccagaa  1620 ttaggtaatt ggtctactgc ttccgctatt ccattgagag ctgatgctta cactaattct  1680
aacccattgt ggtacgttac cgttaattgt ccaccaggta catctttga gtacaagttt   1740 ttcaagaacc agaccgatgg tactatcgtt tgggaagatg atccaaacag atcttatact  1800
```

-continued

```
gttccagcat actgtggtca aactaccgct attttggatg attcttggca gtga           1854
```

<210> SEQ ID NO 8
<211> LENGTH: 20
<212> TYPE: PRT
<213> ORGANISM: Artificial Sequence
<220> FEATURE:
<223> OTHER INFORMATION: Signal sequence associated with Rasamsonia
      emersonii glucoamylase from(Uniprot Q9C1V4)

<400> SEQUENCE: 8

Met Ala Ser Leu Val Ala Gly Ala Leu Cys Ile Leu Gly Leu Thr Pro
1               5                   10                  15

Ala Ala Phe Ala
            20

<210> SEQ ID NO 9
<211> LENGTH: 508
<212> TYPE: PRT
<213> ORGANISM: Artificial Sequence
<220> FEATURE:
<223> OTHER INFORMATION: Glucoamylase from Saccharomycopsis fibuligera
      associated with the signal sequence of Saccharomyces cerevisiae
      alpha-mating factor 1
<220> FEATURE:
<221> NAME/KEY: SIGNAL
<222> LOCATION: (1)..(19)

<400> SEQUENCE: 9

Met Arg Phe Pro Ser Ile Phe Thr Ala Val Leu Phe Ala Ala Ser Ser
1               5                   10                  15

Ala Leu Ala Asn Thr Gly His Phe Gln Ala Tyr Ser Gly Tyr Thr Val
            20                  25                  30

Asn Arg Ala Asn Phe Thr Gln Trp Ile His Glu Gln Pro Ala Val Ser
        35                  40                  45

Trp Tyr Tyr Leu Leu Gln Asn Ile Asp Tyr Pro Glu Gly Gln Phe Lys
    50                  55                  60

Ala Ala Lys Pro Gly Val Val Ala Ser Pro Ser Thr Ser Glu Pro
65                  70                  75                  80

Asp Tyr Phe Tyr Gln Trp Thr Arg Asp Thr Ala Ile Thr Phe Leu Ser
                85                  90                  95

Leu Ile Ala Glu Val Glu Asp His Ser Phe Ser Asn Thr Thr Leu Ala
            100                 105                 110

Lys Val Val Glu Tyr Tyr Ile Ser Asn Thr Tyr Thr Leu Gln Arg Val
        115                 120                 125

Ser Asn Pro Ser Gly Asn Phe Asp Ser Pro Asn His Asp Gly Leu Gly
    130                 135                 140

Glu Pro Lys Phe Asn Val Asp Asp Thr Ala Tyr Thr Ala Ser Trp Gly
145                 150                 155                 160

Arg Pro Gln Asn Asp Gly Pro Ala Leu Arg Ala Tyr Ala Ile Ser Arg
                165                 170                 175

Tyr Leu Asn Ala Val Ala Lys His Asn Asn Gly Lys Leu Leu Leu Ala
            180                 185                 190

Gly Gln Asn Gly Ile Pro Tyr Ser Ser Ala Ser Asp Ile Tyr Trp Lys
        195                 200                 205

Ile Ile Lys Pro Asp Leu Gln His Val Ser Thr His Trp Ser Thr Ser
    210                 215                 220

Gly Phe Asp Leu Trp Glu Glu Asn Gln Gly Thr His Phe Phe Thr Ala
225                 230                 235                 240

Leu Val Gln Leu Lys Ala Leu Ser Tyr Gly Ile Pro Leu Ser Lys Thr
                245                 250                 255

Tyr Asn Asp Pro Gly Phe Thr Ser Trp Leu Glu Lys Gln Lys Asp Ala
            260                 265                 270

Leu Asn Ser Tyr Ile Asn Ser Ser Gly Phe Val Asn Ser Gly Lys Lys
        275                 280                 285

His Ile Val Glu Ser Pro Gln Leu Ser Ser Arg Gly Gly Leu Asp Ser
    290                 295                 300

Ala Thr Tyr Ile Ala Ala Leu Ile Thr His Asp Ile Gly Asp Asp Asp
305                 310                 315                 320

Thr Tyr Thr Pro Phe Asn Val Asp Asn Ser Tyr Val Leu Asn Ser Leu
                325                 330                 335

Tyr Tyr Leu Leu Val Asp Asn Lys Asn Arg Tyr Lys Ile Asn Gly Asn
            340                 345                 350

Tyr Lys Ala Gly Ala Ala Val Gly Arg Tyr Pro Glu Asp Val Tyr Asn
        355                 360                 365

Gly Val Gly Thr Ser Glu Gly Asn Pro Trp Gln Leu Ala Thr Ala Tyr
    370                 375                 380

Ala Gly Gln Thr Phe Tyr Thr Leu Ala Tyr Asn Ser Leu Lys Asn Lys
385                 390                 395                 400

Lys Asn Leu Val Ile Glu Lys Leu Asn Tyr Asp Leu Tyr Asn Ser Phe
                405                 410                 415

Ile Ala Asp Leu Ser Lys Ile Asp Ser Ser Tyr Ala Ser Lys Asp Ser
            420                 425                 430

Leu Thr Leu Thr Tyr Gly Ser Asp Asn Tyr Lys Asn Val Ile Lys Ser
        435                 440                 445

Leu Leu Gln Phe Gly Asp Ser Phe Leu Lys Val Leu Leu Asp His Ile
    450                 455                 460

Asp Asp Asn Gly Gln Leu Thr Glu Gly Ile Asn Arg Tyr Thr Gly Phe
465                 470                 475                 480

Gln Ala Gly Ala Val Ser Leu Thr Trp Ser Ser Gly Ser Leu Leu Ser
                485                 490                 495

Ala Asn Arg Ala Arg Asn Lys Leu Ile Glu Leu Leu
            500                 505

<210> SEQ ID NO 10
<211> LENGTH: 1527
<212> TYPE: DNA
<213> ORGANISM: Artificial Sequence
<220> FEATURE:
<223> OTHER INFORMATION: Encoding SEQ ID NO: 9

<400> SEQUENCE: 10
atgaggttcc catctatttt caccgctgtt tgtttgctg cttcttctgc tttggctaac      60
accggtcatt tccaagctta ttctggttat accgttaaca gagctaactt cacccaatgg    120
attcatgaac aaccagctgt tcttggtac tacttgttgc aaaacatcga ttacccagaa     180
ggtcaattca agctgctaa accaggtgtt gttgttgctt ctccatctac atctgaacca     240
gattacttct accaatggac tagagatacc gctattacct tcttgtcctt gattgctgaa    300
gttgaagatc attctttctc caacactacc ttggctaagg ttgtcgaata ttacatttcc    360
aacacctaca ccttgcaaag agtttctaat ccatccggta acttcgattc tccaaatcat    420
gatggtttgg gtgaacctaa gttcaacgtt gatgatactg cttatacagc ttcttggggt    480
agaccacaaa atgatggtcc agctttgaga gcttacgcta tttctagata cttgaacgct    540

```
gttgctaagc acaacaacgg taaattatta ttggccggtc aaaacggtat tccttattct    600
tctgcttccg atatctactg aagattatt aagccagact tgcaacatgt ttctactcat    660
tggtctacct ctggttttga tttgtgggaa gaaaatcaag gtactcattt cttcaccgct    720
ttggttcaat tgaaggcttt gtcttacggt attccattgt ctaagaccta caatgatcca    780
ggtttcactt cttggttgga aaaacaaaag gatgccttga actcctacat taactcttcc    840
ggtttcgtta actctggtaa aaagcacatc gttgaatctc acaattgtc atctagaggt     900 ggtttggatt ctgctactta tattgctgcc ttgatcaccc atgatatcgg tgatgatgat    960
acttacaccc cattcaatgt tgataactcc tacgttttga actccttgta ttacctattg   1020
gtcgacaaca agaacagata caagatcaac ggtaactaca agctggtgc tgctgttggt    1080 agatatcctg aagatgttta caacggtgtt ggtacttctg aaggtaatcc atggcaattg   1140
gctactgctt atgctggtca aacttttttac accttggcct acaattcctt gaagaacaag  1200
aagaacttgg tcatcgaaaa gttgaactac gacttgtaca actccttcat tgctgatttg   1260
tccaagattg attcttccta cgcttctaag gattctttga ctttgaccta cggttccgat   1320
aactacaaga acgttatcaa gtccttgttg caattcggtg actcattctt gaaggttttg   1380
ttggatcaca tcgatgacaa cggtcaattg actgaagaaa tcaacagata caccggtttt   1440
caagctggtg cagtttcttt gacttggtca tctggttctt tgttgtctgc taatagagcc   1500
agaaacaagt tgatcgaatt attgtga                                        1527

<210> SEQ ID NO 11
<211> LENGTH: 616
<212> TYPE: PRT
<213> ORGANISM: Artificial Sequence
<220> FEATURE:
<223> OTHER INFORMATION: Glucoamylase from Rasamsonia emersonii (Uniprot
      A0A0F4YWQ6) associated with the signal sequence of Saccharomyces
      cerevisiae alpha-mating factor 1
<220> FEATURE:
<221> NAME/KEY: SIGNAL
<222> LOCATION: (1)..(19)

<400> SEQUENCE: 11

Met Arg Phe Pro Ser Ile Phe Thr Ala Val Leu Phe Ala Ala Ser Ser
1               5                   10                  15

Ala Leu Ala Arg Ala Pro Val Ala Arg Ala Ser Gly Ser Leu Asp
            20                  25                  30

Ser Phe Leu Ala Thr Glu Thr Pro Ile Ala Leu Gln Gly Val Leu Asn
        35                  40                  45

Asn Ile Gly Pro Asn Gly Ala Asp Val Ala Gly Ala Ser Ala Gly Ile
    50                  55                  60

Val Val Ala Ser Pro Ser Arg Ser Asp Pro Tyr Phe Tyr Ser Trp
65                  70                  75                  80

Thr Arg Asp Ala Ala Leu Thr Ala Lys Tyr Leu Val Asp Ala Phe Ile
                85                  90                  95

Ala Gly Asn Lys Asp Leu Glu Gln Thr Ile Gln Glu Tyr Ile Ser Ala
            100                 105                 110

Gln Ala Gln Val Gln Thr Ile Ser Asn Pro Ser Gly Asp Leu Ser Thr
        115                 120                 125

Gly Gly Leu Gly Glu Pro Lys Phe Asn Val Asn Glu Thr Ala Phe Thr
    130                 135                 140

Gly Pro Trp Gly Arg Pro Gln Arg Asp Gly Pro Ala Leu Arg Ala Thr
145                 150                 155                 160
```

```
Ala Leu Ile Ala Tyr Ala Asn Tyr Leu Ile Asp Asn Gly Gln Ala Ser
                165                 170                 175

Thr Ala Asp Glu Ile Ile Trp Pro Ile Val Gln Asn Asp Leu Ser Tyr
            180                 185                 190

Val Thr Gln Tyr Trp Asn Ser Ser Thr Phe Asp Leu Trp Glu Glu Val
        195                 200                 205

Glu Gly Ser Ser Phe Phe Thr Thr Ala Val Gln His Arg Ala Leu Val
    210                 215                 220

Glu Gly Asn Ala Leu Ala Thr Arg Leu Asn His Thr Cys Pro Asn Cys
225                 230                 235                 240

Val Ser Gln Ala Pro Gln Val Leu Cys Phe Leu Gln Ser Tyr Trp Thr
                245                 250                 255

Gly Ser Tyr Val Leu Ala Asn Phe Gly Gly Ser Gly Arg Ser Gly Lys
            260                 265                 270

Asp Val Asn Ser Ile Leu Gly Ser Ile His Thr Phe Asp Pro Ala Gly
        275                 280                 285

Gly Cys Asp Asp Ser Thr Phe Gln Pro Cys Ser Ala Arg Ala Leu Ala
    290                 295                 300

Asn His Lys Val Val Thr Asp Ser Phe Arg Ser Val Tyr Ala Val Asn
305                 310                 315                 320

Ser Gly Ile Ala Glu Gly Ser Ala Val Ala Val Gly Arg Tyr Pro Glu
                325                 330                 335

Asp Val Tyr Gln Gly Gly Asn Pro Trp Tyr Leu Ala Thr Ala Ala Ala
            340                 345                 350

Ala Glu Gln Leu Tyr Asp Ala Ile Tyr Gln Trp Asn Lys Ile Gly Ser
        355                 360                 365

Ile Ser Ile Thr Asp Val Ser Leu Ala Phe Phe Gln Asp Ile Tyr Pro
    370                 375                 380

Ser Ala Ala Val Gly Thr Tyr Asn Ser Gly Ser Ser Thr Phe Asn Asp
385                 390                 395                 400

Ile Ile Ser Ala Val Gln Thr Tyr Ala Asp Gly Tyr Leu Ser Ile Ile
                405                 410                 415

Glu Lys Tyr Thr Pro Ser Asp Gly Ser Leu Thr Glu Gln Phe Ser Arg
            420                 425                 430

Ser Asp Gly Thr Pro Leu Ser Ala Ser Gly Leu Thr Trp Ser Tyr Ala
        435                 440                 445

Ser Leu Leu Thr Ala Ala Ala Arg Arg Gln Ser Ile Val Pro Ala Ser
    450                 455                 460

Trp Gly Glu Ser Ser Ala Ser Ser Val Pro Ala Val Cys Ser Ala Thr
465                 470                 475                 480

Ser Ala Thr Gly Pro Tyr Ser Thr Ala Thr Asn Thr Ala Trp Pro Ser
                485                 490                 495

Ser Gly Ser Gly Pro Ser Thr Thr Thr Ser Val Pro Cys Thr Thr Pro
            500                 505                 510

Thr Ser Val Ala Val Thr Phe Asp Glu Ile Val Ser Thr Thr Tyr Gly
        515                 520                 525

Glu Thr Ile Tyr Leu Ala Gly Ser Ile Pro Glu Leu Gly Asn Trp Ser
    530                 535                 540

Pro Ser Ser Ala Ile Pro Leu Arg Ala Asp Ala Tyr Thr Ser Ser Asn
545                 550                 555                 560

Pro Leu Trp Tyr Val Thr Leu Asn Leu Pro Ala Gly Thr Ser Phe Glu
                565                 570                 575
```

Tyr Lys Phe Phe Lys Lys Glu Thr Asp Gly Thr Ile Val Trp Glu Asp
            580                 585                 590

Asp Pro Asn Arg Ser Tyr Thr Val Pro Ala Tyr Cys Gly Gln Thr Thr
        595                 600                 605

Ala Ile Leu Asp Asp Ser Trp Gln
    610                 615

<210> SEQ ID NO 12
<211> LENGTH: 1848
<212> TYPE: DNA
<213> ORGANISM: Artificial Sequence
<220> FEATURE:
<223> OTHER INFORMATION: Encoding SEQ ID NO: 11

<400> SEQUENCE: 12

| | | | | | |
|---|---|---|---|---|---|
| atgaggttcc | catctatttt | caccgctgtt | ttgtttgctg | cttcttctgc | tttggctaga | 60 |
| gcgcccgttg | ccgctagagc | ttcaggtagt | ttagatagtt | ttctggctac | tgagacacct | 120 |
| attgcattgc | aagggttct | aaacaacatt | ggaccgaacg | gggcagacgt | ggctggtgct | 180 |
| tccgcaggga | tcgtggttgc | gtctccatca | agaagcgacc | ctgactactt | ttatagttgg | 240 |
| acgagagatg | cggcattaac | agcgaagtat | ttagttgatg | cattcatcgc | cggaaataag | 300 |
| gatttagagc | agactataca | agaatatatc | tcagcgcaag | cacaagtcca | aacgatatcc | 360 |
| aacccatcag | gggacttgtc | aacaggaggt | ctgggtgagc | cgaagtttaa | tgtgaacgag | 420 |
| actgcgttca | ctgggccttg | gggtcgtccc | cagagggatg | ggccagcttt | gcgtgccacg | 480 |
| gctctgattg | cttacgcaaa | ttaccttatc | gacaatggtc | aggcaagtac | cgctgatgaa | 540 |
| ataatttggc | cgattgtcca | gaacgacctt | tcatacgtta | cccagtattg | gaactcttcc | 600 |
| acattcgatt | gtgggagga | agtcgaagga | tccagcttct | ttacaactgc | cgttcagcac | 660 |
| agggctttgg | ttgaaggtaa | tgccttggca | acgcgtttga | accatacgtg | ccctaattgc | 720 |
| gtgtcccaag | ctccacaggt | tttgtgtttc | ctacagagct | attggactgg | ctcctacgtc | 780 |
| ctagcgaatt | ttggcggcag | tgggagatcc | ggaaaagacg | tgaacagcat | cttggggagc | 840 |
| attcacactt | tcgacccagc | tggggctgc | gatgatagta | cgtttcagcc | atgttccgcc | 900 |
| cgtgcattgg | cgaatcataa | ggtggtaact | gacagtttta | ggtcagtata | cgcggttaat | 960 |
| tccgggattg | ctgaagggag | tgctgtagcg | gtgggaaggt | atccagagga | cgtttatcag | 1020 |
| ggtggtaatc | cctggtacct | ggctaccgcc | gctgctgctg | aacaactgta | tgacgccatt | 1080 |
| tatcagtgga | caaaaattgg | ttctatatcc | atccgacg | tctcactagc | ctttttccag | 1140 |
| gatatatatc | caagcgccgc | tgtcggaaca | tacaactccg | gttcatcaac | gttcaatgat | 1200 |
| ataatctccg | ctgtgcaaac | ctacgcggac | ggttacttat | ctattatcga | aaaatacacg | 1260 |
| ccaagtgacg | gtagcctgac | tgagcaattt | agtcgttctg | acggtactcc | attatctgca | 1320 |
| agcggactaa | cgtggagcta | cgcaagccta | cttacagcgg | ccgctcgtag | acaatcaatt | 1380 |
| gtccagcca | gttggggtga | gagttctgcg | agttctgttc | ctgcggtgtg | tagtgcgacg | 1440 |
| tcagcgaccg | gcccttatag | caccgcaaca | aatacggctt | ggccgagttc | cgggtctggt | 1500 |
| ccaagcacaa | cgaccagtgt | cccctgcaca | cccctacat | cagtggccgt | cacttttgac | 1560 |
| gaaatcgtca | gtacgacgta | cggtgaaact | atttatcttg | cggggtcaat | accggagcta | 1620 |
| gggaattggt | caccgagttc | cgcgattcct | ttaagggcag | acgcgtatac | cagtagcaac | 1680 |
| ccgttgtggt | atgttacact | taatctaccc | gcgggcacta | gcttcgagta | caaattcttt | 1740 |
| aaaaagaaa | cggacggcac | gattgtttgg | gaggacgacc | caaaccgttc | ttacactgta | 1800 |

```
ccggcttatt gcggccagac aacagcgatc ttagacgaca gttggcag                         1848
```

<210> SEQ ID NO 13
<211> LENGTH: 597
<212> TYPE: PRT
<213> ORGANISM: Rasamsonia emersonii

<400> SEQUENCE: 13

```
Arg Ala Pro Val Ala Arg Ala Ser Gly Ser Leu Asp Ser Phe Leu
1               5                   10                  15

Ala Thr Glu Thr Pro Ile Ala Leu Gln Gly Val Leu Asn Asn Ile Gly
            20                  25                  30

Pro Asn Gly Ala Asp Val Ala Gly Ala Ser Ala Gly Ile Val Val Ala
        35                  40                  45

Ser Pro Ser Arg Ser Asp Pro Asp Tyr Phe Tyr Ser Trp Thr Arg Asp
50                  55                  60

Ala Ala Leu Thr Ala Lys Tyr Leu Val Asp Ala Phe Ile Ala Gly Asn
65                  70                  75                  80

Lys Asp Leu Glu Gln Thr Ile Gln Glu Tyr Ile Ser Ala Gln Ala Gln
                85                  90                  95

Val Gln Thr Ile Ser Asn Pro Ser Gly Asp Leu Ser Thr Gly Gly Leu
            100                 105                 110

Gly Glu Pro Lys Phe Asn Val Asn Glu Thr Ala Phe Thr Gly Pro Trp
        115                 120                 125

Gly Arg Pro Gln Arg Asp Gly Pro Ala Leu Arg Ala Thr Ala Leu Ile
130                 135                 140

Ala Tyr Ala Asn Tyr Leu Ile Asp Asn Gly Gln Ala Ser Thr Ala Asp
145                 150                 155                 160

Glu Ile Ile Trp Pro Ile Val Gln Asn Asp Leu Ser Tyr Val Thr Gln
                165                 170                 175

Tyr Trp Asn Ser Ser Thr Phe Asp Leu Trp Glu Glu Val Glu Gly Ser
            180                 185                 190

Ser Phe Phe Thr Thr Ala Val Gln His Arg Ala Leu Val Glu Gly Asn
        195                 200                 205

Ala Leu Ala Thr Arg Leu Asn His Thr Cys Pro Asn Cys Val Ser Gln
210                 215                 220

Ala Pro Gln Val Leu Cys Phe Leu Gln Ser Tyr Trp Thr Gly Ser Tyr
225                 230                 235                 240

Val Leu Ala Asn Phe Gly Gly Ser Gly Arg Ser Gly Lys Asp Val Asn
                245                 250                 255

Ser Ile Leu Gly Ser Ile His Thr Phe Asp Pro Ala Gly Gly Cys Asp
            260                 265                 270

Asp Ser Thr Phe Gln Pro Cys Ser Ala Arg Ala Leu Ala Asn His Lys
        275                 280                 285

Val Val Thr Asp Ser Phe Arg Ser Val Tyr Ala Val Asn Ser Gly Ile
290                 295                 300

Ala Glu Gly Ser Ala Val Ala Val Gly Arg Tyr Pro Glu Asp Val Tyr
305                 310                 315                 320

Gln Gly Gly Asn Pro Trp Tyr Leu Ala Thr Ala Ala Ala Glu Gln
                325                 330                 335

Leu Tyr Asp Ala Ile Tyr Gln Trp Asn Lys Ile Gly Ser Ile Ser Ile
            340                 345                 350

Thr Asp Val Ser Leu Ala Phe Phe Gln Asp Ile Tyr Pro Ser Ala Ala
        355                 360                 365
```

-continued

```
Val Gly Thr Tyr Asn Ser Gly Ser Thr Phe Asn Asp Ile Ile Ser
    370             375             380

Ala Val Gln Thr Tyr Ala Asp Gly Tyr Leu Ser Ile Ile Glu Lys Tyr
385             390             395             400

Thr Pro Ser Asp Gly Ser Leu Thr Glu Gln Phe Ser Arg Ser Asp Gly
            405             410             415

Thr Pro Leu Ser Ala Ser Gly Leu Thr Trp Ser Tyr Ala Ser Leu Leu
            420             425             430

Thr Ala Ala Arg Arg Gln Ser Ile Val Pro Ala Ser Trp Gly Glu
            435             440             445

Ser Ser Ala Ser Ser Val Pro Ala Val Cys Ser Ala Thr Ser Ala Thr
    450             455             460

Gly Pro Tyr Ser Thr Ala Thr Asn Thr Ala Trp Pro Ser Ser Gly Ser
465             470             475             480

Gly Pro Ser Thr Thr Thr Ser Val Pro Cys Thr Thr Pro Thr Ser Val
            485             490             495

Ala Val Thr Phe Asp Glu Ile Val Ser Thr Thr Tyr Gly Glu Thr Ile
            500             505             510

Tyr Leu Ala Gly Ser Ile Pro Glu Leu Gly Asn Trp Ser Pro Ser Ser
    515             520             525

Ala Ile Pro Leu Arg Ala Asp Ala Tyr Thr Ser Ser Asn Pro Leu Trp
    530             535             540

Tyr Val Thr Leu Asn Leu Pro Ala Gly Thr Ser Phe Glu Tyr Lys Phe
545             550             555             560

Phe Lys Lys Glu Thr Asp Gly Thr Ile Val Trp Glu Asp Asp Pro Asn
            565             570             575

Arg Ser Tyr Thr Val Pro Ala Tyr Cys Gly Gln Thr Thr Ala Ile Leu
            580             585             590

Asp Asp Ser Trp Gln
            595
```

```
<210> SEQ ID NO 14
<211> LENGTH: 1791
<212> TYPE: DNA
<213> ORGANISM: Artificial Sequence
<220> FEATURE:
<223> OTHER INFORMATION: Encoding SEQ ID NO: 13

<400> SEQUENCE: 14
agagcgcccg ttgccgctag agcttcaggt agtttagata gttttctggc tactgagaca      60
cctattgcat tgcaaggggt tctaaacaac attggaccga acggggcaga cgtggctggt     120
gcttccgcag ggatcgtggt tgcgtctcca tcaagaagcg accctgacta cttttatagt     180
tggacgagag atgcggcatt aacagcgaag tatttagttg atgcattcat cgccggaaat     240
aaggatttag agcagactat acaagaatat atctcagcgc aagcacaagt ccaaacgata     300
tccaacccat caggggactt gtcaacagga ggtctgggtg agccgaagtt taatgtgaac     360
gagactgcgt tcactgggcc ttggggtcgt ccccagaggg atgggccagc tttgcgtgcc     420
acggctctga ttgcttacgc aaattacctt atcgacaatg gtcaggcaag taccgctgat     480
gaaataattt ggccgattgt ccagaacgac ctttcatacg ttacccagta ttggaactct     540
tccacattcg atttgtggga ggaagtcgaa ggatccagct tctttacaac tgccgttcag     600
cacagggctt tggttgaagg taatgccttg gcaacgcgtt tgaaccatac gtgccctaat     660
tgcgtgtccc aagctccaca ggttttgtgt ttcctacaga gctattggac tggctcctac     720
```

```
gtcctagcga attttggcgg cagtgggaga tccggaaaag acgtgaacag catcttgggg      780
agcattcaca ctttcgaccc agctgggggc tgcgatgata gtacgtttca gccatgttcc      840
gcccgtgcat tggcgaatca taaggtggta actgacagtt ttaggtcagt atacgcggtt      900
aattccggga ttgctgaagg gagtgctgta gcggtgggaa ggtatccaga ggacgtttat      960
cagggtggta atccctggta cctggctacc gccgctgctg ctgaacaact gtatgacgcc     1020
atttatcagt ggaacaaaat tggttctata tccatcaccg acgtctcact agcctttttc     1080
caggatatat atccaagcgc cgctgtcgga acatacaact ccggttcatc aacgttcaat     1140
gatataatct ccgctgtgca aacctacgcg gacggttact tatctattat cgaaaaatac     1200
acgccaagtg acggtagcct gactgagcaa tttagtcgtt ctgacggtac tccattatct     1260
gcaagcggac taacgtggag ctacgcaagc ctacttacag cggccgctcg tagacaatca     1320
attgtcccag ccagttgggg tgagagttct gcgagttctg ttcctgcggt gtgtagtgcg     1380
acgtcagcga ccggccctta tagcaccgca acaaatacgg cttggccgag ttccgggtct     1440
ggtccaagca caacgaccag tgtcccctgc acaaccccta catcagtggc cgtcactttt     1500
gacgaaatcg tcagtacgac gtacggtgaa actatttatc ttgcggggtc aataccggag     1560
ctagggaatt ggtcaccgag ttccgcgatt cctttaaggg cagacgcgta taccagtagc     1620
aacccgttgt ggtatgttac acttaatcta cccgcgggca ctagcttcga gtacaaattc     1680
tttaaaaaag aaacggacgg cacgattgtt tgggaggacg acccaaaccg ttcttacact     1740
gtaccggctt attgcggcca gacaacagcg atcttagacg acagttggca g              1791
```

<210> SEQ ID NO 15
<211> LENGTH: 617
<212> TYPE: PRT
<213> ORGANISM: Rasamsonia emersonii
<220> FEATURE:
<221> NAME/KEY: SIGNAL
<222> LOCATION: (1)..(20)

<400> SEQUENCE: 15

```
Met Ala Ser Leu Val Ala Gly Ala Leu Cys Val Leu Gly Leu Thr Pro
1               5                   10                  15

Ala Ala Phe Ala Arg Ala Pro Val Ala Arg Ala Ser Gly Ser Leu
            20                  25                  30

Asp Ser Phe Leu Ala Thr Glu Thr Pro Ile Ala Leu Gln Gly Val Leu
        35                  40                  45

Asn Asn Ile Gly Pro Asn Gly Ala Asp Val Ala Gly Ala Ser Ala Gly
    50                  55                  60

Ile Val Val Ala Ser Pro Ser Arg Ser Asp Pro Asp Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Glu Tyr Ile Ser
            100                 105                 110

Ala Gln Ala Gln Val Gln Thr Ile Ser Asn Pro Ser Gly Asp Leu Ser
        115                 120                 125

Thr Gly Gly Leu Gly Glu Pro Lys Phe Asn Val Asn Glu Thr Ala Phe
    130                 135                 140

Thr Gly Pro Trp Gly Arg Pro Gln Arg Asp Gly Pro Ala Leu Arg Ala
145                 150                 155                 160

Thr Ala Leu Ile Ala Tyr Ala Asn Tyr Leu Ile Asp Asn Gly Gln Ala
                165                 170                 175
```

```
Ser Thr Ala Asp Glu Ile Ile Trp Pro Ile Val Gln Asn Asp Leu Ser
            180                 185                 190

Tyr Val Thr Gln Tyr Trp Asn Ser Thr Phe Asp Leu Trp Glu Glu
        195                 200                 205

Val Glu Gly Ser Ser Phe Phe Thr Thr Ala Val Gln His Arg Ala Leu
    210                 215                 220

Val Glu Gly Asn Ala Leu Ala Thr Arg Leu Asn His Thr Cys Pro Asn
225                 230                 235                 240

Cys Val Ser Gln Ala Pro Gln Val Leu Cys Phe Leu Gln Ser Tyr Trp
                245                 250                 255

Thr Gly Ser Tyr Val Leu Ala Asn Phe Gly Gly Ser Gly Arg Ser Gly
            260                 265                 270

Lys Asp Val Asn Ser Ile Leu Gly Ser Ile His Thr Phe Asp Pro Ala
            275                 280                 285

Gly Gly Cys Asp Asp Ser Thr Phe Gln Pro Cys Ser Ala Arg Ala Leu
    290                 295                 300

Ala Asn His Lys Val Val Thr Asp Ser Phe Arg Ser Val Tyr Ala Val
305                 310                 315                 320

Asn Ser Gly Ile Ala Glu Gly Ser Ala Val Ala Val Gly Arg Tyr Pro
                325                 330                 335

Glu Asp Val Tyr Gln Gly Gly Asn Pro Trp Tyr Leu Ala Thr Ala Ala
            340                 345                 350

Ala Ala Glu Gln Leu Tyr Asp Ala Ile Tyr Gln Trp Asn Lys Ile Gly
        355                 360                 365

Ser Ile Ser Ile Thr Asp Val Ser Leu Ala Phe Phe Gln Asp Ile Tyr
            370                 375                 380

Pro Ser Ala Ala Val Gly Thr Tyr Asn Ser Gly Ser Ser Thr Phe Asn
385                 390                 395                 400

Asp Ile Ile Ser Ala Val Gln Thr Tyr Ala Asp Gly Tyr Leu Ser Ile
                405                 410                 415

Ile Glu Lys Tyr Thr Pro Ser Asp Gly Ser Leu Thr Glu Gln Phe Ser
            420                 425                 430

Arg Ser Asp Gly Thr Pro Leu Ser Ala Ser Gly Leu Thr Trp Ser Tyr
        435                 440                 445

Ala Ser Leu Leu Thr Ala Ala Ala Arg Arg Gln Ser Ile Val Pro Ala
    450                 455                 460

Ser Trp Gly Glu Ser Ser Ala Ser Ser Val Pro Ala Val Cys Ser Ala
465                 470                 475                 480

Thr Ser Ala Thr Gly Pro Tyr Ser Thr Ala Thr Asn Thr Ala Trp Pro
                485                 490                 495

Ser Ser Gly Ser Gly Pro Ser Thr Thr Thr Ser Val Pro Cys Thr Thr
            500                 505                 510

Pro Thr Ser Val Ala Val Thr Phe Asp Glu Ile Val Ser Thr Thr Tyr
        515                 520                 525

Gly Glu Thr Ile Tyr Leu Ala Gly Ser Ile Pro Glu Leu Gly Asn Trp
    530                 535                 540

Ser Pro Ser Ser Ala Ile Pro Leu Arg Ala Asp Ala Tyr Thr Ser Ser
545                 550                 555                 560

Asn Pro Leu Trp Tyr Val Thr Leu Asn Leu Pro Ala Gly Thr Ser Phe
                565                 570                 575

Glu Tyr Lys Phe Phe Lys Lys Glu Thr Asp Gly Thr Ile Val Trp Glu
            580                 585                 590
```

```
Asp Asp Pro Asn Arg Ser Tyr Thr Val Pro Ala Tyr Cys Gly Gln Thr
            595                 600                 605

Thr Ala Ile Leu Asp Asp Ser Trp Gln
    610                 615

<210> SEQ ID NO 16
<211> LENGTH: 20
<212> TYPE: PRT
<213> ORGANISM: Artificial Sequence
<220> FEATURE:
<223> OTHER INFORMATION: Signal sequence associated with Rasamsonia
      emersonii glucoamylase (Uniprot A0A0F4YWQ6)

<400> SEQUENCE: 16

Met Ala Ser Leu Val Ala Gly Ala Leu Cys Val Leu Gly Leu Thr Pro
1               5                   10                  15

Ala Ala Phe Ala
            20

<210> SEQ ID NO 17
<211> LENGTH: 471
<212> TYPE: PRT
<213> ORGANISM: Rhizomucor pusillus
<220> FEATURE:
<221> NAME/KEY: SIGNAL
<222> LOCATION: (1)..(21)

<400> SEQUENCE: 17

Met Lys Phe Ser Ile Ser Leu Ser Ala Ala Ile Val Leu Phe Ala Ala
1               5                   10                  15

Ala Thr Ser Leu Ala Ser Pro Leu Pro Gln Gln Gln Arg Tyr Ala Lys
            20                  25                  30

Arg Ala Thr Ser Asp Asp Trp Lys Ser Lys Ala Ile Tyr Gln Leu Leu
        35                  40                  45

Thr Asp Arg Phe Gly Arg Ala Asp Asp Ser Thr Ser Asn Cys Ser Asn
    50                  55                  60

Leu Ser Asn Tyr Cys Gly Gly Thr Tyr Glu Gly Ile Thr Lys His Leu
65                  70                  75                  80

Asp Tyr Ile Ser Gly Met Gly Phe Asp Ala Ile Trp Ile Ser Pro Ile
                85                  90                  95

Pro Lys Asn Ser Asp Gly Gly Tyr His Gly Tyr Trp Ala Thr Asp Phe
            100                 105                 110

Tyr Gln Leu Asn Ser Asn Phe Gly Asp Glu Ser Gln Leu Lys Thr Leu
        115                 120                 125

Ile Gln Ala Ala His Glu Arg Gly Met Tyr Val Met Leu Asp Val Val
    130                 135                 140

Ala Asn His Ala Gly Pro Thr Ser Asn Gly Tyr Ser Gly Tyr Thr Phe
145                 150                 155                 160

Gly Asp Ala Ser Leu Tyr His Pro Lys Cys Thr Ile Asp Tyr Asn Asp
                165                 170                 175

Gln Thr Ser Ile Glu Gln Cys Trp Val Ala Asp Glu Leu Pro Asp Ile
            180                 185                 190

Asp Thr Glu Asn Ser Asp Asn Val Ala Ile Leu Asn Asp Ile Val Ser
        195                 200                 205

Gly Trp Val Gly Asn Tyr Ser Phe Asp Gly Ile Arg Ile Asp Thr Val
    210                 215                 220

Lys His Ile Arg Lys Asp Phe Trp Thr Gly Tyr Ala Glu Ala Ala Gly
225                 230                 235                 240
```

```
Val Phe Ala Thr Gly Glu Val Phe Asn Gly Asp Pro Ala Tyr Val Gly
                245                 250                 255

Pro Tyr Gln Lys Tyr Leu Pro Pro Leu Ile Asn Tyr Pro Met Tyr Tyr
            260                 265                 270

Ala Leu Asn Asp Val Phe Val Ser Lys Ser Lys Gly Phe Ser Arg Ile
        275                 280                 285

Ser Glu Met Leu Gly Ser Asn Arg Asn Ala Phe Glu Asp Thr Ser Val
    290                 295                 300

Leu Thr Thr Phe Val Asp Asn His Asp Asn Pro Arg Phe Leu Asn Ser
305                 310                 315                 320

Gln Ser Asp Lys Ala Leu Phe Lys Asn Ala Leu Thr Tyr Val Leu Leu
                325                 330                 335

Gly Glu Gly Ile Pro Ile Val Tyr Tyr Gly Ser Glu Gln Gly Phe Ser
            340                 345                 350

Gly Gly Ala Asp Pro Ala Asn Arg Glu Val Leu Trp Thr Ala Asn Tyr
        355                 360                 365

Asp Thr Ser Ser Asp Leu Tyr Gln Phe Ile Lys Thr Val Asn Ser Val
    370                 375                 380

Arg Met Lys Ser Asn Lys Thr Val Tyr Met Asp Ile Tyr Val Gly Asp
385                 390                 395                 400

Asn Ala Tyr Ala Phe Lys His Gly Asp Ala Leu Val Val Leu Asn Asn
                405                 410                 415

Tyr Gly Ser Gly Ser Thr Asn Gln Val Ser Phe Ser Val Ser Gly Lys
            420                 425                 430

Phe Asp Ser Gly Ala Ser Leu Met Asp Ile Val Ser Asn Ile Thr Thr
        435                 440                 445

Thr Val Ser Ser Asp Gly Thr Val Thr Phe Asn Leu Lys Asp Gly Leu
    450                 455                 460

Pro Ala Ile Phe Thr Ser Ala
465                 470

<210> SEQ ID NO 18
<211> LENGTH: 615
<212> TYPE: PRT
<213> ORGANISM: Aspergillus luchuensis
<220> FEATURE:
<221> NAME/KEY: SIGNAL
<222> LOCATION: (1)..(21)

<400> SEQUENCE: 18

Met Asp Gly Trp Trp Ile Ile Ser Leu Leu Val Val Thr Leu Gly Phe
1               5                   10                  15

Ser Thr Val Asn Ala Ala Ser Arg Asp Gln Trp Ile Gly Arg Ser Ile
            20                  25                  30

Tyr Gln Ile Val Thr Asp Arg Phe Ala Arg Ser Asp Asn Ser Thr Thr
        35                  40                  45

Ala Ala Cys Asp Ala Ala Gln Gly Asn Tyr Cys Gly Gly Ser Phe Gln
    50                  55                  60

Gly Ile Ile Asn Lys Leu Asp Tyr Ile His Asp Leu Gly Phe Asp Ala
65                  70                  75                  80

Val Gly Leu Ala Leu Gln Ser Ser Val Pro His Thr Phe Cys Asn Ser
                85                  90                  95

Ser His Ile Gln Val Ser Arg Tyr Gly Ser Leu Gln Arg Lys Pro Arg
            100                 105                 110

Phe Pro Pro Glu Gln Gln Ile Ser Gln Phe Ile Ala Tyr His Gly Tyr
        115                 120                 125
```

-continued

Trp Pro Asn Asp Leu Tyr Ser Ile Asn Ser His Phe Gly Thr Pro Lys
130                 135                 140

Glu Leu Gln Ala Leu Ser Ser Ala Leu His Asn Arg Gly Met Tyr Leu
145                 150                 155                 160

Met Leu Asp Ile Val Val Gly Asp Met Ala Trp Ala Gly Asn Ser Ser
                165                 170                 175

Thr Val Asp Tyr Ser Thr Phe Asn Pro Phe Asp Asp Glu Lys Tyr Phe
                180                 185                 190

His Asp Phe Lys Leu Leu Ser Ser Asp Pro Thr Asn Glu Thr Cys Val
            195                 200                 205

Leu Asp Cys Trp Met Gly Asp Thr Val Val Ser Leu Pro Asp Leu Arg
210                 215                 220

Asn Glu Asp Asp Gln Val Gln Asn Ile Leu Gly Ser Trp Ile Ser Gly
225                 230                 235                 240

Leu Val Ser Asn Tyr Ser Ile Asp Gly Leu Arg Ile Asp Ser Val Leu
                245                 250                 255

Asn Ile Ala Pro Asp Phe Phe Ser Asn Phe Thr Lys Ser Ser Gly Val
                260                 265                 270

Phe Thr Ile Gly Glu Gly Ala Thr Ala Asp Ala Ala Asp Val Cys Pro
                275                 280                 285

Leu Gln Pro Ser Leu Asn Gly Leu Leu Asn Tyr Pro Phe Leu Ser Arg
290                 295                 300

Val Asp Leu Leu Arg Tyr Tyr Ile Leu Thr Asn Ala Phe Asn Thr Thr
305                 310                 315                 320

Asn Gly Asn Leu Ser Thr Ile Thr Glu Ser Ile Ser Tyr Thr Lys Gly
                325                 330                 335

Gln Cys Glu Asp Val Leu Ala Leu Gly Thr Phe Thr Ala Asn Gln Asp
                340                 345                 350

Val Pro Arg Phe Gly Ser Tyr Thr Ser Asp Ile Ser Gln Tyr Ala Gly
                355                 360                 365

Gly Arg His Pro His Pro Tyr Val Pro Ile Pro Thr Pro His Arg Arg
370                 375                 380

Gln Asp Phe Ser Asp Thr Thr Asp Asp Gln Asn Thr Val Tyr Tyr Gly
385                 390                 395                 400

Glu Glu Gln His Leu Thr Gly Ser Tyr Asn Pro Val Asn Arg Glu Ala
                405                 410                 415

Leu Trp Leu Thr Asn Tyr Ser Met His Ser Thr Ser Leu Pro Ala Leu
                420                 425                 430

Val Lys Ser Leu Asn Arg Leu Arg Ser Tyr Ala Ser Gly Asp Gly Glu
435                 440                 445

Gln Tyr Thr Gln Asn Ser Gln Ser Gly Ser Asp Tyr Leu Ser Tyr Leu
450                 455                 460

Ser Ala Pro Ile Tyr Asn Ser Thr His Ile Leu Ala Thr Arg Lys Gly
465                 470                 475                 480

Phe Ala Gly Asn Gln Val Ser Val Val Ser Asn Leu Gly Ala Lys
                485                 490                 495

Pro Ala Ser Lys Ala Ala Thr Lys Ile Thr Leu Gly Ser Asp Glu Thr
                500                 505                 510

Gly Phe Gln Ser Lys Gln Asn Val Thr Glu Ile Leu Ser Cys Lys Thr
            515                 520                 525

Tyr Val Thr Asp Ser Ser Gly Asn Leu Ala Val Asp Leu Ser Ser Asp
530                 535                 540

Gly Gly Pro Arg Val Tyr Tyr Pro Thr Asp Ser Leu Lys Asp Ser Thr
545                 550                 555                 560

Asp Ile Cys Asp Asp Gln Thr Lys Ser Ala Thr Pro Ser Ser Ser Ala
            565                 570                 575

Ala Ser Ser Val Ser Pro Asn Gln Ser Lys Gly Ser Glu Thr Cys Leu
        580                 585                 590

Phe Gly Val Pro Leu Gly Ile Ser Thr Leu Val Val Thr Val Ala Met
    595                 600                 605

Ala Thr Ser Tyr Ala Phe Ile
    610                 615

<210> SEQ ID NO 19
<211> LENGTH: 549
<212> TYPE: PRT
<213> ORGANISM: Aspergillus oryzae
<220> FEATURE:
<221> NAME/KEY: SIGNAL
<222> LOCATION: (1)..(23)

<400> SEQUENCE: 19

Met Val Ser Ser Ser Leu Gly Arg Phe Ala Val Leu Val Thr Ser
1               5                   10                  15

Leu Val Gly Ser Ala Val Ala Ala Thr Thr Ala Glu Trp Lys Ser Arg
            20                  25                  30

Ser Val Tyr Gln Thr Met Thr Asp Arg Phe Ala Arg Thr Asp Gly Ser
        35                  40                  45

Thr Thr Ala Pro Cys Asn Thr Thr Gln Gly Leu Tyr Cys Gly Gly Thr
    50                  55                  60

Trp Arg Gly Thr Ile Asp Lys Leu Asp Tyr Ile Gln Gly Met Gly Phe
65                  70                  75                  80

Asp Ala Val Met Ile Ser Pro Ile Val Glu Asn Ile Glu Gly Arg Val
                85                  90                  95

Ser Tyr Gly Glu Ala Tyr His Gly Tyr Trp Pro Leu Asp Leu Tyr Ser
            100                 105                 110

Leu Asn Ser His Phe Gly Thr His Gln Asp Leu Leu Asp Leu Ser Glu
        115                 120                 125

Ala Leu His Ser Arg Gly Met Tyr Leu Met Met Asp Thr Val Ile Asn
    130                 135                 140

Asn Met Ala Tyr Met Thr Asn Gly Lys Asp Pro Ala Lys Asn Ile Asp
145                 150                 155                 160

Tyr Ser Val Phe Thr Pro Phe Asn Asp Ser Ser Tyr Phe His Pro Tyr
                165                 170                 175

Cys Lys Ile Thr Asp Trp Asn Asn Tyr Thr Asn Ala Gln Leu Cys Gln
            180                 185                 190

Thr Gly Asp Asp Lys Val Ala Leu Pro Asp Leu Phe Thr Glu His Glu
        195                 200                 205

Asp Val Gln Gln Ile Leu Glu Lys Trp Ala Lys Glu Ile Ile Ser Thr
    210                 215                 220

Tyr Ser Ile Asp Gly Leu Arg Ile Asp Ala Ala Lys His Val Asn Pro
225                 230                 235                 240

Gly Phe Leu Lys Asn Phe Gly Asp Ala Ile Gly Ala Phe Met Thr Gly
                245                 250                 255

Glu Val Leu Gln Gln Glu Val Asp Thr Ile Cys Lys Tyr Gln Asn Asn
            260                 265                 270

Tyr Ile Gly Ser Val Pro Asn Tyr Pro Ile Tyr Tyr Ser Val Leu Lys
        275                 280                 285

```
Ala Phe Thr Leu Gly Asn Thr Thr Asp Leu Ala Asn Gln Val Glu Ile
    290                 295                 300

Met Lys Asn Ser Cys Asp Asp Val Thr Ala Leu Ala Ser Phe Ser Glu
305                 310                 315                 320

Asn His Asp Val Ala Arg Phe Ala Ser Met Thr Asp Asp Met Ala Leu
                325                 330                 335

Ala Lys Asn Val Leu Thr Phe Thr Ile Leu Tyr Asp Gly Val Pro Met
                340                 345                 350

Ile Tyr Gln Gly Gln Glu Gln His Leu Asp Gly Pro Gly Thr Pro Asp
                355                 360                 365

Asn Arg Glu Ala Ile Trp Leu Thr Lys Tyr Asn Thr Asp Ala Glu Leu
    370                 375                 380

Tyr Lys Leu Ile Ala Lys Leu Asn Thr Ile Arg Lys His Ala Tyr Lys
385                 390                 395                 400

Leu Asp Pro Asn Tyr Val Ser Leu Gln Thr Tyr Pro Ile Phe Arg Gly
                405                 410                 415

Gly Ser Glu Leu Gly Phe Arg Lys Gly Val Glu Gly Arg Gln Val Val
                420                 425                 430

Met Leu Leu Ser Thr Gln Gly Ser Asn Ser Ser Ala Tyr Asn Leu Thr
                435                 440                 445

Leu Pro Val Ser Phe Asn Gly Gly Val Gln Val Met Asp Val Leu Asn
    450                 455                 460

Cys Val Asn Tyr Thr Val Asn Pro Gln Ser Glu Leu Ile Val Pro Met
465                 470                 475                 480

Asp Lys Gly Glu Pro Arg Val Phe Phe Pro Thr Ser Leu Met Pro Gly
                485                 490                 495

Ser Gly Leu Cys Gly Tyr Thr Thr Ala Asn Val Ser Phe Val Glu Leu
                500                 505                 510

Lys Thr Lys Gly Ala Ala Ala Met Ser Leu Gly Ala Lys Thr Thr
    515                 520                 525

Ser Ser Ala Ala His Gly Val Leu Leu Ser Val Leu Leu Ser Ser Leu
    530                 535                 540

Val Ala Val Leu Leu
545

<210> SEQ ID NO 20
<211> LENGTH: 515
<212> TYPE: PRT
<213> ORGANISM: Homo sapiens
<220> FEATURE:
<221> NAME/KEY: SIGNAL
<222> LOCATION: (1)..(19)

<400> SEQUENCE: 20

Met Leu Leu Gln Ala Phe Leu Phe Leu Leu Ala Gly Phe Ala Ala Lys
1               5                   10                  15

Ile Ser Ala Gln Tyr Ser Pro Asn Thr Gln Gln Gly Arg Thr Ser Ile
                20                  25                  30

Val His Leu Phe Glu Trp Arg Trp Val Asp Ile Ala Leu Glu Cys Glu
            35                  40                  45

Arg Tyr Leu Ala Pro Lys Gly Phe Gly Gly Val Gln Val Ser Pro Pro
        50                  55                  60

Asn Glu Asn Val Ala Ile Tyr Asn Pro Phe Arg Pro Trp Trp Glu Arg
65                  70                  75                  80

Tyr Gln Pro Val Ser Tyr Lys Leu Cys Thr Arg Ser Gly Asn Glu Asp
```

```
                     85                  90                  95
Glu Phe Arg Asn Met Val Thr Arg Cys Asn Asn Val Gly Val Arg Ile
                100                 105                 110
Tyr Val Asp Ala Val Ile Asn His Met Cys Gly Asn Ala Val Ser Ala
                115                 120                 125
Gly Thr Ser Ser Thr Cys Gly Ser Tyr Phe Asn Pro Gly Ser Arg Asp
            130                 135                 140
Phe Pro Ala Val Pro Tyr Ser Gly Trp Asp Phe Asn Asp Gly Lys Cys
145                 150                 155                 160
Lys Thr Gly Ser Gly Asp Ile Glu Asn Tyr Asn Asp Ala Thr Gln Val
                165                 170                 175
Arg Asp Cys Arg Leu Thr Gly Leu Leu Asp Leu Ala Leu Glu Lys Asp
                180                 185                 190
Tyr Val Arg Ser Lys Ile Ala Glu Tyr Met Asn His Leu Ile Asp Ile
                195                 200                 205
Gly Val Ala Gly Phe Arg Leu Asp Ala Ser Lys His Met Trp Pro Gly
            210                 215                 220
Asp Ile Lys Ala Ile Leu Asp Lys Leu His Asn Leu Asn Ser Asn Trp
225                 230                 235                 240
Phe Pro Ala Gly Ser Lys Pro Phe Ile Tyr Gln Glu Val Ile Asp Leu
                245                 250                 255
Gly Gly Glu Pro Ile Lys Ser Ser Asp Tyr Phe Gly Asn Gly Arg Val
                260                 265                 270
Thr Glu Phe Lys Tyr Gly Ala Lys Leu Gly Thr Val Ile Arg Lys Trp
            275                 280                 285
Asn Gly Glu Lys Met Ser Tyr Leu Lys Asn Trp Gly Glu Gly Trp Gly
            290                 295                 300
Phe Val Pro Ser Asp Arg Ala Leu Val Phe Val Asp Asn His Asp Asn
305                 310                 315                 320
Gln Arg Gly His Gly Ala Gly Gly Ala Ser Ile Leu Thr Phe Trp Asp
                325                 330                 335
Ala Arg Leu Tyr Lys Met Ala Val Gly Phe Met Leu Ala His Pro Tyr
                340                 345                 350
Gly Phe Thr Arg Val Met Ser Ser Tyr Arg Trp Pro Arg Gln Phe Gln
            355                 360                 365
Asn Gly Asn Asp Val Asn Asp Trp Val Gly Pro Pro Asn Asn Asn Gly
            370                 375                 380
Val Ile Lys Glu Val Thr Ile Asn Pro Asp Thr Thr Cys Gly Asn Asp
385                 390                 395                 400
Trp Val Cys Glu His Arg Trp Arg Gln Ile Arg Asn Met Val Ile Phe
                405                 410                 415
Arg Asn Val Val Asp Gly Gln Pro Phe Thr Asn Trp Tyr Asp Asn Gly
                420                 425                 430
Ser Asn Gln Val Ala Phe Gly Arg Gly Asn Arg Gly Phe Ile Val Phe
                435                 440                 445
Asn Asn Asp Asp Trp Ser Phe Ser Leu Thr Leu Gln Thr Gly Leu Pro
                450                 455                 460
Ala Gly Thr Tyr Cys Asp Val Ile Ser Gly Asp Lys Ile Asn Gly Asn
465                 470                 475                 480
Cys Thr Gly Ile Lys Ile Tyr Val Ser Asp Asp Gly Lys Ala His Phe
                485                 490                 495
Ser Ile Ser Asn Ser Ala Glu Asp Pro Phe Ile Ala Ile His Ala Glu
                500                 505                 510
```

Ser Lys Leu
    515

<210> SEQ ID NO 21
<211> LENGTH: 555
<212> TYPE: PRT
<213> ORGANISM: Aspergillus niger
<220> FEATURE:
<221> NAME/KEY: SIGNAL
<222> LOCATION: (1)..(25)

<400> SEQUENCE: 21

Met Val Ser Met Ser Ala Leu Arg His Gly Leu Gly Val Leu Tyr Leu
1               5                   10                  15

Ala Ser Trp Leu Gly Ser Ser Leu Ala Ala Ser Thr Glu Gln Trp Lys
            20                  25                  30

Ser Arg Ser Ile Tyr Gln Thr Met Thr Asp Arg Phe Ala Arg Thr Asp
        35                  40                  45

Gly Ser Thr Thr Ser Pro Cys Asn Thr Thr Glu Gly Leu Tyr Cys Gly
    50                  55                  60

Gly Thr Trp Arg Gly Met Ile Asn His Leu Asp Tyr Ile Gln Gly Met
65                  70                  75                  80

Gly Phe Asp Ala Val Met Ile Ser Pro Ile Ile Glu Asn Val Glu Gly
                85                  90                  95

Arg Val Glu Tyr Gly Glu Ala Tyr His Gly Tyr Trp Pro Val Asp Leu
            100                 105                 110

Tyr Ser Leu Asn Ser His Phe Gly Thr His Gln Asp Leu Leu Asp Leu
        115                 120                 125

Ser Asp Ala Leu His Ala Arg Asp Met Tyr Leu Met Met Asp Thr Val
    130                 135                 140

Ile Asn Asn Met Ala Tyr Ile Thr Asn Gly Ser Asp Pro Ala Thr His
145                 150                 155                 160

Ile Asp Tyr Ser Thr Leu Thr Pro Phe Asn Ser Ser Tyr Tyr His
                165                 170                 175

Pro Tyr Cys Lys Ile Thr Asp Trp Asn Asn Phe Thr Asn Ala Gln Leu
            180                 185                 190

Cys Gln Thr Gly Asp Asn Ile Val Ala Leu Pro Asp Leu Tyr Thr Glu
        195                 200                 205

His Ala Glu Val Gln Glu Thr Leu Ser Asn Trp Ala Lys Glu Val Ile
    210                 215                 220

Ser Thr Tyr Ser Ile Asp Gly Leu Arg Ile Asp Ala Ala Lys His Val
225                 230                 235                 240

Asn Pro Gly Phe Leu Lys Asn Phe Gly Asp Ala Leu Asp Ile Phe Met
                245                 250                 255

Thr Gly Glu Val Leu Gln Gln Glu Val Ser Thr Ile Cys Asp Tyr Gln
            260                 265                 270

Asn Asn Tyr Ile Gly Ser Leu Pro Asn Tyr Pro Val Tyr Tyr Ala Met
        275                 280                 285

Leu Lys Ala Phe Thr Leu Gly Asn Thr Ser Ala Leu Ala Thr Gln Val
    290                 295                 300

Gln Ser Met Lys Asn Ser Cys Asn Asp Val Thr Ala Leu Ser Ser Phe
305                 310                 315                 320

Ser Glu Asn His Asp Val Ala Arg Phe Ala Ser Met Thr His Asp Met
                325                 330                 335

Ala Leu Ala Lys Asn Ile Leu Thr Phe Thr Leu Leu Phe Asp Gly Val 340                 345                 350
Pro Met Ile Tyr Gln Gly Gln Glu Gln His Leu Asp Gly Pro Gly Ser
            355                 360                 365

Pro Glu Asn Arg Glu Ala Ile Trp Leu Ser Glu Tyr Asn Thr Asp Ala
    370                 375                 380

Glu Leu Tyr Lys Leu Ile Gly Lys Leu Asn Ala Ile Arg Lys His Ala
385                 390                 395                 400

Tyr Arg Leu Asp Asn His Tyr Pro Asp Val Glu Thr Tyr Pro Ile Phe
            405                 410                 415

Glu Gly Gly Ser Glu Leu Gly Phe Arg Lys Gly Ile Glu Gly Arg Gln
        420                 425                 430

Val Val Met Leu Leu Ser Thr Gln Gly Thr Asn Ser Ser Ala Tyr Asn
            435                 440                 445

Leu Ser Met Pro Val Ser Phe Thr Gly Gly Thr Val Val Thr Glu Ile
        450                 455                 460

Leu Asn Cys Val Asn Tyr Thr Val Asn Thr Gln Ser Glu Leu Val Val
465                 470                 475                 480

Pro Met Asp Lys Gly Glu Pro Arg Val Phe Phe Pro Ala Asp Leu Met
            485                 490                 495

Pro Gly Ser Gly Leu Cys Gly Leu Pro Val Ala Asn Val Thr Tyr Ala
        500                 505                 510

Ala Leu Arg Thr Gln Gly Ala Ala Ala Glu Ala Ala Leu Ser Leu
            515                 520                 525

Gly Ile Lys Thr Asp Ala Ala Ser Ser Ala Leu Leu Ser Leu Gly Leu
        530                 535                 540

Ser Val Val Ala Gly Leu Ile Val Gly Met Trp
545                 550                 555

<210> SEQ ID NO 22
<211> LENGTH: 567
<212> TYPE: PRT
<213> ORGANISM: Aspergillus niger
<220> FEATURE:
<221> NAME/KEY: SIGNAL
<222> LOCATION: (1)..(22)

<400> SEQUENCE: 22

Met Asp Asp Gly Trp Trp Ile Ile Ser Leu Leu Val Val Thr Leu Gly
1               5                   10                  15

Ile Pro Thr Val Asn Ala Ala Ser Arg Asp Gln Trp Ile Gly Arg Ser
            20                  25                  30

Ile Tyr Gln Ile Val Thr Asp Arg Phe Ala Arg Ser Asp Asn Ser Thr
        35                  40                  45

Thr Ala Ala Cys Asp Ala Ala Leu Gly Asn Tyr Cys Gly Gly Ser Phe
    50                  55                  60

Gln Gly Ile Ile Asn Lys Leu Asp Tyr Ile Gln Glu Leu Gly Phe Asp
65              70                  75                  80

Ala Ile Trp Ile Ser Pro Ala Gln Ser Gln Ile Ser Ala Arg Thr Ala
            85                  90                  95

Asp Leu Ser Ala Tyr His Gly Tyr Trp Pro Asn Asp Leu Tyr Ser Ile
        100                 105                 110

Asn Ser His Phe Gly Thr Pro Lys Glu Leu Glu Ala Leu Ser Ser Ala
    115                 120                 125

Leu His Asp Arg Gly Met Tyr Leu Met Leu Asp Ile Val Val Gly Asp
        130                 135                 140

```
Met Ala Trp Ala Gly Asn His Ser Thr Val Asp Tyr Ser Asn Phe Asn
145                 150                 155                 160

Pro Phe Asn Asp Gln Lys Phe His Asp Phe Lys Leu Leu Ser Ser
            165                 170                 175

Asp Pro Thr Asn Glu Thr Cys Val Leu Asp Cys Trp Met Gly Asp Thr
                180                 185                 190

Val Val Ser Leu Pro Asp Leu Arg Asn Glu Asp Gln Gln Val Gln Asn
        195                 200                 205

Ile Leu Gly Thr Trp Ile Ser Gly Leu Val Ser Asn Tyr Ser Ile Asp
        210                 215                 220

Gly Leu Arg Ile Asp Ser Val Leu Asn Ile Ala Pro Asp Phe Phe Ser
225                 230                 235                 240

Asn Phe Thr Lys Ser Ser Gly Val Phe Thr Val Gly Glu Gly Ala Thr
                245                 250                 255

Ala Asp Ala Ala Asp Val Cys Pro Leu Gln Pro Ser Leu Asn Gly Leu
            260                 265                 270

Leu Asn Tyr Pro Leu Tyr Tyr Ile Leu Thr Asp Ala Phe Asn Thr Thr
        275                 280                 285

Asn Gly Asn Leu Ser Thr Ile Thr Glu Ser Ile Ser Tyr Thr Lys Gly
        290                 295                 300

Gln Cys Glu Asp Val Leu Ala Leu Gly Thr Phe Thr Ala Asn Gln Asp
305                 310                 315                 320

Val Pro Arg Phe Gly Ser Tyr Thr Ser Asp Ile Ser Leu Ala Arg Asn
                325                 330                 335

Ile Leu Thr Ser Ser Met Leu Thr Asp Gly Ile Pro Ile Leu Tyr Tyr
            340                 345                 350

Gly Glu Glu Gln His Leu Thr Gly Ser Tyr Asn Pro Val Asn Arg Glu
        355                 360                 365

Ala Leu Trp Leu Thr Asn Tyr Ser Met Arg Ser Thr Ser Leu Pro Thr
        370                 375                 380

Leu Val Gln Ser Leu Asn Arg Leu Arg Ser Tyr Ala Ser Gly Asp Gly
385                 390                 395                 400

Glu Gln Tyr Thr Gln Lys Ser Gln Ser Gly Ser Asp Tyr Leu Ser Tyr
                405                 410                 415

Leu Ser Ala Pro Ile Tyr Asn Ser Thr His Ile Leu Ala Thr Arg Lys
            420                 425                 430

Gly Phe Ala Gly Asn Gln Ile Val Ser Val Val Ser Asn Leu Gly Ala
        435                 440                 445

Lys Pro Ala Ser Lys Ala Thr Thr Lys Ile Thr Leu Gly Ser Asp Glu
450                 455                 460

Thr Gly Phe Gln Ser Lys Gln Asn Val Thr Glu Ile Leu Ser Cys Lys
465                 470                 475                 480

Thr Tyr Val Thr Asp Ser Ser Gly Asn Leu Ala Val Asp Leu Ser Ser
                485                 490                 495

Asp Gly Gly Pro Arg Val Tyr Tyr Pro Thr Ser Leu Lys Asp Ser
            500                 505                 510

Thr Asp Ile Cys Gly Asp Gln Thr Lys Ser Ala Thr Pro Ser Ser Ser
        515                 520                 525

Ala Ala Ser Ser Ala Ser Leu Thr Gln Ser Lys Gly Ser Glu Thr Cys
        530                 535                 540

Leu Phe Gly Val Pro Leu Gly Ile Ser Thr Leu Val Val Thr Val Ala
545                 550                 555                 560

Met Ala Thr Ser Tyr Val Phe
```

565

<210> SEQ ID NO 23
<211> LENGTH: 550
<212> TYPE: PRT
<213> ORGANISM: Aspergillus niger
<220> FEATURE:
<221> NAME/KEY: SIGNAL
<222> LOCATION: (1)..(29)

<400> SEQUENCE: 23

Met Met Phe Arg Lys Ser Ala Ser Leu Leu Gly Gln Arg Leu Met Ala
1               5                   10                  15

Val Cys Leu Leu Cys Trp Cys Val Ser Leu Ala Thr Ala Ala Ser Thr
            20                  25                  30

Glu Glu Trp Lys Thr Arg Ser Ile Tyr Gln Thr Met Thr Asp Arg Phe
        35                  40                  45

Ala Leu Thr Asn Gly Ser Thr Thr Ala Pro Cys Asn Thr Thr Val Ala
    50                  55                  60

Asn Tyr Cys Gly Gly Ser Trp Gln Gly Thr Ile Asp Lys Leu Asp Tyr
65                  70                  75                  80

Ile Gln Gly Met Gly Phe Asp Ala Ile Met Ile Ser Pro Val Ile Lys
                85                  90                  95

Asn Ile Ala Gly Arg Ser Lys Asp Gly Glu Ala Tyr His Gly Tyr Trp
            100                 105                 110

Pro Leu Asp Leu Tyr Glu Ile Asn Ser His Phe Gly Thr Arg Glu Glu
        115                 120                 125

Leu Leu Lys Leu Ser Glu Glu Ile His Ala Arg Gly Met Tyr Leu Leu
    130                 135                 140

Leu Asp Val Val Ile Asn Asn Met Ala Tyr Met Thr Asp Gly Glu Asp
145                 150                 155                 160

Pro Ala Thr Thr Ile Asp Tyr Asn Val Phe Pro Gln Phe Asn Gly Ser
                165                 170                 175

Ser Tyr Phe His Pro Tyr Cys Leu Ile Thr Asn Trp Asn Asn Tyr Thr
            180                 185                 190

Asp Ala Gln Trp Cys Gln Thr Gly Asp Asn Tyr Thr Ala Leu Pro Asp
        195                 200                 205

Leu Tyr Thr Glu His Thr Ala Val Gln Asn Ile Leu Met Asp Trp Ser
    210                 215                 220

Lys Ser Val Ile Ser Asn Tyr Ser Val Asp Gly Leu Arg Ile Asp Ala
225                 230                 235                 240

Ala Lys Ser Leu Thr Pro Ser Phe Leu Pro Thr Tyr Ala Ser Thr Val
                245                 250                 255

Gly Gly Phe Met Thr Gly Glu Val Met Asp Ser Asn Ala Thr Asn Val
            260                 265                 270

Cys Lys Tyr Gln Thr Asp Tyr Leu Pro Ser Leu Pro Asn Tyr Pro Leu
        275                 280                 285

Tyr Tyr Ser Met Ile Thr Ala Phe Leu Asn Gly Glu Pro Ala Thr Leu
    290                 295                 300

Leu Glu Glu Ile Ala Thr Ile Asn Asp Leu Cys Pro Asp Thr Phe Ala
305                 310                 315                 320

Met Val Asn Phe Ile Glu Asp Gln Asp Val Asp Arg Trp Ala Tyr Met
                325                 330                 335

Asn Asp Asp Ile Met Leu Ala Lys Thr Ala Leu Thr Phe Met Met Leu
            340                 345                 350

-continued

```
Tyr Asp Gly Ile Pro Leu Val Tyr Gln Gly Leu Glu Gln Ala Ile Ala
            355                 360                 365

Tyr Ser Asn Arg Ala Ala Leu Trp Leu Thr Asp Phe Asp Thr Asn Ala
    370                 375                 380

Thr Leu Tyr Lys His Ile Lys Lys Leu Asn Ala Ile Arg Lys His Ala
385                 390                 395                 400

Ile Asn Leu Asp Ser Ser Tyr Ile Ser Ser Lys Thr Tyr Pro Ile Tyr
                405                 410                 415

Gln Gly Gly Ser Glu Leu Ala Phe Trp Lys Gly Asn Asn Gly Arg Gln
                420                 425                 430

Val Ile Met Val Leu Ser Thr Ala Gly Ser Asn Gly Ser Ala Tyr Thr
            435                 440                 445

Leu Thr Leu Pro Val Ser Tyr Gly Ala Ser Glu Val Val Thr Glu Val
                450                 455                 460

Leu Asn Cys Val Asn Tyr Thr Val Asn Thr Tyr Ser Gln Leu Val Val
465                 470                 475                 480

Asp Met Asp Lys Gly Glu Pro Arg Val Phe Phe Pro Ala Ser Met Met
                485                 490                 495

Pro Gly Ser Gly Leu Cys Gly Tyr Asn Thr Ser Asn Val Thr Tyr Ser
            500                 505                 510

Glu Leu Arg Leu Ala Ala Val Gly Ser Ser Ser Ala Gly Ser His
            515                 520                 525

Ser Val Ile Pro Ser Ala Phe Ala Ser Leu Phe Met Ala Ile Val Ala
            530                 535                 540

Phe Leu Ala Phe Arg Ala
545                 550

<210> SEQ ID NO 24
<211> LENGTH: 524
<212> TYPE: PRT
<213> ORGANISM: Aspergillus niger
<220> FEATURE:
<221> NAME/KEY: SIGNAL
<222> LOCATION: (1)..(16)

<400> SEQUENCE: 24

Met Thr Ile Phe Leu Phe Leu Ala Ile Phe Val Ala Thr Ala Leu Ala
1               5                   10                  15

Ala Thr Pro Ala Glu Trp Arg Ser Gln Ser Ile Tyr Phe Leu Leu Thr
            20                  25                  30

Asp Arg Phe Ala Arg Thr Asp Asn Ser Thr Thr Ala Ser Cys Asp Leu
        35                  40                  45

Ser Ala Arg Gln Tyr Cys Gly Gly Ser Trp Gln Gly Ile Ile Asn Gln
    50                  55                  60

Leu Asp Tyr Ile Gln Gly Met Gly Phe Thr Ala Ile Trp Ile Thr Pro
65                  70                  75                  80

Val Thr Ala Gln Ile Pro Gln Asp Thr Gly Tyr Gly Gln Ala Tyr His
                85                  90                  95

Gly Tyr Trp Gln Gln Asp Ala Tyr Ala Leu Asn Ser His Tyr Gly Thr
            100                 105                 110

Ala Asp Asp Leu Lys Ala Leu Ala Ser Ala Leu His Ser Arg Gly Met
        115                 120                 125

Tyr Leu Met Val Asp Val Val Ala Asn His Met Gly His Asn Gly Thr
    130                 135                 140

Gly Ser Ser Val Asp Tyr Ser Val Tyr Arg Pro Phe Asn Ser Gln Lys
145                 150                 155                 160
```

-continued

Tyr Phe His Asn Leu Cys Trp Ile Ser Asp Tyr Asn Gln Thr Asn
                165                 170                 175

Val Glu Asp Cys Trp Leu Gly Asp Asn Thr Val Ala Leu Pro Asp Leu
            180                 185                 190

Asp Thr Thr Ser Thr Glu Val Lys Asn Met Trp Tyr Asp Trp Val Glu
        195                 200                 205

Ser Leu Val Ser Asn Tyr Ser Val Asp Gly Leu Arg Val Asp Thr Val
    210                 215                 220

Lys Asn Val Gln Lys Asn Phe Trp Pro Gly Tyr Asn Asn Ala Ser Gly
225                 230                 235                 240

Val Tyr Cys Ile Gly Glu Val Phe Asp Gly Asp Ala Ser Tyr Thr Cys
                245                 250                 255

Pro Tyr Gln Glu Asp Leu Asp Gly Val Leu Asn Tyr Pro Met Tyr Tyr
            260                 265                 270

Pro Leu Leu Arg Ala Phe Glu Ser Thr Asn Gly Ser Ile Ser Asp Leu
        275                 280                 285

Tyr Asn Met Ile Asn Thr Val Lys Ser Thr Cys Arg Asp Ser Thr Leu
    290                 295                 300

Leu Gly Thr Phe Val Glu Asn His Asp Asn Pro Arg Phe Ala Asn Tyr
305                 310                 315                 320

Thr Ser Asp Met Ser Leu Ala Lys Asn Ala Ala Thr Phe Thr Ile Leu
                325                 330                 335

Ala Asp Gly Ile Pro Ile Ile Tyr Ala Gly Gln Glu Gln His Tyr Ser
            340                 345                 350

Gly Gly Asn Asp Pro Tyr Asn Arg Glu Ala Thr Trp Leu Ser Gly Tyr
        355                 360                 365

Lys Thr Thr Ser Glu Leu Tyr Thr His Ile Ala Ala Ser Asn Lys Ile
    370                 375                 380

Arg Thr His Ala Ile Lys Gln Asp Thr Gly Tyr Leu Thr Tyr Lys Asn
385                 390                 395                 400

Tyr Pro Ile Tyr Gln Asp Thr Ser Thr Leu Ala Met Arg Lys Gly Tyr
                405                 410                 415

Asn Gly Thr Gln Thr Ile Thr Val Leu Ser Asn Leu Gly Ala Ser Gly
            420                 425                 430

Ser Ser Tyr Thr Leu Ser Leu Pro Gly Thr Gly Tyr Thr Ala Gly Gln
        435                 440                 445

Lys Ile Thr Glu Ile Tyr Thr Cys Thr Asn Leu Thr Val Asn Ser Asn
    450                 455                 460

Gly Ser Val Pro Val Pro Met Lys Ser Gly Leu Pro Arg Ile Leu Tyr
465                 470                 475                 480

Pro Ala Asp Lys Leu Val Asn Gly Ser Ser Phe Cys Ser Ser Ala Ile
                485                 490                 495

Thr Val Phe Lys Asp Ala Gly Gly Val Leu Phe Phe Ser Tyr Thr
            500                 505                 510

Val Ile Phe Ala Gln Val Leu Ile Ala Ile Met Thr
        515                 520

<210> SEQ ID NO 25
<211> LENGTH: 632
<212> TYPE: PRT
<213> ORGANISM: Aspergillus fischeri
<220> FEATURE:
<221> NAME/KEY: SIGNAL
<222> LOCATION: (1)..(23)

```
<400> SEQUENCE: 25

Met Lys Trp Ile Ser Pro Leu Leu Pro Leu Ser Leu Ser Leu Cys Leu
1               5                   10                  15

Leu Gly Gln Ala Ala His Ala Leu Thr Pro Ala Glu Trp Arg Ser Gln
            20                  25                  30

Ser Ile Tyr Phe Leu Leu Thr Asp Arg Phe Gly Arg Glu Asp Asn Ser
        35                  40                  45

Thr Thr Ala Ala Cys Asp Val Thr Gln Arg Leu Tyr Cys Gly Gly Ser
    50                  55                  60

Trp Gln Gly Ile Ile Asn His Leu Asp Tyr Ile Gln Gly Met Gly Phe
65                  70                  75                  80

Thr Ala Ile Trp Ile Thr Pro Val Thr Gln Gln Phe Tyr Glu Asn Thr
                85                  90                  95

Gly Asp Gly Thr Ser Tyr His Gly Tyr Trp Gln Gln Asn Ile Tyr Glu
            100                 105                 110

Val Asn Ser Asn Tyr Gly Thr Ala Gln Asp Leu Arg Lys Leu Ala Asp
        115                 120                 125

Ala Leu His Ala Arg Gly Met Tyr Leu Met Val Asp Val Val Ala Asn
    130                 135                 140

His Met Gly Tyr Asp Gly Ala Gly Asn Ser Val Asp Tyr Ser Val Phe
145                 150                 155                 160

Thr Pro Phe Asp Ser Ser Thr Tyr Phe His Thr Tyr Cys Leu Ile Ser
                165                 170                 175

Asp Tyr Asn Asn Gln Asn Asn Val Glu Asp Cys Trp Leu Gly Asp Thr
            180                 185                 190

Thr Val Ser Leu Pro Asp Leu Asp Thr Thr Asn Thr Ala Val Arg Thr
        195                 200                 205

Ile Trp Tyr Asp Trp Val Lys Gly Leu Val Ala Asn Tyr Ser Ile Asp
210                 215                 220

Gly Leu Arg Ile Asp Thr Val Lys His Val Glu Lys Asp Phe Trp Pro
225                 230                 235                 240

Asp Tyr Asn Asp Ala Ala Gly Val Tyr Cys Val Gly Glu Val Phe Ser
                245                 250                 255

Gly Asp Pro Ser Tyr Thr Cys Pro Tyr Gln Asn Tyr Met Asp Gly Val
            260                 265                 270

Leu Asn Tyr Pro Ile Tyr Tyr Gln Leu Leu Tyr Ala Phe Gln Ser Thr
        275                 280                 285

Ser Gly Ser Ile Ser Asn Leu Tyr Asn Met Ile Ser Ser Val Asp Ser
    290                 295                 300

Asp Cys Ala Asp Pro Thr Leu Leu Gly Asn Phe Ile Glu Asn His Asp
305                 310                 315                 320

Asn Pro Arg Phe Ala Ser Tyr Thr Ser Asp Tyr Ser Gln Ala Lys Asn
                325                 330                 335

Val Ile Ser Phe Met Phe Phe Ser Asp Gly Ile Pro Ile Val Tyr Ala
            340                 345                 350

Gly Gln Glu Gln His Tyr Ser Gly Gly Ala Asp Pro Ala Asn Arg Glu
        355                 360                 365

Ala Val Trp Leu Ser Gly Tyr Ser Thr Ala Thr Leu Tyr Ser Trp
    370                 375                 380

Ile Ala Ser Thr Asn Lys Ile Arg Lys Leu Ala Ile Ser Lys Asp Ser
385                 390                 395                 400

Ala Tyr Ile Thr Ser Lys Asn Asn Pro Phe Tyr Tyr Asp Ser Asn Thr
                405                 410                 415
```

```
Leu Ala Met Arg Lys Gly Ser Val Ala Gly Ser Gln Val Ile Thr Val
            420                 425                 430

Leu Ser Asn Lys Gly Ser Ser Gly Ser Ser Tyr Thr Leu Ser Leu Ser
            435                 440                 445

Gly Thr Gly Tyr Ser Ala Gly Ala Thr Leu Val Glu Met Tyr Thr Cys
            450                 455                 460

Thr Thr Leu Thr Val Asp Ser Ser Gly Asn Leu Ala Val Pro Met Ala
465                 470                 475                 480

Ser Gly Leu Pro Arg Val Leu Val Pro Ser Ser Trp Val Ser Gly Ser
                485                 490                 495

Gly Leu Cys Gly Asp Ser Ile Ser Ile Ala Thr Thr Thr Thr Thr Ser
                500                 505                 510

Thr Thr Lys Thr Thr Thr Val Ala Thr Thr Thr Ala Cys Ala Ser Ala
            515                 520                 525

Thr Ala Leu Pro Ile Leu Phe Glu Glu Leu Val Thr Thr Thr Tyr Gly
            530                 535                 540

Glu Thr Ile Tyr Leu Thr Gly Ser Ile Ser Gln Leu Gly Asn Trp Asp
545                 550                 555                 560

Thr Ser Ser Ala Ile Ala Leu Ser Ala Ser Lys Tyr Thr Ser Ser Asn
                565                 570                 575

Pro Glu Trp Tyr Ala Thr Val Thr Leu Pro Val Gly Thr Ser Phe Gln
                580                 585                 590

Tyr Lys Phe Phe Lys Lys Glu Ser Asp Gly Ser Ile Val Trp Glu Ser
            595                 600                 605

Asp Pro Asn Arg Ser Tyr Thr Val Pro Ala Gly Cys Ala Gly Thr Thr
            610                 615                 620

Val Thr Val Ser Asp Thr Trp Arg
625                 630

<210> SEQ ID NO 26
<211> LENGTH: 640
<212> TYPE: PRT
<213> ORGANISM: Aspergillus luchuensis
<220> FEATURE:
<221> NAME/KEY: SIGNAL
<222> LOCATION: (1)..(21)

<400> SEQUENCE: 26

Met Arg Val Ser Thr Ser Ser Ile Ala Leu Ala Val Ser Leu Phe Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
            35                  40                  45

Ala Thr Cys Asn Thr Gly Asp Gln Ile Tyr Cys Gly Gly Ser Trp Gln
50              55                  60

Gly Ile Ile Asn His Leu Asp Tyr Ile Gln Gly Met Gly Phe Thr Ala
65              70                  75                  80

Ile Trp Ile Ser Pro Ile Thr Glu Gln Leu Pro Gln Asp Thr Ser Asp
                85                  90                  95

Gly Glu Ala Tyr His Gly Tyr Trp Gln Gln Lys Ile Tyr Tyr Val Asn
            100                 105                 110

Ser Asn Phe Gly Thr Ala Asp Asp Leu Lys Ser Leu Ser Asp Ala Leu
            115                 120                 125

His Ala Arg Gly Met Tyr Leu Met Val Asp Val Val Pro Asn His Met
```

```
                130             135             140
        Gly Tyr Ala Gly Asn Gly Asn Asp Val Asp Tyr Ser Val Phe Asp Pro
        145                 150                 155                 160

Phe Asp Ser Ser Ser Tyr Phe His Pro Tyr Cys Leu Ile Thr Asp Trp
                        165                 170                 175

Asp Asn Leu Thr Met Val Gln Asp Cys Trp Glu Gly Asp Thr Ile Val
                    180                 185                 190

Ser Leu Pro Asp Leu Asn Thr Thr Glu Thr Ala Val Arg Thr Ile Trp
                        195                 200                 205

Tyr Asp Trp Val Ala Asp Leu Val Ser Asn Tyr Ser Val Asp Gly Leu
                    210                 215                 220

Arg Ile Asp Ser Val Glu Glu Val Glu Pro Asp Phe Phe Pro Gly Tyr
        225                 230                 235                 240

Gln Glu Ala Ala Gly Val Tyr Cys Val Gly Glu Val Asp Asn Gly Asn
                        245                 250                 255

Pro Ala Leu Asp Cys Pro Tyr Gln Lys Tyr Leu Asp Gly Val Leu Asn
                    260                 265                 270

Tyr Pro Ile Tyr Trp Gln Leu Leu Tyr Ala Phe Glu Ser Ser Ser Gly
                    275                 280                 285

Ser Ile Ser Asn Leu Tyr Asn Met Ile Lys Ser Val Ala Ser Asp Cys
                290                 295                 300

Ser Asp Pro Thr Leu Leu Gly Asn Phe Ile Glu Asn His Asp Asn Pro
        305                 310                 315                 320

Arg Phe Ala Ser Tyr Thr Ser Asp Tyr Ser Gln Ala Lys Asn Val Leu
                        325                 330                 335

Ser Tyr Ile Phe Leu Ser Asp Gly Ile Pro Ile Val Tyr Ala Gly Glu
                    340                 345                 350

Glu Gln His Tyr Ser Gly Gly Asp Val Pro Tyr Asn Arg Glu Ala Thr
                        355                 360                 365

Trp Leu Ser Gly Tyr Asp Thr Ser Ala Glu Leu Tyr Thr Trp Ile Ala
                    370                 375                 380

Thr Thr Asn Ala Ile Arg Lys Leu Ala Ile Ser Ala Asp Ser Asp Tyr
        385                 390                 395                 400

Ile Thr Tyr Lys Asn Asp Pro Ile Tyr Thr Asp Ser Asn Thr Ile Ala
                        405                 410                 415

Met Arg Lys Gly Thr Ser Gly Ser Gln Ile Ile Thr Val Leu Ser Asn
                    420                 425                 430

Lys Gly Ser Ser Gly Ser Ser Tyr Thr Leu Thr Leu Ser Gly Ser Gly
                    435                 440                 445

Tyr Thr Ser Gly Thr Lys Leu Ile Glu Ala Tyr Thr Cys Thr Ser Val
                    450                 455                 460

Thr Val Asp Ser Asn Gly Asp Ile Pro Val Pro Met Ala Ser Gly Leu
        465                 470                 475                 480

Pro Arg Val Leu Leu Pro Ala Ser Val Val Asp Ser Ser Ser Leu Cys
                        485                 490                 495

Gly Gly Ser Gly Asn Thr Thr Thr Thr Thr Ala Ala Thr Ser Thr
                    500                 505                 510

Ser Lys Ala Thr Thr Ser Ser Ser Ser Ser Ala Ala Ala Thr Thr
                    515                 520                 525

Ser Ser Ser Cys Thr Ala Thr Ser Thr Thr Leu Pro Ile Thr Phe Glu
                530                 535                 540

Glu Leu Val Thr Thr Thr Tyr Gly Glu Glu Val Tyr Leu Ser Gly Ser
        545                 550                 555                 560
```

```
Ile Ser Gln Leu Gly Glu Trp His Thr Ser Asp Ala Val Lys Leu Ser
                565                 570                 575

Ala Asp Asp Tyr Thr Ser Ser Asn Pro Glu Trp Ser Val Thr Val Ser
            580                 585                 590

Leu Pro Val Gly Thr Thr Phe Glu Tyr Lys Phe Ile Lys Val Asp Glu
        595                 600                 605

Gly Gly Ser Val Thr Trp Glu Ser Asp Pro Asn Arg Glu Tyr Thr Val
        610                 615                 620

Pro Glu Cys Gly Ser Gly Ser Gly Glu Thr Val Val Asp Thr Trp Arg
625                 630                 635                 640

<210> SEQ ID NO 27
<211> LENGTH: 576
<212> TYPE: PRT
<213> ORGANISM: Gloeophyllum trabeum
<220> FEATURE:
<221> NAME/KEY: SIGNAL
<222> LOCATION: (1)..(17)

<400> SEQUENCE: 27

Met Tyr Arg Phe Leu Val Cys Ala Leu Gly Leu Leu Gly Thr Val Leu
1               5                   10                  15

Ala Gln Ser Val Asp Ser Tyr Val Gly Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ala Ala Gly Val Val Val Ala Ser Pro Ser Lys Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Ser
                85                  90                  95

Leu Ile Asp Ser Phe Val Ile Ala Glu Ala Asn Ile Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ala Thr Ala Leu Ile Thr Tyr Gly Asn Trp
145                 150                 155                 160

Leu Leu Ser Asn Gly Asn Thr Thr Trp Val Thr Ser Thr Leu Trp Pro
                165                 170                 175

Ile Ile Gln Asn Asp Leu Asn Tyr Val Val Gln Tyr Trp Asn Gln Thr
            180                 185                 190

Thr Phe Asp Leu Trp Glu Glu Val Asn Ser Ser Phe Phe Thr Thr
        195                 200                 205

Ala Val Gln His Arg Ala Leu Arg Glu Gly Ala Ala Phe Ala Thr Lys
    210                 215                 220

Ile Gly Gln Thr Ser Ser Val Ser Ser Tyr Thr Thr Gln Ala Ala Asn
225                 230                 235                 240

Leu Leu Cys Phe Leu Gln Ser Tyr Trp Asn Pro Thr Ser Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Thr
```

```
            275                 280                 285
Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Ala Ala Gln Gly Ser Leu Asn Val Thr Ser
        355                 360                 365

Ile Ser Leu Pro Phe Phe Gln Gln Phe Ser Ser Val Thr Ala Gly
370                 375                 380

Thr Tyr Ala Ser Ser Thr Thr Tyr Thr Thr Leu Thr Ser Ala Ile
385                 390                 395                 400

Lys Ser Phe Ala Asp Gly Phe Val Ala Ile Asn Ala Gln Tyr Thr Pro
                405                 410                 415

Ser Asn Gly Gly Leu Ala Glu Gln Phe Ser Arg Ser Asn Gly Ser Pro
            420                 425                 430

Val Ser Ala Val Asp Leu Thr Trp Ser Tyr Ala Ser Ala Leu Thr Ala
        435                 440                 445

Phe Glu Ala Arg Asn Asn Thr Gln Phe Ala Gly Trp Gly Ala Val Gly
    450                 455                 460

Leu Thr Val Pro Thr Ser Cys Ser Ser Asn Ser Gly Gly Gly Gly
465                 470                 475                 480

Ser Thr Val Ala Val Thr Phe Asn Val Asn Ala Gln Thr Val Trp Gly
                485                 490                 495

Glu Asn Ile Tyr Ile Thr Gly Ser Val Asp Ala Leu Ser Asn Trp Ser
            500                 505                 510

Pro Asp Asn Ala Leu Leu Leu Ser Ser Ala Asn Tyr Pro Thr Trp Ser
        515                 520                 525

Ile Thr Val Asn Leu Pro Ala Ser Thr Ala Ile Gln Tyr Lys Tyr Ile
    530                 535                 540

Arg Lys Asn Asn Gly Ala Val Thr Trp Glu Ser Asp Pro Asn Asn Ser
545                 550                 555                 560

Ile Thr Thr Pro Ala Ser Gly Ser Val Thr Glu Asn Asp Thr Trp Arg
                565                 570                 575

<210> SEQ ID NO 28
<211> LENGTH: 632
<212> TYPE: PRT
<213> ORGANISM: Trichoderma reesii
<220> FEATURE:
<221> NAME/KEY: SIGNAL
<222> LOCATION: (1)..(20)

<400> SEQUENCE: 28

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60
```

-continued

```
Ser Ala Gly Ala Val Ile Ala Ser Pro Ser Thr Ile Asp Pro Asp Tyr
 65                  70                  75                  80

Tyr Tyr Met Trp Thr Arg Asp Ser Ala Leu Val Phe Lys Asn Leu Ile
             85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Ala Asp Gly Ser Gly Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
        275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Tyr Asn Gly Asn
            340                 345                 350

Pro Trp Tyr Leu Ala Thr Phe Ala Ala Ala Glu Gln Leu Tyr Asp Ala
        355                 360                 365

Ile Tyr Val Trp Lys Lys Thr Gly Ser Ile Thr Val Thr Ala Thr Ser
    370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
        435                 440                 445

Ala Leu His Leu Thr Trp Ser Tyr Ala Ser Phe Leu Thr Ala Thr Ala
    450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
```

```
                485                 490                 495
Arg Pro Thr Ala Thr Ser Phe Pro Pro Ser Gln Thr Pro Lys Pro Gly
                500                 505                 510

Val Pro Ser Gly Thr Pro Tyr Thr Pro Leu Pro Cys Ala Thr Pro Thr
                515                 520                 525

Ser Val Ala Val Thr Phe His Glu Leu Val Ser Thr Gln Phe Gly Gln
            530                 535                 540

Thr Val Lys Val Ala Gly Asn Ala Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asn Leu Glu Ala Gly Asp Val Val Glu Tyr
            580                 585                 590

Lys Tyr Ile Asn Val Gly Gln Asp Gly Ser Val Thr Trp Glu Ser Asp
                595                 600                 605

Pro Asn His Thr Tyr Thr Val Pro Ala Val Ala Cys Val Thr Gln Val
            610                 615                 620

Val Lys Glu Asp Thr Trp Gln Ser
625                 630

<210> SEQ ID NO 29
<211> LENGTH: 574
<212> TYPE: PRT
<213> ORGANISM: Trametes cingulata
<220> FEATURE:
<221> NAME/KEY: SIGNAL
<222> LOCATION: (1)..(22)

<400> SEQUENCE: 29

Met Arg Phe Thr Leu Leu Thr Ser Leu Leu Gly Leu Ala Leu Gly Ala
1               5                   10                  15

Phe Ala Gln Ser Ser Ala Ala Asp Ala Tyr Val Ala Ser Glu Ser Pro
                20                  25                  30

Ile Ala Lys Ala Gly Val Leu Ala Asn Ile Gly Pro Ser Gly Ser Lys
            35                  40                  45

Ser Asn Gly Ala Lys Ala Gly Ile Val Ile Ala Ser Pro Ser Thr Ser
    50                  55                  60

Asn Pro Asn Tyr Leu Tyr Thr Trp Thr Arg Asp Ser Ser Leu Val Phe
65                  70                  75                  80

Lys Ala Leu Ile Asp Gln Phe Thr Thr Gly Glu Asp Thr Ser Leu Arg
                85                  90                  95

Thr Leu Ile Asp Glu Phe Thr Ser Ala Glu Ala Ile Leu Gln Gln Val
            100                 105                 110

Pro Asn Pro Ser Gly Thr Val Ser Thr Gly Leu Gly Glu Pro Lys
            115                 120                 125

Phe Asn Ile Asp Glu Thr Ala Phe Thr Asp Ala Trp Gly Arg Pro Gln
    130                 135                 140

Arg Asp Gly Pro Ala Leu Arg Ala Thr Ala Ile Ile Thr Tyr Ala Asn
145                 150                 155                 160

Trp Leu Leu Asp Asn Lys Asn Thr Thr Tyr Val Thr Asn Thr Leu Trp
                165                 170                 175

Pro Ile Ile Lys Leu Asp Leu Asp Tyr Val Ala Ser Asn Trp Asn Gln
            180                 185                 190

Ser Thr Phe Asp Leu Trp Glu Glu Ile Asn Ser Ser Phe Phe Thr
    195                 200                 205
```

```
Thr Ala Val Gln His Arg Ala Leu Arg Glu Gly Ala Thr Phe Ala Asn
210                 215                 220

Arg Ile Gly Gln Thr Ser Val Ser Gly Tyr Thr Thr Gln Ala Asn
225                 230                 235                 240

Asn Leu Leu Cys Phe Leu Gln Ser Tyr Trp Asn Pro Thr Gly Gly Tyr
                245                 250                 255

Ile Thr Ala Asn Thr Gly Gly Arg Ser Gly Lys Asp Ala Asn Thr
                260                 265                 270

Val Leu Thr Ser Ile His Thr Phe Asp Pro Ala Ala Gly Cys Asp Ala
                275                 280                 285

Val Thr Phe Gln Pro Cys Ser Asp Lys Ala Leu Ser Asn Leu Lys Val
290                 295                 300

Tyr Val Asp Ala Phe Arg Ser Ile Tyr Ser Ile Asn Ser Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
                340                 345                 350

Tyr Asp Ala Leu Ile Val Trp Asn Lys Leu Gly Ala Leu Asn Val Thr
                355                 360                 365

Ser Thr Ser Leu Pro Phe Phe Gln Gln Phe Ser Ser Gly Val Thr Val
370                 375                 380

Gly Thr Tyr Ala Ser Ser Ser Thr Phe Lys Thr Leu Thr Ser Ala
385                 390                 395                 400

Ile Lys Thr Phe Ala Asp Gly Phe Leu Ala Val Asn Ala Lys Tyr Thr
                405                 410                 415

Pro Ser Asn Gly Gly Leu Ala Glu Gln Tyr Ser Arg Ser Asn Gly Ser
                420                 425                 430

Pro Val Ser Ala Val Asp Leu Thr Trp Ser Tyr Ala Ala Ala Leu Thr
                435                 440                 445

Ser Phe Ala Ala Arg Ser Gly Lys Thr Tyr Ala Ser Trp Gly Ala Ala
450                 455                 460

Gly Leu Thr Val Pro Thr Thr Cys Ser Gly Ser Gly Gly Ala Gly Thr
465                 470                 475                 480

Val Ala Val Thr Phe Asn Val Gln Ala Thr Thr Val Phe Gly Glu Asn
                485                 490                 495

Ile Tyr Ile Thr Gly Ser Val Pro Ala Leu Gln Asn Trp Ser Pro Asp
                500                 505                 510

Asn Ala Leu Ile Leu Ser Ala Ala Asn Tyr Pro Thr Trp Ser Ser Thr
                515                 520                 525

Val Asn Leu Pro Ala Ser Thr Thr Ile Glu Tyr Lys Tyr Ile Arg Lys
530                 535                 540

Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
                565                 570
```

<210> SEQ ID NO 30
<211> LENGTH: 579
<212> TYPE: PRT
<213> ORGANISM: Athelia rolfsil
<220> FEATURE:
<221> NAME/KEY: SIGNAL
<222> LOCATION: (1)..(18)

<400> SEQUENCE: 30

```
Met Phe Arg Ser Leu Leu Ala Leu Ala Ala Cys Ala Val Ala Ser Val
1               5                   10                  15

Ser Ala Gln Ser Ala Ser Ala Thr Ala Tyr Leu Thr Lys Glu Ser Ala
            20                  25                  30

Val Ala Lys Asn Gly Val Leu Cys Asn Ile Gly Ser Gln Gly Cys Met
            35                  40                  45

Ser Glu Gly Ala Tyr Ser Gly Ile Val Ile Ala Ser Pro Ser Lys Thr
50                  55                  60

Ser Pro Asp Tyr Leu Tyr Thr Trp Thr Arg Asp Ser Ser Leu Val Phe
65                  70                  75                  80

Lys Met Leu Ile Asp Gln Tyr Thr Asn Gly Leu Asp Thr Thr Leu Arg
                85                  90                  95

Thr Leu Ile Asp Glu Phe Val Ser Ala Glu Ala Thr Ile Gln Gln Thr
                100                 105                 110

Ser Asn Ser Ser Gly Thr Val Ser Thr Gly Gly Leu Gly Glu Pro Lys
            115                 120                 125

Phe Asn Ile Asp Glu Thr Ala Phe Thr Gly Ala Trp Gly Arg Pro Gln
            130                 135                 140

Arg Asp Gly Pro Ala Leu Arg Ala Thr Ala Ile Met Thr Tyr Ala Thr
145                 150                 155                 160

Tyr Leu Tyr Asn Asn Gly Asn Thr Ser Tyr Val Thr Asn Thr Leu Trp
                165                 170                 175

Pro Ile Ile Lys Leu Asp Leu Asp Tyr Val Asn Ser Asp Trp Asn Gln
                180                 185                 190

Thr Thr Phe Asp Leu Trp Glu Glu Val Asp Ser Ser Ser Phe Phe Thr
            195                 200                 205

Thr Ala Val Gln His Arg Ala Leu Val Gln Gly Ala Ala Phe Ala Thr
            210                 215                 220

Leu Ile Gly Gln Thr Ser Ser Ala Ser Thr Tyr Ser Ala Thr Ala Pro
225                 230                 235                 240

Ser Ile Leu Cys Phe Leu Gln Ser Tyr Trp Asn Thr Asn Gly Tyr Trp
            245                 250                 255

Thr Ala Asn Thr Gly Gly Gly Arg Ser Gly Lys Asp Ala Asn Thr Ile
            260                 265                 270

Leu Ala Ser Ile His Thr Phe Asp Ala Ser Ala Gly Cys Ser Ala Ala
            275                 280                 285

Thr Ser Gln Pro Cys Ser Asp Val Ala Leu Ala Asn Leu Lys Val Tyr
            290                 295                 300

Val Asp Ser Phe Arg Ser Ile Tyr Thr Ile Asn Ser Gly Ile Ser Ser
305                 310                 315                 320

Thr Ser Gly Val Ala Thr Gly Arg Tyr Pro Glu Asp Ser Tyr Tyr Asn
            325                 330                 335

Gly Asn Pro Trp Tyr Leu Cys Thr Leu Ala Val Ala Glu Gln Leu Tyr
            340                 345                 350

Asp Ala Leu Ile Val Trp Lys Ala Gly Glu Leu Asn Val Thr Ser
            355                 360                 365

Val Ser Leu Ala Phe Phe Gln Gln Phe Asp Ser Ser Ile Thr Ala Gly
            370                 375                 380

Thr Tyr Ala Ser Ser Ser Ser Val Tyr Thr Ser Leu Ile Ser Asp Ile
385                 390                 395                 400

Gln Ala Phe Ala Asp Glu Phe Val Asp Ile Val Ala Lys Tyr Thr Pro
            405                 410                 415
```

```
Ser Ser Gly Phe Leu Ser Glu Gln Tyr Asp Lys Ser Thr Gly Ala Gln
            420                 425                 430

Asp Ser Ala Ala Asn Leu Thr Trp Ser Tyr Ala Ala Ile Thr Ala
        435                 440                 445

Tyr Gln Ala Arg Asn Gly Phe Thr Gly Ala Ser Trp Gly Ala Lys Gly
        450                 455                 460

Val Ser Thr Ser Cys Ser Thr Gly Ala Thr Ser Pro Gly Gly Ser Ser
465                 470                 475                 480

Gly Ser Val Glu Val Thr Phe Asp Val Tyr Ala Thr Thr Val Tyr Gly
                485                 490                 495

Gln Asn Ile Tyr Ile Thr Gly Asp Val Ser Glu Leu Gly Asn Trp Thr
            500                 505                 510

Pro Ala Asn Gly Val Ala Leu Ser Ser Ala Asn Tyr Pro Thr Trp Ser
            515                 520                 525

Ala Thr Ile Ala Leu Pro Ala Asp Thr Thr Ile Gln Tyr Lys Tyr Val
            530                 535                 540

Asn Ile Asp Gly Ser Thr Val Ile Trp Glu Asp Ala Ile Ser Asn Arg
545                 550                 555                 560

Glu Ile Thr Thr Pro Ala Ser Gly Thr Tyr Thr Glu Lys Asp Thr Trp
                565                 570                 575

Asp Glu Ser

<210> SEQ ID NO 31
<211> LENGTH: 604
<212> TYPE: PRT
<213> ORGANISM: Rhizopus oryzae
<220> FEATURE:
<221> NAME/KEY: SIGNAL
<222> LOCATION: (1)..(25)

<400> SEQUENCE: 31

Met Gln Leu Phe Asn Leu Pro Leu Lys Val Ser Phe Leu Val Leu
1               5                   10                  15

Ser Tyr Phe Ser Leu Leu Val Ser Ala Ala Ser Ile Pro Ser Ser Ala
                20                  25                  30

Ser Val Gln Leu Asp Ser Tyr Asn Tyr Asp Gly Ser Thr Phe Ser Gly
            35                  40                  45

Lys Ile Tyr Val Lys Asn Ile Ala Tyr Ser Lys Lys Val Thr Val Ile
50                  55                  60

Tyr Ala Asp Gly Ser Asp Asn Trp Asn Asn Gly Asn Thr Ile Ala
65                  70                  75                  80

Ala Ser Tyr Ser Ala Pro Ile Ser Gly Ser Asn Tyr Glu Tyr Trp Thr
                85                  90                  95

Phe Ser Ala Ser Ile Asn Gly Ile Lys Glu Phe Tyr Ile Lys Tyr Glu
            100                 105                 110

Val Ser Gly Lys Thr Tyr Tyr Asp Asn Asn Ser Ala Asn Tyr Gln
                115                 120                 125

Val Ser Thr Ser Lys Pro Thr Thr Thr Ala Thr Ala Thr Thr
            130                 135                 140

Thr Ala Pro Ser Thr Ser Thr Thr Pro Pro Ser Arg Ser Glu Pro
145                 150                 155                 160

Ala Thr Phe Pro Thr Gly Asn Ser Thr Ile Ser Ser Trp Ile Lys Lys
                165                 170                 175

Gln Glu Gly Ile Ser Arg Phe Ala Met Leu Arg Asn Ile Asn Pro Pro
            180                 185                 190
```

```
Gly Ser Ala Thr Gly Phe Ile Ala Ala Ser Leu Ser Thr Ala Gly Pro
            195                 200                 205

Asp Tyr Tyr Tyr Ala Trp Thr Arg Asp Ala Ala Leu Thr Ser Asn Val
210                 215                 220

Ile Val Tyr Glu Tyr Asn Thr Thr Leu Ser Gly Asn Lys Thr Ile Leu
225                 230                 235                 240

Asn Val Leu Lys Asp Tyr Val Thr Phe Ser Val Lys Thr Gln Ser Thr
                245                 250                 255

Ser Thr Val Cys Asn Cys Leu Gly Glu Pro Lys Phe Asn Pro Asp Ala
                260                 265                 270

Ser Gly Tyr Thr Gly Ala Trp Gly Arg Pro Gln Asn Asp Gly Pro Ala
                275                 280                 285

Glu Arg Ala Thr Thr Phe Ile Leu Phe Ala Asp Ser Tyr Leu Thr Gln
            290                 295                 300

Thr Lys Asp Ala Ser Tyr Val Thr Gly Thr Leu Lys Pro Ala Ile Phe
305                 310                 315                 320

Lys Asp Leu Asp Tyr Val Val Asn Val Trp Ser Asn Gly Cys Phe Asp
                325                 330                 335

Leu Trp Glu Glu Val Asn Gly Val His Phe Tyr Thr Leu Met Val Met
            340                 345                 350

Arg Lys Gly Leu Leu Leu Gly Ala Asp Phe Ala Lys Arg Asn Gly Asp
            355                 360                 365

Ser Thr Arg Ala Ser Thr Tyr Ser Ser Thr Ala Ser Thr Ile Ala Asn
    370                 375                 380

Lys Ile Ser Ser Phe Trp Val Ser Ser Asn Asn Trp Ile Gln Val Ser
385                 390                 395                 400

Gln Ser Val Thr Gly Gly Val Ser Lys Lys Gly Leu Asp Val Ser Thr
                405                 410                 415

Leu Leu Ala Ala Asn Leu Gly Ser Val Asp Asp Gly Phe Phe Thr Pro
                420                 425                 430

Gly Ser Glu Lys Ile Leu Ala Thr Ala Val Ala Val Glu Asp Ser Phe
            435                 440                 445

Ala Ser Leu Tyr Pro Ile Asn Lys Asn Leu Pro Ser Tyr Leu Gly Asn
            450                 455                 460

Ser Ile Gly Arg Tyr Pro Glu Asp Thr Tyr Asn Gly Asn Gly Asn Ser
465                 470                 475                 480

Gln Gly Asn Ser Trp Phe Leu Ala Val Thr Gly Tyr Ala Glu Leu Tyr
                485                 490                 495

Tyr Arg Ala Ile Lys Glu Trp Ile Gly Asn Gly Val Thr Val Ser
                500                 505                 510

Ser Ile Ser Leu Pro Phe Phe Lys Lys Phe Asp Ser Ser Ala Thr Ser
            515                 520                 525

Gly Lys Lys Tyr Thr Val Gly Thr Ser Asp Phe Asn Asn Leu Ala Gln
            530                 535                 540

Asn Ile Ala Leu Ala Ala Asp Arg Phe Leu Ser Thr Val Gln Leu His
545                 550                 555                 560

Ala His Asn Asn Gly Ser Leu Ala Glu Glu Phe Asp Arg Thr Thr Gly
                565                 570                 575

Leu Ser Thr Gly Ala Arg Asp Leu Thr Trp Ser His Ala Ser Leu Ile
                580                 585                 590

Thr Ala Ser Tyr Ala Lys Ala Gly Ala Pro Ala Ala
            595                 600
```

-continued

```
<210> SEQ ID NO 32
<211> LENGTH: 612
<212> TYPE: PRT
<213> ORGANISM: Aspergillus oryzae
<220> FEATURE:
<221> NAME/KEY: SIGNAL
<222> LOCATION: (1)..(19)

<400> SEQUENCE: 32
```

Met Val Ser Phe Ser Ser Cys Leu Arg Ala Leu Ala Leu Gly Ser Ser
1               5                   10                  15

Val Leu Ala Val Gln Pro Val Leu Arg Gln Ala Thr Gly Leu Asp Thr
            20                  25                  30

Trp Leu Ser Thr Glu Ala Asn Phe Ser Arg Gln Ala Ile Leu Asn Asn
        35                  40                  45

Ile Gly Ala Asp Gly Gln Ser Ala Gln Gly Ala Ser Pro Gly Val Val
    50                  55                  60

Ile Ala Ser Pro Ser Lys Ser Asp Pro Asp Tyr Phe Tyr Thr Trp Thr
65                  70                  75                  80

Arg Asp Ser Gly Leu Val Met Lys Thr Leu Val Asp Leu Phe Arg Gly
                85                  90                  95

Gly Asp Ala Asp Leu Leu Pro Ile Ile Glu Glu Phe Ile Ser Ser Gln
            100                 105                 110

Ala Arg Ile Gln Gly Ile Ser Asn Pro Ser Gly Ala Leu Ser Ser Gly
        115                 120                 125

Gly Leu Gly Glu Pro Lys Phe Asn Val Asp Glu Thr Ala Phe Thr Gly
    130                 135                 140

Ala Trp Gly Arg Pro Gln Arg Asp Gly Pro Ala Leu Arg Ala Thr Ala
145                 150                 155                 160

Met Ile Ser Phe Gly Glu Trp Leu Val Glu Asn Ser His Thr Ser Ile
                165                 170                 175

Ala Thr Asp Leu Val Trp Pro Val Val Arg Asn Asp Leu Ser Tyr Val
            180                 185                 190

Ala Gln Tyr Trp Ser Gln Ser Gly Phe Asp Leu Trp Glu Glu Val Gln
        195                 200                 205

Gly Thr Ser Phe Phe Thr Val Ala Val Ser His Arg Ala Leu Val Glu
    210                 215                 220

Gly Ser Ser Phe Ala Lys Thr Val Gly Ser Ser Cys Pro Tyr Cys Asp
225                 230                 235                 240

Ser Gln Ala Pro Gln Val Arg Cys Tyr Leu Gln Ser Phe Trp Thr Gly
                245                 250                 255

Ser Tyr Ile Gln Ala Asn Phe Gly Gly Arg Ser Gly Lys Asp Ile
            260                 265                 270

Asn Thr Val Leu Gly Ser Ile His Thr Phe Asp Pro Gln Ala Thr Cys
        275                 280                 285

Asp Asp Ala Thr Phe Gln Pro Cys Ser Ala Arg Ala Leu Ala Asn His
    290                 295                 300

Lys Val Val Thr Asp Ser Phe Arg Ser Ile Tyr Ala Ile Asn Ser Gly
305                 310                 315                 320

Arg Ala Glu Asn Gln Ala Val Ala Val Gly Arg Tyr Pro Glu Asp Ser
                325                 330                 335

Tyr Tyr Asn Gly Asn Pro Trp Phe Leu Thr Thr Leu Ala Ala Ala Glu
            340                 345                 350

Gln Leu Tyr Asp Ala Leu Tyr Gln Trp Asp Lys Ile Gly Ser Leu Ala
        355                 360                 365

```
Ile Thr Asp Val Ser Leu Pro Phe Phe Lys Ala Leu Tyr Ser Ser Ala
    370                 375                 380

Ala Thr Gly Thr Tyr Ala Ser Ser Thr Thr Val Tyr Lys Asp Ile Val
385                 390                 395                 400

Ser Ala Val Lys Ala Tyr Ala Asp Gly Tyr Val Gln Ile Val Gln Thr
                405                 410                 415

Tyr Ala Ala Ser Thr Gly Ser Met Ala Glu Gln Tyr Thr Lys Thr Asp
                420                 425                 430

Gly Ser Gln Thr Ser Ala Arg Asp Leu Thr Trp Ser Tyr Ala Ala Leu
            435                 440                 445

Leu Thr Ala Asn Asn Arg Arg Asn Ala Val Val Pro Ala Pro Trp Gly
450                 455                 460

Glu Thr Ala Ala Thr Ser Ile Pro Ser Ala Cys Ser Thr Thr Ser Ala
465                 470                 475                 480

Ser Gly Thr Tyr Ser Ser Val Val Ile Thr Ser Trp Pro Thr Ile Ser
                485                 490                 495

Gly Tyr Pro Gly Ala Pro Asp Ser Pro Cys Gln Val Pro Thr Thr Val
                500                 505                 510

Ser Val Thr Phe Ala Val Lys Ala Thr Thr Val Tyr Gly Glu Ser Ile
                515                 520                 525

Lys Ile Val Gly Ser Ile Ser Gln Leu Gly Ser Trp Asn Pro Ser Ser
530                 535                 540

Ala Thr Ala Leu Asn Ala Asp Ser Tyr Thr Thr Asp Asn Pro Leu Trp
545                 550                 555                 560

Thr Gly Thr Ile Asn Leu Pro Ala Gly Gln Ser Phe Glu Tyr Lys Phe
                565                 570                 575

Ile Arg Val Gln Asn Gly Ala Val Thr Trp Glu Ser Asp Pro Asn Arg
                580                 585                 590

Lys Tyr Thr Val Pro Ser Thr Cys Gly Val Lys Ser Ala Val Gln Ser
                595                 600                 605

Asp Val Trp Arg
        610

<210> SEQ ID NO 33
<211> LENGTH: 630
<212> TYPE: PRT
<213> ORGANISM: Ophiostoma floccosum
<220> FEATURE:
<221> NAME/KEY: SIGNAL
<222> LOCATION: (1)..(18)

<400> SEQUENCE: 33

Met Lys Leu Ser Ser Leu Leu Pro Leu Ala Phe Leu Gly Gln Ala Val
1               5                   10                  15

Asn Ala Leu Ser Pro Ala Glu Trp Arg Lys Gln Ser Ile Tyr Phe Leu
            20                  25                  30

Leu Thr Asp Arg Phe Gly Arg Thr Asp Asn Ser Thr Ser Ala Thr Cys
        35                  40                  45

Asn Thr Gly Asp Arg Ala Tyr Cys Gly Gly Ser Trp Gln Gly Val Ile
    50                  55                  60

Asn His Leu Asp Tyr Ile Gln Gly Met Gly Phe Thr Ala Ile Trp Ile
65                  70                  75                  80

Thr Pro Val Thr Gly Gln Phe Tyr Glu Ser Thr Gly Asp Gly Thr Ser
                85                  90                  95

Tyr His Gly Tyr Trp Gln Gln Asp Ile Tyr Ser Leu Asn Ser His Leu
                100                 105                 110
```

```
Gly Asp Gln Asn Asp Leu Lys Ala Leu Ser Ala Ala Leu His Ala Arg
            115                 120                 125
Gly Met Tyr Leu Met Val Asp Val Ala Asn His Met Gly Tyr Asp
        130                 135                 140
Gly Ala Gly Ser Asn Val Asp Tyr Ser Val Phe Asp Ala Phe Pro Ser
145                 150                 155                 160
Ser Ser Tyr Phe His Ser Tyr Cys Glu Ile Ser Asn Tyr Asp Asp Gln
                165                 170                 175
Ser Asn Val Glu Asp Cys Trp Leu Gly Asp Thr Thr Val Ser Leu Pro
            180                 185                 190
Asp Leu Asn Thr Glu Leu Thr Ser Val Arg Ser Ile Trp Asn Ser Trp
            195                 200                 205
Val Ala Gly Leu Val Ala Asn Tyr Ser Ile Asp Gly Leu Arg Ile Asp
        210                 215                 220
Thr Val Lys His Val Glu Thr Ser Phe Trp Pro Gly Tyr Asn Asp Ala
225                 230                 235                 240
Ala Gly Val Tyr Cys Val Gly Glu Val Phe Asp Gly Asp Pro Ala Tyr
                245                 250                 255
Thr Cys Ala Tyr Gln Asn Tyr Met Asp Gly Val Leu Asn Tyr Pro Ile
            260                 265                 270
Tyr Tyr Gln Leu Leu Ser Ala Phe Glu Ser Thr Ser Gly Ser Ile Ser
        275                 280                 285
Asn Leu Tyr Asn Met Ile Lys Ser Val Ala Ser Asp Cys Ala Asp Pro
        290                 295                 300
Thr Leu Leu Gly Asn Phe Ile Glu Asn His Asp Asn Pro Arg Phe Ala
305                 310                 315                 320
Ser Tyr Thr Ser Asp Tyr Ser Leu Ala Gln Asn Ala Ile Ser Phe Leu
                325                 330                 335
Phe Phe Ser Asp Gly Ile Pro Ile Val Tyr Ser Gly Gln Glu Gln His
            340                 345                 350
Tyr Ser Gly Gly Ala Asp Pro Ala Asn Arg Glu Ala Thr Trp Leu Ser
        355                 360                 365
Gly Tyr Ser Thr Thr Ala Thr Leu Tyr Lys His Ile Lys Thr Thr Asn
        370                 375                 380
Gln Ile Arg Ser Leu Ile Ile Gly Lys Asp Ser Ser Trp Ala Thr Ser
385                 390                 395                 400
Ala Asn Ser Pro Phe Tyr Gln Asp Ser Asn Thr Ile Ala Met Leu Lys
                405                 410                 415
Gly Ser Ala Ser Gly Ser Lys Val Leu Thr Val Leu Ser Asn Lys Gly
            420                 425                 430
Ala Ser Gly Ser Ser Tyr Thr Leu Ser Leu Gly Ser Thr Gly Tyr Ser
        435                 440                 445
Ser Gly Ala Ser Leu Val Glu Leu Tyr Ser Cys Thr Thr Val Thr Val
        450                 455                 460
Asp Ser Ser Gly Asn Val Pro Val Pro Met Ala Ser Gly Leu Pro Arg
465                 470                 475                 480
Val Leu Val Pro Ser Ser Trp Val Ser Gly Ser Gly Leu Cys Gly Thr
                485                 490                 495
Ala Val Thr Thr Gly Thr Ala Thr Ala Thr Gly Thr Ser Thr Lys Ala
            500                 505                 510
Thr Thr Ala Thr Ala Thr Ala Thr Ser Cys Thr Ala Ala Thr Ala
        515                 520                 525
```

```
Val Ser Val Val Phe Asn Glu Leu Ala Thr Thr Tyr Gly Glu Asn
            530                 535                 540

Val Tyr Ile Ile Gly Ser Thr Ser Gln Leu Gly Ser Trp Ser Thr Ala
545                 550                 555                 560

Asn Ala Ile Ala Leu Ser Ser Ser Asp Tyr Thr Ser Ser Asn Pro Leu
                565                 570                 575

Trp His Val Thr Val Ser Leu Pro Ala Gly Ser Ser Phe Thr Tyr Lys
            580                 585                 590

Phe Ile Lys Lys Glu Ser Asp Gly Thr Phe Val Trp Glu Ser Asp Pro
            595                 600                 605

Asn Arg Ser Tyr Thr Val Pro Thr Gly Cys Ser Gly Leu Ser Ala Thr
610                 615                 620

Val Ser Ala Thr Trp Arg
625                 630

<210> SEQ ID NO 34
<211> LENGTH: 620
<212> TYPE: PRT
<213> ORGANISM: Trichocladium griseum
<220> FEATURE:
<221> NAME/KEY: SIGNAL
<222> LOCATION: (1)..(19)

<400> SEQUENCE: 34

Met His Thr Phe Ser Lys Leu Leu Val Leu Gly Ser Ala Val Gln Ser
1               5                   10                  15

Ala Leu Gly Arg Pro His Gly Ser Ser Arg Leu Gln Glu Arg Ala Ala
            20                  25                  30

Val Asp Thr Phe Ile Asn Thr Glu Lys Pro Ile Ala Trp Asn Lys Leu
        35                  40                  45

Leu Ala Asn Ile Gly Pro Asn Gly Lys Ala Ala Pro Gly Ala Ala Ala
    50                  55                  60

Gly Val Val Ile Ala Ser Pro Ser Arg Thr Asp Pro Pro Tyr Phe Phe
65                  70                  75                  80

Thr Trp Thr Pro Asp Ala Ala Leu Val Leu Thr Gly Ile Ile Glu Ser
                85                  90                  95

Leu Gly His Asn Tyr Asn Thr Thr Leu Gln Gln Val Ser Asn Pro Ser
            100                 105                 110

Gly Thr Phe Ala Asp Gly Ser Gly Leu Gly Glu Ala Lys Phe Asn Val
        115                 120                 125

Asp Leu Thr Ala Phe Thr Gly Glu Trp Gly Arg Pro Gln Arg Asp Gly
    130                 135                 140

Pro Pro Leu Arg Ala Ile Ala Leu Ile Gln Tyr Ala Lys Trp Leu Ile
145                 150                 155                 160

Ala Asn Gly Tyr Lys Ser Thr Ala Lys Ser Val Val Trp Pro Val Val
                165                 170                 175

Lys Asn Asp Leu Ala Tyr Thr Ala Gln Tyr Trp Asn Glu Thr Gly Phe
            180                 185                 190

Asp Leu Trp Glu Glu Val Pro Gly Ser Ser Phe Phe Thr Ile Ala Ser
        195                 200                 205

Ser His Arg Ala Leu Thr Glu Gly Ala Tyr Leu Ala Gln Leu Asp
    210                 215                 220

Thr Glu Cys Pro Pro Cys Thr Thr Val Ala Pro Gln Val Leu Cys Phe
225                 230                 235                 240

Gln Gln Ala Phe Trp Asn Ser Lys Gly Asn Tyr Val Val Ser Thr Ser
                245                 250                 255
```

```
Thr Ala Gly Glu Tyr Arg Ser Gly Lys Asp Ala Asn Ser Ile Leu Ala
            260                 265                 270

Ser Ile His Asn Phe Asp Pro Glu Ala Gly Cys Asp Asn Leu Thr Phe
            275                 280                 285

Gln Pro Cys Ser Glu Arg Ala Leu Ala Asn His Lys Ala Tyr Val Asp
290                 295                 300

Ser Phe Arg Asn Leu Tyr Ala Ile Asn Lys Gly Ile Ala Gln Gly Lys
305                 310                 315                 320

Ala Val Ala Val Gly Arg Tyr Ser Glu Asp Val Tyr Asn Gly Asn
                325                 330                 335

Pro Trp Tyr Leu Ala Asn Phe Ala Ala Glu Gln Leu Tyr Asp Ala
            340                 345                 350

Ile Tyr Val Trp Asn Lys Gln Gly Ser Ile Thr Val Thr Ser Val Ser
            355                 360                 365

Leu Pro Phe Phe Arg Asp Leu Val Ser Val Ser Thr Gly Thr Tyr
            370                 375                 380

Ser Lys Ser Ser Ser Thr Phe Thr Asn Ile Val Asn Ala Val Lys Ala
385                 390                 395                 400

Tyr Ala Asp Gly Phe Ile Glu Val Ala Ala Lys Tyr Thr Pro Ser Asn
                405                 410                 415

Gly Ala Leu Ala Glu Gln Tyr Asp Arg Asn Thr Gly Lys Pro Asp Ser
            420                 425                 430

Ala Ala Asp Leu Thr Trp Ser Tyr Ser Ala Phe Leu Ser Ala Ile Asp
            435                 440                 445

Arg Arg Ala Gly Leu Val Pro Pro Ser Trp Arg Ala Ser Val Ala Lys
450                 455                 460

Ser Gln Leu Pro Ser Thr Cys Ser Arg Ile Glu Val Ala Gly Thr Tyr
465                 470                 475                 480

Val Ala Ala Thr Ser Thr Ser Phe Pro Ser Lys Gln Thr Pro Asn Pro
                485                 490                 495

Ser Ala Ala Pro Ser Pro Ser Pro Tyr Pro Thr Ala Cys Ala Asp Ala
            500                 505                 510

Ser Glu Val Tyr Val Thr Phe Asn Glu Arg Val Ser Thr Ala Trp Gly
            515                 520                 525

Glu Thr Ile Lys Val Val Gly Asn Val Pro Ala Leu Gly Asn Trp Asp
530                 535                 540

Thr Ser Lys Ala Val Thr Leu Ser Ala Ser Gly Tyr Lys Ser Asn Asp
545                 550                 555                 560

Pro Leu Trp Ser Ile Thr Val Pro Ile Lys Ala Thr Gly Ser Ala Val
                565                 570                 575

Gln Tyr Lys Tyr Ile Lys Val Gly Thr Asn Gly Lys Ile Thr Trp Glu
            580                 585                 590

Ser Asp Pro Asn Arg Ser Ile Thr Leu Gln Thr Ala Ser Ser Ala Gly
            595                 600                 605

Lys Cys Ala Ala Gln Thr Val Asn Asp Ser Trp Arg
610                 615                 620
```

<210> SEQ ID NO 35
<211> LENGTH: 639
<212> TYPE: PRT
<213> ORGANISM: Aspergillus awamori
<220> FEATURE:
<221> NAME/KEY: SIGNAL
<222> LOCATION: (1)..(18)

<400> SEQUENCE: 35

```
Met Ser Phe Arg Ser Leu Leu Ala Leu Ser Gly Leu Val Cys Ser Gly
1               5                   10                  15

Leu Ala Ser Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Ile Lys Thr Leu Val Asp Leu Phe Arg Asn Gly Asp Thr
                85                  90                  95

Asp Leu Leu Ser Thr Ile Glu Asn Tyr Ile Ser Ser Gln Ala Ile Val
                100                 105                 110

Gln Gly Ile Ser Asn Pro Ser Gly Asp Leu Ser Ser Gly Gly Leu Gly
            115                 120                 125

Glu Pro Lys Phe Asn Val Asp Glu Thr Ala Tyr Thr Gly Ser Trp Gly
        130                 135                 140

Arg Pro Gln Arg Asp Gly Pro Ala Leu Arg Ala Thr Ala Met Ile Gly
145                 150                 155                 160

Phe Arg Gln Trp Leu Leu Asp Asn Gly Tyr Thr Ser Ala Ala Thr Glu
                165                 170                 175

Ile Val Trp Pro Leu Val Arg Asn Asp Leu Ser Tyr Val Ala Gln Tyr
                180                 185                 190

Trp Asn Gln Thr Gly Tyr Asp Leu Trp Glu Glu Val Asn Gly Ser Ser
            195                 200                 205

Phe Phe Thr Ile Ala Val Gln His Arg Ala Leu Val Glu Gly Ser Ala
210                 215                 220

Phe Ala Thr Ala Val Gly Ser Ser Cys Ser Trp Cys Asp Ser Gln Ala
225                 230                 235                 240

Pro Gln Ile Leu Cys Tyr Leu Gln Ser Phe Trp Thr Gly Glu Tyr Ile
                245                 250                 255

Leu Ala Asn Phe Asp Ser Ser Arg Ser Gly Lys Asp Thr Asn Thr Leu
                260                 265                 270

Leu Gly Ser Ile His Thr Phe Asp Pro Glu Ala Gly Cys Asp Asp Ser
            275                 280                 285

Thr Phe Gln Pro Cys Ser Pro Arg Ala Leu Ala Asn His Lys Glu Val
        290                 295                 300

Val Asp Ser Phe Arg Ser Ile Tyr Thr Leu Asn Asp Gly Leu Ser Asp
305                 310                 315                 320

Ser Glu Ala Val Ala Val Gly Arg Tyr Pro Lys Asp Ser Tyr Tyr Asn
                325                 330                 335

Gly Asn Pro Trp Phe Leu Cys Thr Leu Ala Ala Ala Glu Gln Leu Tyr
            340                 345                 350

Asp Ala Leu Tyr Gln Trp Asp Lys Gln Gly Ser Leu Glu Ile Thr Asp
        355                 360                 365

Val Ser Leu Asp Phe Phe Gln Ala Leu Tyr Ser Asp Ala Ala Thr Gly
    370                 375                 380

Thr Tyr Ser Ser Ser Ser Ser Thr Tyr Ser Ser Ile Val Asp Ala Val
385                 390                 395                 400

Lys Thr Phe Ala Asp Gly Phe Val Ser Ile Val Glu Thr His Ala Ala
                405                 410                 415
```

Ser Asn Gly Ser Leu Ser Glu Gln Tyr Asp Lys Ser Asp Gly Asp Glu
            420                 425                 430

Leu Ser Ala Arg Asp Leu Thr Trp Ser Tyr Ala Ala Leu Leu Thr Ala
            435                 440                 445

Asn Asn Arg Arg Asn Ser Val Met Pro Pro Ser Trp Gly Glu Thr Ser
450                 455                 460

Ala Ser Ser Val Pro Gly Thr Cys Ala Ala Thr Ser Ala Ser Gly Thr
465                 470                 475                 480

Tyr Ser Ser Val Thr Val Thr Ser Ser Pro Ser Ile Val Ala Thr Gly
                485                 490                 495

Gly Thr Thr Thr Thr Ala Thr Thr Thr Gly Phe Gly Gly Val Thr Ser
            500                 505                 510

Thr Ser Lys Thr Thr Thr Thr Ala Ser Lys Thr Ser Thr Thr Thr Ser
            515                 520                 525

Ser Thr Ser Cys Thr Thr Pro Thr Ala Val Ala Val Thr Phe Asp Leu
            530                 535                 540

Thr Ala Thr Thr Thr Tyr Gly Glu Asn Ile Tyr Leu Val Gly Ser Ile
545                 550                 555                 560

Ser Gln Leu Gly Asp Trp Asp Thr Ser Asp Gly Ile Ala Leu Ser Ala
                565                 570                 575

Asp Lys Tyr Thr Ser Ser Asn Pro Leu Trp Tyr Val Thr Val Thr Leu
            580                 585                 590

Pro Ala Gly Glu Ser Phe Glu Tyr Lys Phe Ile Arg Ile Glu Ser Asp
            595                 600                 605

Asp Ser Val Glu Trp Glu Ser Asp Pro Asn Arg Glu Tyr Thr Val Pro
            610                 615                 620

Gln Ala Cys Gly Glu Ser Thr Ala Thr Val Thr Asp Thr Trp Arg
625                 630                 635

<210> SEQ ID NO 36
<211> LENGTH: 639
<212> TYPE: PRT
<213> ORGANISM: Aspergillus niger
<220> FEATURE:
<221> NAME/KEY: SIGNAL
<222> LOCATION: (1)..(18)

<400> SEQUENCE: 36

Met Ser Phe Arg Ser Leu Leu Ala Leu Ser Gly Leu Val Cys Thr Gly
1               5                   10                  15

Leu Ala Asn Val Ile Ser Lys Arg Ala Thr Trp Asp Ser Trp Leu Ser
            20                  25                  30

Asn Glu Ala Thr Val Ala Arg Thr Ala Ile Leu Asn Asn Ile Gly Ala
                35                  40                  45

Asp Gly Ala Trp Val Ser Gly Ala Asp Ser Gly Ile Val Val Ala Ser
        50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp

```
                130                 135                 140
Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
                180                 185                 190

Tyr Trp Asn Gln Thr Gly Tyr Asp Leu Trp Glu Val Asn Gly Ser Ser
                195                 200                 205

Phe Phe Thr Ile Ala Val Gln His Arg Ala Leu Val Glu Gly Ser Ala
210                 215                 220

Phe Ala Thr Ala Val Gly Ser Ser Cys Ser Trp Cys Asp Ser Gln Ala
225                 230                 235                 240

Pro Glu Ile Leu Cys Tyr Leu Gln Ser Phe Trp Thr Gly Ser Phe Ile
                245                 250                 255

Leu Ala Asn Phe Asp Ser Ser Arg Ser Ala Lys Asp Ala Asn Thr Leu
                260                 265                 270

Leu Leu Gly Ser Ile His Thr Phe Asp Pro Glu Ala Ala Cys Asp Asp
                275                 280                 285

Ser Thr Phe Gln Pro Cys Ser Pro Arg Ala Leu Ala Asn His Lys Glu
                290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
                340                 345                 350

Tyr Asp Ala Leu Tyr Gln Trp Asp Lys Gln Gly Ser Leu Glu Val Thr
                355                 360                 365

Asp Val Ser Leu Asp Phe Phe Lys Ala Leu Tyr Ser Asp Ala Thr Gly
                370                 375                 380

Thr Tyr Ser Ser Ser Ser Thr Tyr Ser Ser Ile Val Asp Ala Val
385                 390                 395                 400

Lys Thr Phe Ala Asp Gly Phe Val Ser Ile Val Glu Thr His Ala Ala
                405                 410                 415

Ser Asn Gly Ser Met Ser Glu Gln Tyr Asp Lys Ser Asp Gly Glu Gln
                420                 425                 430

Leu Ser Ala Arg Asp Leu Thr Trp Ser Tyr Ala Ala Leu Leu Thr Ala
                435                 440                 445

Asn Asn Arg Arg Asn Val Val Pro Ser Ala Ser Trp Gly Glu Thr Ser
450                 455                 460

Ala Ser Ser Val Pro Gly Thr Cys Ala Ala Thr Ser Ala Ile Gly Thr
465                 470                 475                 480

Tyr Ser Ser Val Thr Val Thr Ser Trp Pro Ser Ile Val Ala Thr Gly
                485                 490                 495

Gly Thr Thr Thr Thr Ala Thr Pro Thr Gly Ser Gly Ser Val Thr Ser
                500                 505                 510

Thr Ser Lys Thr Thr Ala Thr Ala Ser Lys Thr Ser Thr Ser Thr Ser
                515                 520                 525

Ser Thr Ser Cys Thr Thr Pro Thr Ala Val Ala Val Thr Phe Asp Leu
                530                 535                 540

Thr Ala Thr Thr Thr Tyr Gly Glu Asn Ile Tyr Leu Val Gly Ser Ile
545                 550                 555                 560
```

```
Ser Gln Leu Gly Asp Trp Glu Thr Ser Asp Gly Ile Ala Leu Ser Ala
            565                 570                 575
Asp Lys Tyr Thr Ser Ser Asp Pro Leu Trp Tyr Val Thr Val Thr Leu
            580                 585                 590
Pro Ala Gly Glu Ser Phe Glu Tyr Lys Phe Ile Arg Ile Glu Ser Asp
        595                 600                 605
Asp Ser Val Glu Trp Glu Ser Asp Pro Asn Arg Glu Tyr Thr Val Pro
    610                 615                 620
Gln Ala Cys Gly Thr Ser Thr Ala Thr Val Thr Asp Thr Trp Arg
625                 630                 635
```